(12) United States Patent
Whitman et al.

(10) Patent No.: US 8,858,589 B2
(45) Date of Patent: *Oct. 14, 2014

(54) SURGICAL DEVICE

(71) Applicant: Covidien LP, Mansfield, MA (US)

(72) Inventors: Michael P. Whitman, New Hope, PA (US); John E. Burbank, Ridgefield, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/955,563

(22) Filed: Jul. 31, 2013

(65) Prior Publication Data

US 2014/0008411 A1    Jan. 9, 2014

Related U.S. Application Data

(63) Continuation of application No. 13/217,611, filed on Aug. 25, 2011, now Pat. No. 8,518,074, which is a continuation of application No. 10/094,051, filed on Mar. 8, 2002, now Pat. No. 8,016,855.

(60) Provisional application No. 60/346,656, filed on Jan. 8, 2002.

(51) Int. Cl.
| | |
|---|---|
| *A61B 17/28* | (2006.01) |
| *A61B 17/068* | (2006.01) |
| *A61B 17/072* | (2006.01) |
| *A61B 17/285* | (2006.01) |
| *A61B 19/00* | (2006.01) |
| *A61B 17/00* | (2006.01) |
| *A61B 17/32* | (2006.01) |

(52) U.S. Cl.
CPC ....... *A61B 17/285* (2013.01); *A61B 2019/2242* (2013.01); *A61B 2017/00398* (2013.01); *A61B 2017/320052* (2013.01); *A61B 2017/00473* (2013.01); *A61B 19/22* (2013.01); *A61B 19/2203* (2013.01); *A61B 2017/00464* (2013.01); *A61B 2017/003* (2013.01); *A61B 2017/00477* (2013.01); *A61B 17/072* (2013.01); *A61B 17/068* (2013.01); *A61B 2017/07214* (2013.01)
USPC ......................................... 606/205; 227/175.1

(58) Field of Classification Search
USPC ................. 606/139, 205–208, 219; 227/175.1–182.1
See application file for complete search history.

(56) References Cited

U.S. PATENT DOCUMENTS

| | | | |
|---|---|---|---|
| 1,798,902 A | | 3/1931 | Raney |
| 1,881,250 A | * | 10/1932 | Tomlinson ...................... 606/45 |

(Continued)

FOREIGN PATENT DOCUMENTS

| | | |
|---|---|---|
| DE | 2044108 A1 | 3/1972 |
| DE | 2330182 A1 | 1/1975 |

(Continued)

OTHER PUBLICATIONS

New York Magazine, Jun. 10, 2002 The Best Doctors in New York, p. 80.

*Primary Examiner* — Ryan Severson

(57) ABSTRACT

A surgical device includes a first jaw and a second jaw in opposed correspondence with the first jaw. A first driver is configured to cause relative movement of the first jaw and the second jaw in a plane. The first driver is configured to engage a drive shaft rotatable about a rotation axis arranged in non-parallel, e.g., perpendicular, correspondence to the plane. The device may also include a surgical member, e.g., a cutting and stapling element, disposed within the first jaw. A second driver is configured to cause relative movement of the surgical member in a direction parallel to the plane. The second driver is configured to engage a drive shaft rotatable about a rotation axis arranged in non-parallel correspondence to the plane.

18 Claims, 34 Drawing Sheets

(56) References Cited

U.S. PATENT DOCUMENTS

| | | | |
|---|---|---|---|
| 2,031,682 A | 2/1936 | Wappler et al. | |
| 2,174,219 A | 9/1939 | Balma | |
| 2,246,647 A | 6/1941 | Vancura | |
| 2,419,045 A | 4/1947 | Whittaker | |
| 2,725,628 A | 12/1955 | O'Neilly et al. | |
| 2,887,111 A * | 5/1959 | Leyro Diaz | 606/148 |
| 3,079,606 A | 3/1963 | Bobrov et al. | |
| 3,080,564 A * | 3/1963 | Strekopitov et al. | 227/153 |
| 3,120,845 A | 2/1964 | Homer | |
| 3,193,165 A | 7/1965 | Akhalaya et al. | |
| 3,252,643 A | 5/1966 | Strekopov et al. | |
| 3,253,643 A | 5/1966 | Gudheim | |
| 3,256,875 A | 6/1966 | Tsepelev et al. | |
| 3,275,211 A * | 9/1966 | Hirsch et al. | 227/124 |
| 3,315,863 A | 4/1967 | O'Dea | |
| 3,317,105 A | 5/1967 | Astafjev et al. | |
| 3,388,847 A | 6/1968 | Kasulin et al. | |
| 3,490,576 A | 1/1970 | Alessi et al. | |
| 3,490,675 A | 1/1970 | Green et al. | |
| 3,494,533 A | 2/1970 | Green et al. | |
| 3,499,591 A | 3/1970 | Green | |
| 3,503,396 A * | 3/1970 | Pierie et al. | 606/207 |
| 3,503,398 A * | 3/1970 | Raible et al. | 606/207 |
| 3,552,626 A | 1/1971 | Astafiev et al. | |
| 3,568,659 A | 3/1971 | Karnegis | |
| 3,589,589 A | 6/1971 | Akopov | |
| 3,593,903 A | 7/1971 | Astafiev et al. | |
| 3,618,842 A | 11/1971 | Bryan | |
| 3,638,652 A | 2/1972 | Kelley | |
| 3,643,851 A | 2/1972 | Green et al. | |
| 3,662,939 A * | 5/1972 | Bryan | 227/19 |
| 3,675,688 A | 7/1972 | Bryan et al. | |
| 3,692,224 A | 9/1972 | Astafiev et al. | |
| 3,717,294 A | 2/1973 | Green | |
| 3,735,762 A | 5/1973 | Bryan et al. | |
| 3,777,538 A | 12/1973 | Weatherly et al. | |
| 3,788,303 A | 1/1974 | Hall | |
| 3,795,034 A | 3/1974 | Strekopytov et al. | |
| 3,815,476 A | 6/1974 | Green et al. | |
| 3,819,100 A | 6/1974 | Noiles et al. | |
| 3,837,555 A | 9/1974 | Green | |
| 3,844,289 A | 10/1974 | Noiles | |
| 2,859,986 A | 1/1975 | Okada et al. | |
| 3,858,577 A | 1/1975 | Bass et al. | |
| 3,882,854 A | 5/1975 | Hulka et al. | |
| 3,892,228 A | 7/1975 | Mitsui | |
| 3,935,981 A | 2/1976 | Akopov et al. | |
| 3,949,924 A | 4/1976 | Green | |
| 3,952,748 A | 4/1976 | Kaliher et al. | |
| RE28,932 E | 8/1976 | Noiles et al. | |
| 4,014,492 A | 3/1977 | Rothfuss | |
| 4,027,510 A | 6/1977 | Hiltebrandt | |
| 4,060,089 A | 11/1977 | Noiles | |
| 4,064,881 A | 12/1977 | Meredith | |
| 4,071,029 A | 1/1978 | Richmond et al. | |
| 4,085,756 A | 4/1978 | Weaver | |
| 4,086,926 A | 5/1978 | Green et al. | |
| 4,092,986 A | 6/1978 | Schneiderman | |
| 4,111,206 A | 9/1978 | Vishnevsky et al. | |
| 4,169,476 A | 10/1979 | Hiltebrandt | |
| 4,198,960 A | 4/1980 | Utsugi | |
| 4,198,982 A | 4/1980 | Fortner et al. | |
| 4,202,479 A | 5/1980 | Razgulov et al. | |
| 4,202,480 A | 5/1980 | Annett | |
| 4,207,873 A | 6/1980 | Kruy | |
| 4,207,898 A | 6/1980 | Becht | |
| 4,226,240 A * | 10/1980 | Walker, Jr. | 606/207 |
| 4,226,241 A * | 10/1980 | Walker, Jr. | 606/207 |
| 4,244,372 A | 1/1981 | Kapitanov et al. | |
| 4,261,244 A | 4/1981 | Becht et al. | |
| 4,273,111 A | 6/1981 | Tsukaya | |
| 4,273,129 A | 6/1981 | Boebel | |
| 4,286,585 A | 9/1981 | Ogawa | |
| 4,286,598 A * | 9/1981 | Kapitanov et al. | 606/207 |
| 4,289,131 A | 9/1981 | Mueller | |
| 4,289,133 A | 9/1981 | Rothfuss | |
| 4,296,881 A | 10/1981 | Lee | |
| 4,304,236 A | 12/1981 | Conta et al. | |
| 4,310,115 A | 1/1982 | Inoue | |
| 4,319,576 A | 3/1982 | Rothfuss | |
| 4,325,377 A | 4/1982 | Boebel | |
| 4,334,539 A | 6/1982 | Childs et al. | |
| 4,349,028 A | 9/1982 | Green | |
| 4,351,466 A | 9/1982 | Noiles | |
| 4,354,628 A | 10/1982 | Green | |
| 4,367,729 A | 1/1983 | Ogiu | |
| 4,379,457 A | 4/1983 | Gravener et al. | |
| 4,383,634 A | 5/1983 | Green | |
| 4,391,401 A | 7/1983 | Moshofsky | |
| 4,402,311 A | 9/1983 | Hattori | |
| 4,402,445 A | 9/1983 | Green | |
| 4,429,695 A | 2/1984 | Green | |
| 4,442,964 A | 4/1984 | Becht | |
| 4,445,509 A | 5/1984 | Auth | |
| 4,445,892 A | 5/1984 | Hussein et al. | |
| 4,448,188 A | 5/1984 | Loeb | |
| 4,461,305 A | 7/1984 | Cibley | |
| 4,473,077 A | 9/1984 | Noiles et al. | |
| 4,476,863 A | 10/1984 | Kanshin et al. | |
| 4,485,811 A | 12/1984 | Chernousov et al. | |
| 4,485,817 A | 12/1984 | Swiggett | |
| 4,487,270 A | 12/1984 | Huber | |
| 4,488,523 A | 12/1984 | Shichman | |
| 4,489,724 A | 12/1984 | Arnegger | |
| 4,489,875 A | 12/1984 | Crawford et al. | |
| 4,494,057 A | 1/1985 | Hotta | |
| 4,494,549 A | 1/1985 | Namba et al. | |
| 4,499,895 A | 2/1985 | Takayama | |
| 4,505,272 A | 3/1985 | Utyamyshev et al. | |
| 4,505,414 A | 3/1985 | Filipi | |
| 4,506,670 A | 3/1985 | Crossley | |
| 4,506,671 A | 3/1985 | Green | |
| 4,513,746 A | 4/1985 | Aranyi et al. | |
| 4,519,532 A | 5/1985 | Foslien | |
| 4,520,817 A | 6/1985 | Green | |
| 4,534,352 A | 8/1985 | Korthoff | |
| 4,534,420 A | 8/1985 | Goldelius | |
| 4,535,773 A | 8/1985 | Yoon | |
| 4,559,928 A | 12/1985 | Takayama | |
| 4,566,620 A | 1/1986 | Green et al. | |
| 4,573,468 A | 3/1986 | Conta et al. | |
| 4,573,622 A | 3/1986 | Green et al. | |
| 4,574,806 A | 3/1986 | McCarthy | |
| 4,576,167 A | 3/1986 | Noiles | |
| 4,589,412 A | 5/1986 | Kensey | |
| 4,589,416 A | 5/1986 | Green | |
| 4,589,582 A | 5/1986 | Bilotti | |
| 4,591,085 A | 5/1986 | Di Giovanni | |
| 4,592,354 A | 6/1986 | Rothfuss | |
| 4,593,679 A | 6/1986 | Collins | |
| 4,603,693 A | 8/1986 | Conta et al. | |
| 4,605,001 A | 8/1986 | Rothfuss et al. | |
| 4,606,343 A | 8/1986 | Conta et al. | |
| 4,607,638 A | 8/1986 | Crainich | |
| 4,610,383 A * | 9/1986 | Rothfuss et al. | 227/19 |
| D286,567 S | 11/1986 | Lichtman et al. | |
| 4,631,052 A | 12/1986 | Kensey | |
| 4,633,861 A | 1/1987 | Chow et al. | |
| 4,633,874 A | 1/1987 | Chow et al. | |
| 4,643,190 A | 2/1987 | Heimberger | |
| 4,644,952 A | 2/1987 | Patipa et al. | |
| 4,646,745 A | 3/1987 | Noiles | |
| 4,655,673 A | 4/1987 | Hawkes | |
| 4,657,017 A | 4/1987 | Sorochenko | |
| 4,664,305 A | 5/1987 | Blake, III et al. | |
| 4,667,673 A | 5/1987 | Li | |
| 4,669,471 A | 6/1987 | Hayashi | |
| 4,671,445 A | 6/1987 | Barker et al. | |
| 4,672,961 A | 6/1987 | Davies | |
| 4,674,515 A | 6/1987 | Andou et al. | |
| 4,688,555 A | 8/1987 | Wardle | |
| 4,696,667 A | 9/1987 | Masch | |
| 4,700,703 A | 10/1987 | Resnick et al. | |
| 4,703,887 A | 11/1987 | Clanton et al. | |

(56) References Cited

U.S. PATENT DOCUMENTS

| | | | |
|---|---|---|---|
| 4,705,038 A | 11/1987 | Sjostrom et al. | |
| 4,708,141 A | 11/1987 | Inoue et al. | |
| 4,714,187 A | 12/1987 | Green | |
| 4,715,502 A | 12/1987 | Salmon | |
| 1,732,156 A | 3/1988 | Nakamura | |
| 4,728,020 A | 3/1988 | Green et al. | |
| 4,733,118 A | 3/1988 | Mihalko | |
| 4,742,815 A | 5/1988 | Ninan et al. | |
| 4,752,024 A | 6/1988 | Green et al. | |
| 4,754,909 A | 7/1988 | Barker et al. | |
| 4,756,309 A | 7/1988 | Sachse et al. | |
| 4,760,840 A | 8/1988 | Fournier, Jr. et al. | |
| 4,763,669 A | 8/1988 | Jaeger | |
| 4,767,044 A | 8/1988 | Green | |
| 4,771,774 A | 9/1988 | Simpson et al. | |
| 4,776,506 A | 10/1988 | Green | |
| 4,781,186 A | 11/1988 | Simpson et al. | |
| 4,784,137 A | 11/1988 | Kulik et al. | |
| 4,789,090 A | 12/1988 | Blake, III | |
| 4,796,793 A | 1/1989 | Smith et al. | |
| 4,805,823 A | 2/1989 | Rothfuss | |
| 4,815,469 A | 3/1989 | Cohen et al. | |
| 4,817,847 A | 4/1989 | Redtenbacher et al. | |
| 4,819,632 A | 4/1989 | Davies | |
| 4,819,853 A | 4/1989 | Green | |
| 4,841,888 A | 6/1989 | Mills et al. | |
| 4,848,637 A | 7/1989 | Pruitt | |
| 4,858,608 A | 8/1989 | McQuilkin | |
| 4,863,088 A | 9/1989 | Redmond et al. | |
| 4,867,158 A | 9/1989 | Sugg | |
| 4,869,415 A | 9/1989 | Fox | |
| 4,873,977 A | 10/1989 | Avant et al. | |
| 4,887,599 A | 12/1989 | Muller | |
| 4,887,612 A | 12/1989 | Esser et al. | |
| 4,890,602 A | 1/1990 | Hake | |
| 4,892,244 A | 1/1990 | Fox et al. | |
| 4,893,613 A | 1/1990 | Hake | |
| 4,893,622 A | 1/1990 | Green et al. | |
| 4,903,697 A | 2/1990 | Resnick et al. | |
| 4,907,591 A | 3/1990 | Vasconcellos et al. | |
| 4,917,114 A | 4/1990 | Green et al. | |
| 4,919,152 A | 4/1990 | Ger | |
| 4,928,699 A | 5/1990 | Sasai | |
| 4,930,494 A | 6/1990 | Takehana et al. | |
| 4,932,960 A | 6/1990 | Green et al. | |
| 4,936,845 A | 6/1990 | Stevens | |
| 4,941,454 A | 7/1990 | Wood et al. | |
| 4,941,623 A * | 7/1990 | Pruitt | 227/19 |
| 4,944,093 A | 7/1990 | Falk | |
| 4,944,443 A | 7/1990 | Oddsen et al. | |
| 4,955,882 A | 9/1990 | Hakky | |
| 4,955,959 A | 9/1990 | Tompkins et al. | |
| 4,957,499 A | 9/1990 | Lipatov et al. | |
| 4,962,877 A | 10/1990 | Hervas | |
| 4,976,688 A | 12/1990 | Rosenblum | |
| 4,976,710 A | 12/1990 | Mackin | |
| 4,977,900 A | 12/1990 | Fehling et al. | |
| 4,978,049 A | 12/1990 | Green | |
| 4,982,726 A | 1/1991 | Taira | |
| 4,991,764 A | 2/1991 | Mericle | |
| 4,994,060 A | 2/1991 | Rink et al. | |
| 4,995,877 A | 2/1991 | Ams et al. | |
| 5,005,749 A * | 4/1991 | Aranyi | 227/19 |
| 5,018,657 A | 5/1991 | Pedlick et al. | |
| 5,031,814 A | 7/1991 | Tompkins et al. | |
| 5,040,715 A * | 8/1991 | Green et al. | 227/176.1 |
| 5,059,203 A | 10/1991 | Husted | |
| 5,065,929 A | 11/1991 | Schulze et al. | |
| D322,143 S | 12/1991 |Spreckelmeier | |
| 5,071,430 A * | 12/1991 | de Salis et al. | 606/219 |
| 5,077,506 A | 12/1991 | Krause | |
| 5,100,041 A | 3/1992 | Storace | |
| 5,100,042 A | 3/1992 | Gravener et al. | |
| 5,104,025 A | 4/1992 | Main et al. | |
| 5,108,391 A | 4/1992 | Flachenecker et al. | |
| 5,114,065 A | 5/1992 | Storace | |
| 5,119,983 A | 6/1992 | Green et al. | |
| 5,129,570 A | 7/1992 | Schulze et al. | |
| 5,133,359 A | 7/1992 | Kedem | |
| 5,133,713 A | 7/1992 | Huang et al. | |
| 5,137,198 A * | 8/1992 | Nobis et al. | 227/175.3 |
| 5,139,513 A | 8/1992 | Segato | |
| 5,156,315 A | 10/1992 | Green et al. | |
| 5,157,837 A | 10/1992 | Rose | |
| 5,158,222 A | 10/1992 | Green et al. | |
| 5,170,925 A | 12/1992 | Madden et al. | |
| 5,171,247 A | 12/1992 | Hughett et al. | |
| 5,171,251 A | 12/1992 | Bregen et al. | |
| 5,173,133 A | 12/1992 | Morin et al. | |
| 5,190,203 A * | 3/1993 | Rodak | 227/175.1 |
| 5,192,292 A | 3/1993 | Cezana et al. | |
| 5,197,649 A | 3/1993 | Bessler et al. | |
| 5,201,325 A | 4/1993 | McEwen et al. | |
| 5,201,750 A | 4/1993 | Hocherl et al. | |
| 5,205,459 A | 4/1993 | Brinkerhoff et al. | |
| 5,207,691 A | 5/1993 | Nardella | |
| 5,207,697 A | 5/1993 | Carusillo et al. | |
| 5,217,003 A | 6/1993 | Wilk | |
| 5,217,460 A | 6/1993 | Knoepfler | |
| 5,219,111 A * | 6/1993 | Bilotti et al. | 227/175.1 |
| 5,221,279 A | 6/1993 | Cook et al. | |
| 5,224,951 A | 7/1993 | Freitas | |
| 5,226,426 A | 7/1993 | Yoon | |
| 5,237,884 A | 8/1993 | Seto | |
| 5,243,967 A | 9/1993 | Hibino | |
| 5,249,583 A | 10/1993 | Mallaby | |
| 5,250,072 A * | 10/1993 | Jain | 606/205 |
| 5,250,074 A * | 10/1993 | Wilk et al. | 606/207 |
| 5,253,793 A | 10/1993 | Green et al. | |
| 5,254,117 A | 10/1993 | Rigby et al. | |
| 5,258,004 A | 11/1993 | Bales et al. | |
| 5,258,007 A | 11/1993 | Spetzler et al. | |
| 5,258,008 A | 11/1993 | Wilk | |
| 5,261,877 A | 11/1993 | Fine et al. | |
| 5,267,997 A | 12/1993 | Farin et al. | |
| 5,268,622 A | 12/1993 | Philipp | |
| 5,271,543 A | 12/1993 | Grant et al. | |
| 5,271,544 A | 12/1993 | Fox et al. | |
| RE34,519 E | 1/1994 | Fox et al. | |
| 5,275,322 A | 1/1994 | Brinkerhoff et al. | |
| 5,275,323 A | 1/1994 | Schulze et al. | |
| 5,275,609 A | 1/1994 | Pingleton et al. | |
| 5,279,565 A | 1/1994 | Klein et al. | |
| 5,282,826 A * | 2/1994 | Quadri | 606/207 |
| 5,285,945 A | 2/1994 | Brinkerhoff et al. | |
| 5,289,963 A * | 3/1994 | McGarry et al. | 227/175.1 |
| 5,290,299 A | 3/1994 | Fain et al. | |
| 5,290,303 A | 3/1994 | Pingleton et al. | |
| 5,292,053 A | 3/1994 | Bilotti et al. | |
| 5,295,990 A | 3/1994 | Levin | |
| 5,300,087 A | 4/1994 | Knoepfler | |
| 5,307,976 A | 5/1994 | Olson et al. | |
| 5,312,023 A | 5/1994 | Green et al. | |
| 5,312,434 A | 5/1994 | Crainich | |
| 5,314,436 A | 5/1994 | Wilk | |
| 5,318,221 A | 6/1994 | Green et al. | |
| 5,320,627 A | 6/1994 | Sorensen et al. | |
| 5,322,055 A | 6/1994 | Davison et al. | |
| 5,324,288 A | 6/1994 | Billings et al. | |
| 5,324,300 A | 6/1994 | Elias et al. | |
| 5,326,013 A * | 7/1994 | Green et al. | 227/176.1 |
| 5,328,077 A * | 7/1994 | Lou | 227/175.1 |
| 5,330,471 A | 7/1994 | Eggers | |
| 5,330,486 A | 7/1994 | Wilk | |
| 5,333,772 A | 8/1994 | Rothfuss et al. | |
| 5,333,773 A | 8/1994 | Main et al. | |
| 5,336,229 A | 8/1994 | Noda | |
| 5,342,299 A | 8/1994 | Snoke et al. | |
| 5,342,381 A | 8/1994 | Tidemand | |
| 5,342,382 A | 8/1994 | Brinkerhoff et al. | |
| 5,344,420 A | 9/1994 | Hilal et al. | |
| 5,350,104 A | 9/1994 | Main et al. | |
| 5,352,222 A | 10/1994 | Rydell | |
| 5,352,223 A | 10/1994 | McBrayer et al. | |

(56) References Cited

U.S. PATENT DOCUMENTS

| | | | |
|---|---|---|---|
| 5,352,235 A | 10/1994 | Koros et al. | |
| 5,354,266 A | 10/1994 | Snoke | |
| 5,356,408 A | 10/1994 | Rydell | |
| 5,358,506 A | 10/1994 | Green et al. | |
| 5,364,001 A | 11/1994 | Bryan | |
| 5,364,409 A | 11/1994 | Kuwabara et al. | |
| 5,366,133 A | 11/1994 | Geiste | |
| 5,366,476 A | 11/1994 | Noda | |
| 5,368,015 A | 11/1994 | Wilk | |
| 5,368,599 A * | 11/1994 | Hirsch et al. | 606/139 |
| 5,368,607 A | 11/1994 | Freitas | |
| 5,380,321 A | 1/1995 | Yoon | |
| 5,383,880 A * | 1/1995 | Hooven | 606/142 |
| 5,389,098 A | 2/1995 | Tsuruta et al. | |
| 5,391,156 A | 2/1995 | Hildwein et al. | |
| 5,392,978 A | 2/1995 | Velez et al. | |
| 5,395,030 A | 3/1995 | Kuramoto et al. | |
| 5,395,033 A * | 3/1995 | Byrne et al. | 227/175.1 |
| 5,395,369 A | 3/1995 | McBrayer et al. | |
| 5,396,900 A | 3/1995 | Slater et al. | |
| 5,397,046 A | 3/1995 | Savage et al. | |
| 5,400,267 A | 3/1995 | Denen et al. | |
| D357,535 S | 4/1995 | Grant et al. | |
| 5,403,312 A | 4/1995 | Yates et al. | |
| 5,403,326 A | 4/1995 | Harrison et al. | |
| 5,403,327 A | 4/1995 | Thornton et al. | |
| 5,405,073 A * | 4/1995 | Porter | 227/175.1 |
| 5,405,244 A | 4/1995 | Boyd | |
| 5,411,508 A | 5/1995 | Bessler et al. | |
| 5,413,267 A | 5/1995 | Solyntjes et al. | |
| 5,413,268 A | 5/1995 | Green et al. | |
| 5,415,334 A | 5/1995 | Williamson et al. | |
| 5,425,705 A | 6/1995 | Evard et al. | |
| 5,425,738 A | 6/1995 | Gustafson et al. | |
| 5,425,745 A | 6/1995 | Green et al. | |
| 5,431,322 A | 7/1995 | Green et al. | |
| 5,431,645 A | 7/1995 | Smith et al. | |
| 5,433,721 A * | 7/1995 | Hooven et al. | 606/143 |
| 5,437,636 A | 8/1995 | Snoke et al. | |
| 5,437,684 A * | 8/1995 | Calabrese et al. | 606/153 |
| 5,441,507 A | 8/1995 | Wilk | |
| 5,443,198 A * | 8/1995 | Viola et al. | 227/179.1 |
| 5,447,265 A | 9/1995 | Vidal et al. | |
| 5,454,825 A | 10/1995 | Van Leeuwen et al. | |
| 5,456,684 A | 10/1995 | Schmidt et al. | |
| 5,460,182 A | 10/1995 | Goodman et al. | |
| 5,464,404 A | 11/1995 | Abela et al. | |
| 5,465,894 A * | 11/1995 | Clark et al. | 227/175.1 |
| 5,467,911 A | 11/1995 | Tsuruta et al. | |
| 5,468,250 A | 11/1995 | Paraschac et al. | |
| 5,472,132 A | 12/1995 | Savage et al. | |
| 5,474,223 A | 12/1995 | Viola et al. | |
| 5,476,206 A | 12/1995 | Green et al. | |
| 5,482,054 A | 1/1996 | Slater et al. | |
| 5,482,197 A | 1/1996 | Green et al. | |
| 5,485,947 A | 1/1996 | Olson et al. | |
| 5,487,499 A | 1/1996 | Sorrentino et al. | |
| 5,487,500 A | 1/1996 | Knodel et al. | |
| 5,496,269 A | 3/1996 | Snoke | |
| 5,496,317 A | 3/1996 | Goble et al. | |
| 5,514,134 A | 5/1996 | Rydell et al. | |
| 5,518,163 A * | 5/1996 | Hooven | 227/5 |
| 5,518,164 A | 5/1996 | Hooven | |
| 5,520,634 A | 5/1996 | Fox et al. | |
| 5,524,180 A | 6/1996 | Wang et al. | |
| 5,527,313 A | 6/1996 | Scott et al. | |
| 5,529,235 A | 6/1996 | Boiarski et al. | |
| 5,531,687 A | 7/1996 | Snoke et al. | |
| 5,533,661 A | 7/1996 | Main et al. | |
| 5,535,937 A | 7/1996 | Boiarski et al. | |
| 5,549,565 A | 8/1996 | Ryan et al. | |
| 5,553,765 A | 9/1996 | Knodel et al. | |
| 5,554,169 A | 9/1996 | Green et al. | |
| 5,558,266 A * | 9/1996 | Green et al. | 227/178.1 |
| 5,562,677 A | 10/1996 | Hildwein et al. | |
| 5,562,702 A | 10/1996 | Huitema et al. | |
| 5,569,274 A | 10/1996 | Rapacki et al. | |
| 5,569,289 A | 10/1996 | Yoon | |
| 5,571,116 A | 11/1996 | Bolanos et al. | |
| 5,573,543 A | 11/1996 | Akopov et al. | |
| 5,578,052 A | 11/1996 | Koros et al. | |
| 5,580,067 A | 12/1996 | Hamblin et al. | |
| 5,582,611 A | 12/1996 | Tsuruta et al. | |
| 5,584,425 A | 12/1996 | Savage et al. | |
| 5,588,579 A | 12/1996 | Schnut et al. | |
| 5,591,186 A | 1/1997 | Wurster et al. | |
| 5,591,196 A | 1/1997 | Marin et al. | |
| 5,597,107 A | 1/1997 | Knodel et al. | |
| 5,599,347 A | 2/1997 | Hart et al. | |
| 5,603,443 A | 2/1997 | Clark et al. | |
| 5,607,094 A | 3/1997 | Clark et al. | |
| 5,609,285 A | 3/1997 | Grant et al. | |
| 5,609,560 A | 3/1997 | Ichikawa et al. | |
| 5,618,303 A | 4/1997 | Marlow et al. | |
| 5,618,307 A | 4/1997 | Donlon et al. | |
| 5,626,607 A | 5/1997 | Malecki et al. | |
| 5,639,008 A | 6/1997 | Gallagher et al. | |
| 5,641,111 A * | 6/1997 | Ahrens et al. | 227/175.1 |
| 5,651,780 A | 7/1997 | Jackson et al. | |
| 5,653,374 A * | 8/1997 | Young et al. | 227/176.1 |
| 5,657,921 A * | 8/1997 | Young et al. | 227/176.1 |
| 5,665,100 A | 9/1997 | Yoon | |
| 5,667,473 A | 9/1997 | Finn et al. | |
| 5,667,478 A | 9/1997 | McFarlin et al. | |
| 5,667,517 A * | 9/1997 | Hooven | 606/151 |
| 5,667,526 A | 9/1997 | Levin | |
| 5,676,674 A | 10/1997 | Bolanos et al. | |
| 5,688,269 A | 11/1997 | Newton et al. | |
| 5,692,668 A | 12/1997 | Schulze et al. | |
| 5,693,031 A | 12/1997 | Ryan et al. | |
| 5,702,408 A | 12/1997 | Wales et al. | |
| 5,704,534 A * | 1/1998 | Huitema et al. | 227/175.1 |
| 5,709,335 A | 1/1998 | Heck | |
| 5,711,472 A | 1/1998 | Bryan | |
| 5,725,536 A | 3/1998 | Oberlin et al. | |
| 5,732,871 A | 3/1998 | Clark et al. | |
| 5,732,872 A | 3/1998 | Bolduc et al. | |
| 5,735,848 A | 4/1998 | Yates et al. | |
| 5,735,849 A | 4/1998 | Baden et al. | |
| 5,735,861 A | 4/1998 | Peifer et al. | |
| 5,741,285 A | 4/1998 | McBrayer et al. | |
| 5,749,885 A | 5/1998 | Sjostrom et al. | |
| 5,749,893 A | 5/1998 | Vidal et al. | |
| 5,752,644 A | 5/1998 | Bolanos et al. | |
| 5,758,814 A | 6/1998 | Gallagher et al. | |
| 5,762,256 A * | 6/1998 | Mastri et al. | 227/176.1 |
| 5,762,458 A | 6/1998 | Wang et al. | |
| 5,779,130 A | 7/1998 | Alesi et al. | |
| 5,782,396 A | 7/1998 | Mastri et al. | |
| 5,782,397 A | 7/1998 | Koukline | |
| 5,792,135 A | 8/1998 | Madhani et al. | |
| 5,792,165 A | 8/1998 | Klieman et al. | |
| 5,797,536 A * | 8/1998 | Smith et al. | 227/175.1 |
| 5,797,835 A | 8/1998 | Green | |
| 5,797,900 A | 8/1998 | Madhani et al. | |
| 5,797,944 A | 8/1998 | Nobles et al. | |
| 5,807,377 A | 9/1998 | Madhani et al. | |
| 5,807,402 A | 9/1998 | Yoon | |
| 5,814,044 A | 9/1998 | Hooven | |
| 5,815,640 A | 9/1998 | Wang et al. | |
| 5,817,113 A | 10/1998 | Gifford, III et al. | |
| 5,817,119 A | 10/1998 | Klieman et al. | |
| 5,823,956 A | 10/1998 | Roth et al. | |
| 5,826,776 A | 10/1998 | Schulze et al. | |
| 5,829,662 A | 11/1998 | Allen et al. | |
| 5,836,503 A | 11/1998 | Ehrenfels et al. | |
| 5,846,221 A | 12/1998 | Snoke et al. | |
| 5,855,583 A | 1/1999 | Wang et al. | |
| 5,855,590 A | 1/1999 | Malecki et al. | |
| 5,857,996 A | 1/1999 | Snoke | |
| 5,860,953 A | 1/1999 | Snoke et al. | |
| 5,868,760 A | 2/1999 | McGuckin, Jr. | |
| 5,871,471 A | 2/1999 | Ryan et al. | |
| 5,878,193 A | 3/1999 | Wang et al. | |

(56) References Cited

U.S. PATENT DOCUMENTS

| | | |
|---|---|---|
| 5,881,943 A | 3/1999 | Heck et al. |
| 5,893,875 A | 4/1999 | O'Connor et al. |
| 5,897,507 A * | 4/1999 | Kortenbach et al. ......... 600/562 |
| 5,897,562 A | 4/1999 | Bolanos et al. |
| 5,901,895 A | 5/1999 | Heaton et al. |
| 5,907,664 A | 5/1999 | Wang et al. |
| 5,913,842 A | 6/1999 | Boyd et al. |
| 5,915,616 A | 6/1999 | Viola et al. |
| 5,925,055 A | 7/1999 | Adrian et al. |
| 5,931,848 A | 8/1999 | Saadat |
| 5,947,363 A | 9/1999 | Bolduc et al. |
| 5,951,549 A | 9/1999 | Richardson et al. |
| 5,954,259 A * | 9/1999 | Viola et al. ................. 227/176.1 |
| 5,957,363 A | 9/1999 | Heck |
| 5,957,882 A | 9/1999 | Nita et al. |
| 5,957,884 A | 9/1999 | Hooven |
| 5,976,159 A | 11/1999 | Bolduc et al. |
| 5,984,919 A | 11/1999 | Hilal et al. |
| 5,989,215 A | 11/1999 | Delmotte et al. |
| 5,993,378 A | 11/1999 | Lemelson |
| 5,993,454 A | 11/1999 | Longo |
| 5,997,510 A | 12/1999 | Schwemberger |
| 6,001,108 A | 12/1999 | Wang et al. |
| 6,004,335 A | 12/1999 | Vaitekunas et al. |
| 6,007,512 A | 12/1999 | Hooven |
| 6,007,531 A | 12/1999 | Snoke et al. |
| 6,010,054 A | 1/2000 | Johnson et al. |
| 6,010,493 A | 1/2000 | Snoke |
| 6,017,322 A | 1/2000 | Snoke et al. |
| 6,017,354 A | 1/2000 | Culp et al. |
| 6,024,741 A | 2/2000 | Williamson, IV et al. |
| 6,063,095 A | 5/2000 | Wang et al. |
| 6,068,627 A | 5/2000 | Orszulak et al. |
| 6,074,402 A | 6/2000 | Peifer et al. |
| 6,083,163 A | 7/2000 | Wegner et al. |
| 6,086,600 A | 7/2000 | Kortenbach |
| 6,090,120 A | 7/2000 | Wright et al. |
| 6,099,466 A | 8/2000 | Sano et al. |
| 6,106,512 A | 8/2000 | Cochran et al. |
| 6,110,188 A | 8/2000 | Narciso, Jr. |
| 6,119,913 A | 9/2000 | Adams et al. |
| 6,126,058 A | 10/2000 | Adams et al. |
| 6,126,591 A | 10/2000 | McGarry et al. |
| 6,132,368 A | 10/2000 | Cooper |
| 6,162,220 A | 12/2000 | Nezhat |
| 6,165,191 A | 12/2000 | Shibata et al. |
| 6,174,324 B1 | 1/2001 | Egan et al. |
| 6,179,837 B1 | 1/2001 | Hooven |
| 6,193,129 B1 | 2/2001 | Bittner et al. |
| D438,617 S | 3/2001 | Cooper et al. |
| 6,201,984 B1 | 3/2001 | Funda et al. |
| 6,206,903 B1 | 3/2001 | Ramans |
| D441,076 S | 4/2001 | Cooper et al. |
| 6,209,773 B1 | 4/2001 | Bolduc et al. |
| 6,217,591 B1 | 4/2001 | Egan et al. |
| D441,862 S | 5/2001 | Cooper et al. |
| 6,231,587 B1 | 5/2001 | Makower |
| 6,238,414 B1 * | 5/2001 | Griffiths ................ 606/205 |
| 6,241,139 B1 * | 6/2001 | Milliman et al. ......... 227/175.1 |
| 6,244,809 B1 | 6/2001 | Wang et al. |
| 6,246,200 B1 | 6/2001 | Blumenkranz et al. |
| D444,555 S | 7/2001 | Cooper et al. |
| 6,264,087 B1 | 7/2001 | Whitman |
| 6,270,508 B1 * | 8/2001 | Klieman et al. ............ 606/147 |
| 6,279,508 B1 | 8/2001 | Marchant et al. |
| 6,309,397 B1 | 10/2001 | Julian et al. |
| 6,312,435 B1 | 11/2001 | Wallace et al. |
| 6,315,184 B1 | 11/2001 | Whitman |
| 6,331,181 B1 | 12/2001 | Tierney et al. |
| 6,346,072 B1 | 2/2002 | Cooper |
| 6,348,061 B1 | 2/2002 | Whitman |
| 6,364,888 B1 | 4/2002 | Niemeyer et al. |
| 6,368,340 B2 | 4/2002 | Malecki et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,443,973 B1 * | 9/2002 | Whitman ...................... 606/219 |
| 6,488,197 B1 | 12/2002 | Whitman |
| 6,491,201 B1 | 12/2002 | Whitman |
| 6,505,768 B2 | 1/2003 | Whitman |
| 6,517,565 B1 * | 2/2003 | Whitman et al. ............. 606/219 |
| 6,533,157 B1 | 3/2003 | Whitman |
| 6,685,715 B2 * | 2/2004 | Danitz et al. .................. 606/157 |
| 6,790,217 B2 | 9/2004 | Schulze et al. |
| 6,793,652 B1 * | 9/2004 | Whitman et al. ................. 606/1 |
| 6,981,941 B2 * | 1/2006 | Whitman et al. ................. 600/1 |
| 7,032,798 B2 * | 4/2006 | Whitman et al. ........... 227/175.1 |
| 8,016,855 B2 * | 9/2011 | Whitman et al. ............. 606/205 |
| 8,518,074 B2 * | 8/2013 | Whitman et al. ............. 606/205 |
| 2001/0016750 A1 | 8/2001 | Malecki et al. |
| 2001/0030219 A1 * | 10/2001 | Green et al. ............. 227/175.1 |
| 2001/0031975 A1 | 10/2001 | Whitman et al. |
| 2002/0032451 A1 | 3/2002 | Tierney et al. |
| 2002/0032452 A1 | 3/2002 | Tierney et al. |
| 2002/0042620 A1 | 4/2002 | Julian et al. |
| 2002/0045888 A1 | 4/2002 | Ramans et al. |
| 2002/0049454 A1 | 4/2002 | Whitman et al. |
| 2002/0055795 A1 | 5/2002 | Niemeyer et al. |
| 2002/0072736 A1 | 6/2002 | Tierney et al. |
| 2002/0165444 A1 | 11/2002 | Whitman |
| 2003/0105478 A1 | 6/2003 | Whitman et al. |
| 2003/0130677 A1 | 7/2003 | Whitman et al. |
| 2008/0234725 A1 * | 9/2008 | Griffiths et al. ............... 606/208 |

FOREIGN PATENT DOCUMENTS

| | | |
|---|---|---|
| DE | 2903159 A1 | 7/1980 |
| DE | 3114135 A1 | 10/1982 |
| DE | 3300768 A1 | 7/1984 |
| DE | 4213426 A1 | 10/1992 |
| DE | 4312147 A1 | 10/1993 |
| EP | 0041022 A1 | 12/1981 |
| EP | 0116220 A1 | 8/1984 |
| EP | 0121474 A2 | 10/1984 |
| EP | 0142225 A1 | 5/1985 |
| EP | 0156774 A2 | 10/1985 |
| EP | 0203375 A2 | 12/1986 |
| EP | 0216532 A1 | 4/1987 |
| EP | 0293123 A2 | 11/1988 |
| EP | 0324166 A2 | 7/1989 |
| EP | 0324637 A1 | 7/1989 |
| EP | 0365153 A1 | 4/1990 |
| EP | 0369324 A1 | 5/1990 |
| EP | 0373762 A1 | 6/1990 |
| EP | 0399701 A1 | 11/1990 |
| EP | 0484677 A1 | 5/1992 |
| EP | 0514139 A2 | 11/1992 |
| EP | 0536903 A2 | 4/1993 |
| EP | 0539762 A1 | 5/1993 |
| EP | 0552050 A2 | 7/1993 |
| EP | 0552423 A2 | 7/1993 |
| EP | 0581400 A1 | 2/1994 |
| EP | 0593920 A1 | 4/1994 |
| EP | 0598579 A1 | 5/1994 |
| EP | 0621006 A1 | 10/1994 |
| EP | 0630612 A1 | 12/1994 |
| EP | 0634144 A1 | 1/1995 |
| EP | 0639349 A2 | 2/1995 |
| EP | 0648476 A1 | 4/1995 |
| EP | 0653922 A1 | 5/1995 |
| EP | 0679367 A2 | 11/1995 |
| EP | 0705571 A1 | 4/1996 |
| EP | 0 648 476 B1 | 1/1998 |
| EP | 0878169 A1 | 11/1998 |
| EP | 0947167 A1 | 10/1999 |
| FR | 2660851 A1 | 10/1991 |
| GB | 1082821 A | 9/1967 |
| GB | 1352554 A | 5/1974 |
| GB | 1452185 A | 10/1976 |
| GB | 2048685 A | 12/1980 |
| GB | 2165559 A | 4/1986 |
| GB | 2180455 A | 4/1987 |
| NL | 7711347 A | 4/1979 |
| SU | 659146 A1 | 4/1979 |

(56) References Cited

FOREIGN PATENT DOCUMENTS

| | | | |
|---|---|---|---|
| WO | 8203545 | A1 | 10/1982 |
| WO | 90/05489 | A1 | 5/1990 |
| WO | 9005491 | A2 | 5/1990 |
| WO | 9006085 | A1 | 6/1990 |
| WO | 9107136 | A1 | 5/1991 |
| WO | 9216141 | A1 | 10/1992 |
| WO | 9308754 | A1 | 5/1993 |
| WO | 9314706 | A1 | 8/1993 |
| WO | 9518572 | A1 | 7/1995 |
| WO | 9535065 | A1 | 12/1995 |
| WO | 9712555 | A2 | 4/1997 |
| WO | 9814129 | A1 | 4/1998 |
| WO | 9920328 | A2 | 4/1999 |
| WO | 9958076 | A1 | 11/1999 |
| WO | 0072765 | A1 | 12/2000 |
| WO | WO 00/72765 | | 12/2000 |
| WO | 0103587 | A1 | 1/2001 |
| WO | 0108572 | A1 | 2/2001 |
| WO | 01/17448 | | 3/2001 |
| WO | 0135813 | A1 | 5/2001 |
| WO | 0162163 | A1 | 8/2001 |
| WO | 0191646 | A1 | 12/2001 |
| WO | WO 01/91646 | A1 | 12/2001 |
| WO | 02058539 | A2 | 8/2002 |

\* cited by examiner

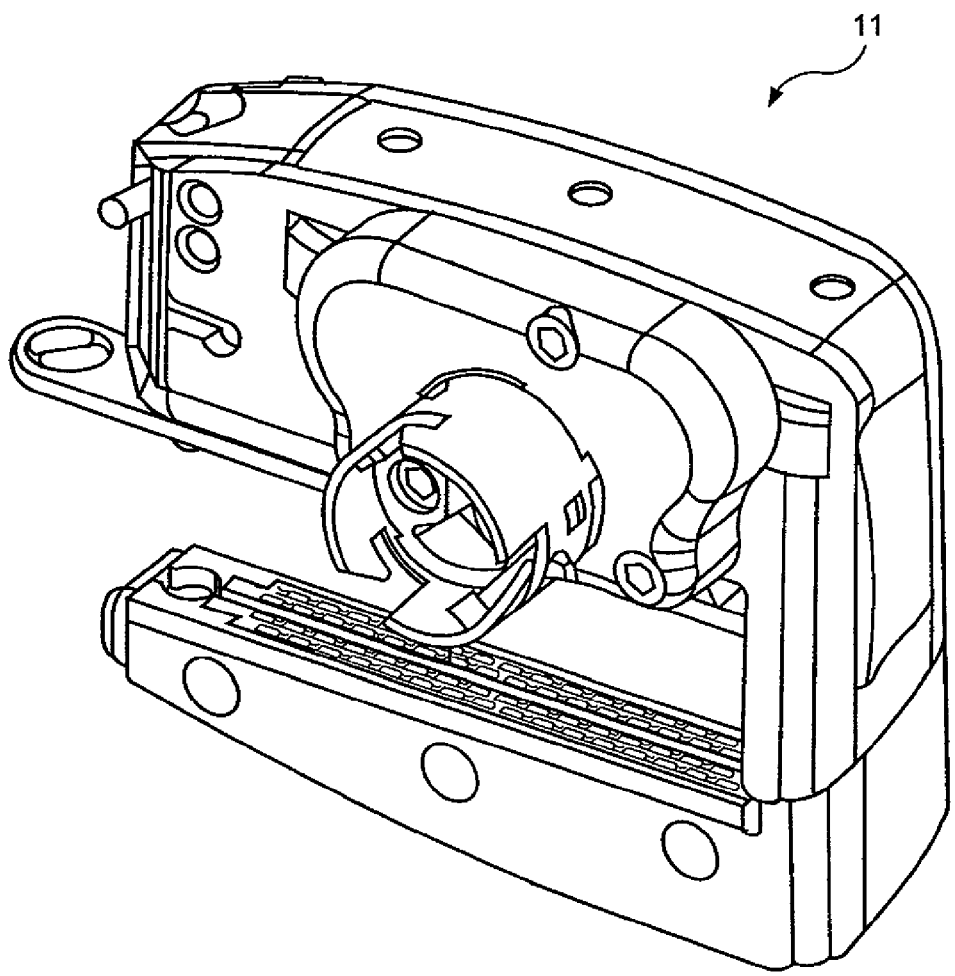
F I G. 9A

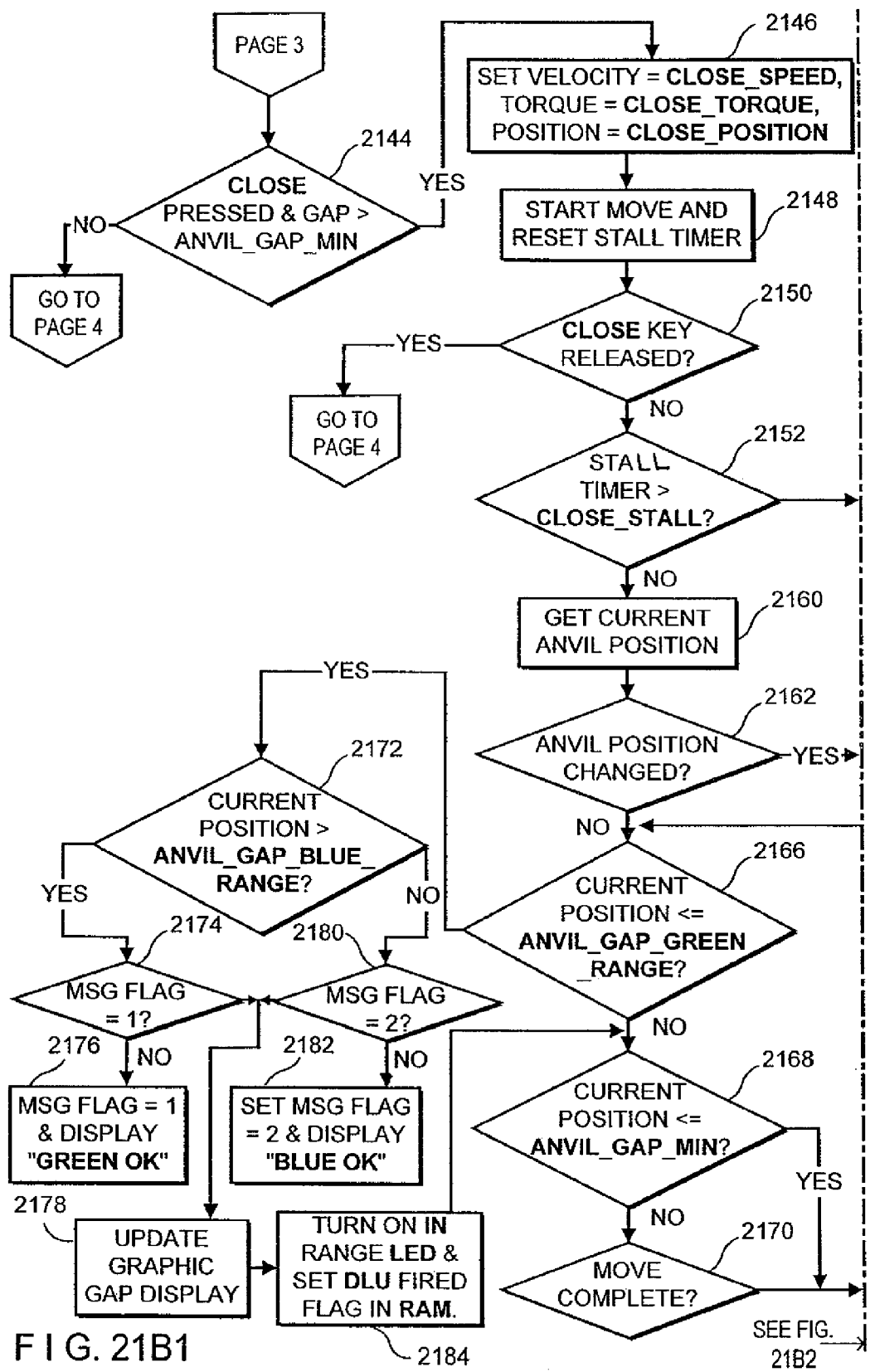
FIG. 21B1

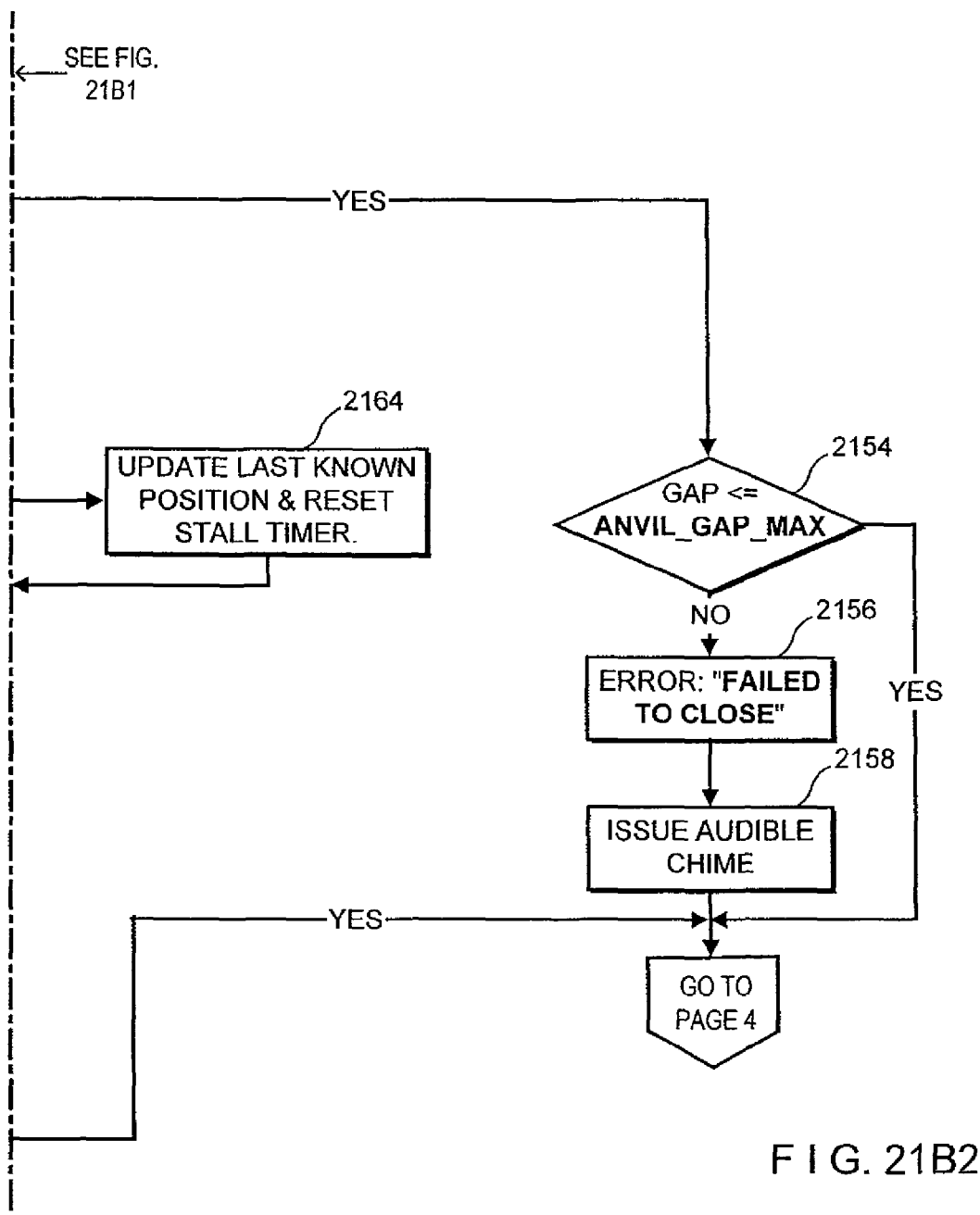
FIG. 21B2

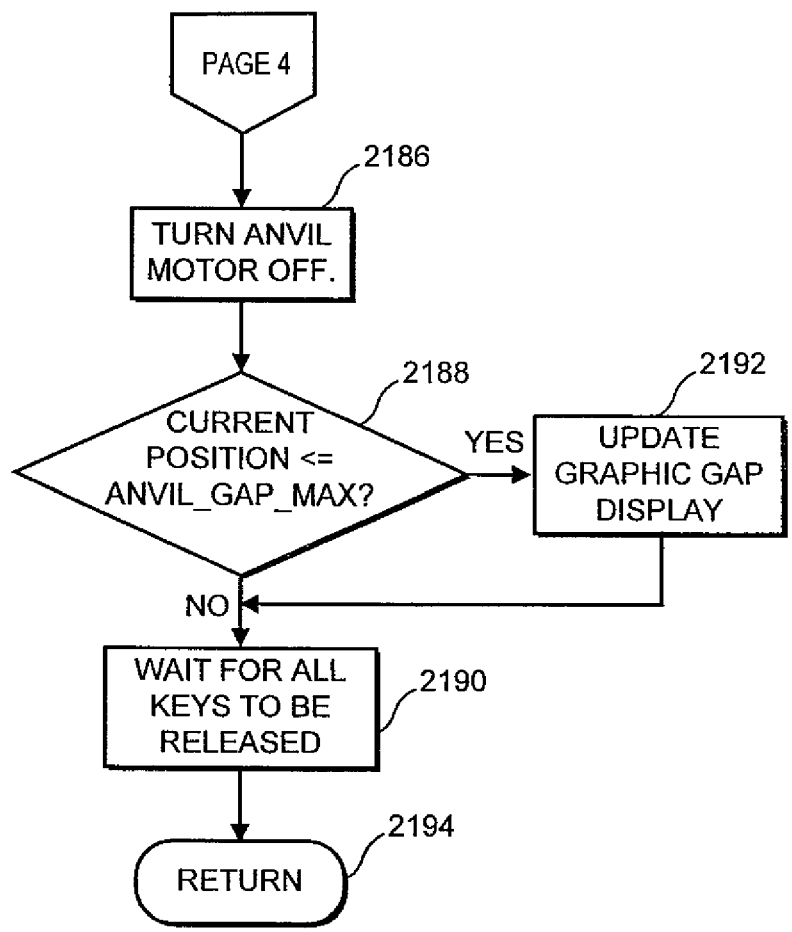
F I G. 21C

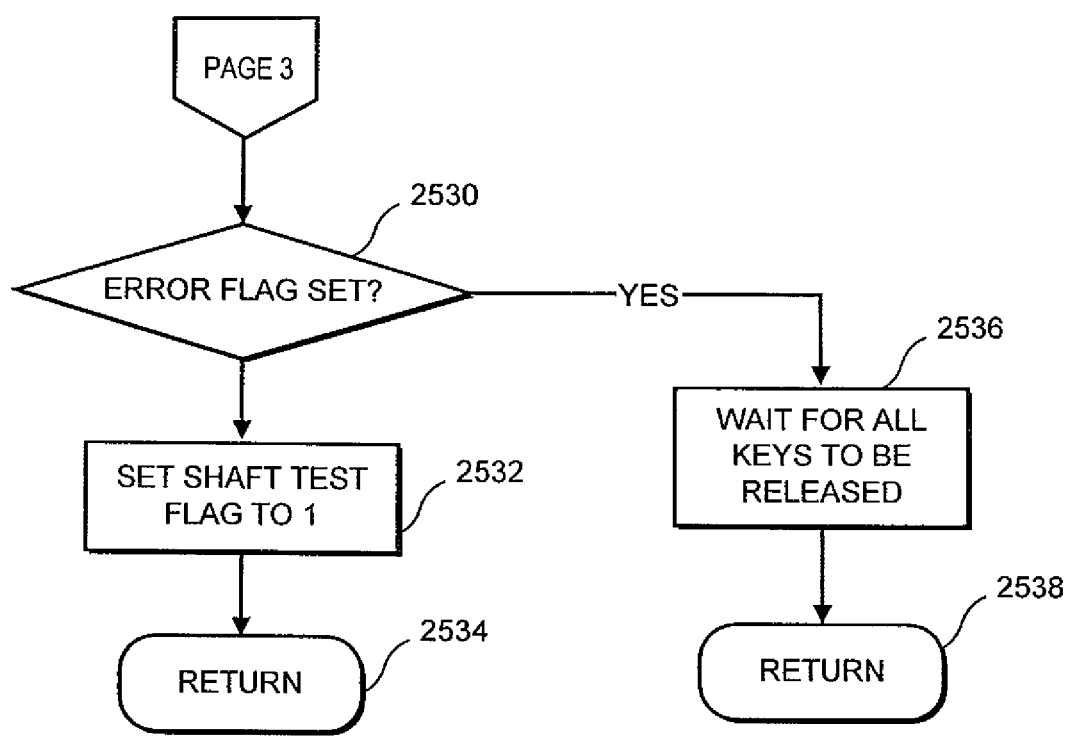
F I G. 25B

SURGICAL DEVICE

CROSS-REFERENCE TO RELATED APPLICATIONS

The present application is a Continuation Application claiming the benefit of and priority to U.S. patent application Ser. No. 13/217,611, filed Aug. 25, 2011 (now U.S. Pat. No. 8,518,074), which is a Continuation Application claiming the benefit of and priority to U.S. patent application Ser. No. 10/094,051, filed Mar. 8, 2002 (now U.S. Pat. No. 8,016,855), which claims the benefit of and priority to U.S. Provisional Patent Application Ser. No. 60/346,656, filed on Jan. 8, 2002, which is expressly incorporated herein by reference in its entirety.

The present application is related to U.S. patent application Ser. No. 09/510,923, filed on Feb. 22, 2000 (now U.S. Pat. No. 6,517,565), U.S. patent application Ser. No. 09/723,715, filed on Nov. 28, 2000 (now U.S. Pat. No. 6,793,652), U.S. patent application Ser. No. 09/836,781, filed on Apr. 17, 2001 (now U.S. Pat. No. 6,981,941), U.S. patent application Ser. No. 09/887,789, filed on Jun. 22, 2001 (now U.S. Pat. No. 7,032,798), and U.S. patent application Ser. No. 60/337,544, filed on Dec. 4, 2001, each of which is expressly incorporated herein by reference in its entirety.

FIELD OF THE INVENTION

The present invention relates to a surgical device. More specifically, the present invention relates to a clamping, cutting and stapling device for clamping, cutting and stapling tissue.

BACKGROUND INFORMATION

The literature is replete with descriptions of surgical devices. Some of these surgical devices are described in U.S. Pat. No. 4,705,038 to Sjostrom et al.; U.S. Pat. No. 4,995,877 to Ams et al.; U.S. Pat. No. 5,249,583 to Mallaby; U.S. Pat. No. 5,395,033 to Byrne et al.; U.S. Pat. No. 5,467,911 to Tsuruta et al.; U.S. Pat. Nos. 5,383,880, 5,518,163, 5,518,164 and 5,667,517, all to Hooven; U.S. Pat. No. 5,653,374 to Young et al.; U.S. Pat. No. 5,779,130 to Alesi et al.; and U.S. Pat. No. 5,954,259 to Viola et al.

One type of surgical device is a straight stapling device, which is a guillotine-type device that is used to cut and staple a section of tissue. FIG. 1(a) illustrates an example of such a device as described in U.S. Pat. No. 3,494,533. The device illustrated in FIG. 1(a) includes opposing jaws that move in parallel correspondence to each other. A first jaw has disposed therein an arrangement of staples while the second jaw provides an anvil for receiving and closing the staples. A staple pusher is located within the first jaw and extends from a proximal end of the first jaw to a distal end of the first jaw. A drive shaft, coupled to the first jaw and to the staple pusher, is located in the plane of movement of the first jaw and the staple pusher. When actuated, the drive shaft drives the staple pusher so as to simultaneously push all of the staples against the staple guides in the anvil of the second jaw.

Other examples of surgical devices are described in U.S. Pat. No. 4,442,964, U.S. Pat. No. 4,671,445, and U.S. Pat. No. 5,413,267. Such surgical staplers include opposing jaws that move in parallel correspondence to each other, wherein a first jaw has disposed therein an arrangement of staples while the second jaw provides an anvil for receiving and closing the staples. A staple pusher is located within the first jaw and that extends from a proximal end of the first jaw to a distal end of the first jaw. A drive shaft, coupled to the first jaw and to the staple pusher, is located in the plane of movement of the first jaw and the staple pusher and when actuated, the drive shaft drives the staple pusher so as to simultaneously push all of the staples against the staple guides in the anvil of the second jaw.

Another type of surgical device is a linear clamping, cutting and stapling device, such as that described in U.S. Pat. No. 6,264,087. Such a device may be employed in a surgical procedure to resect a cancerous or anomalous tissue from a gastrointestinal tract. A conventional linear clamping, cutting and stapling instrument is illustrated in a perspective view in FIG. 1(b). The device includes a pistol grip-styled structure having an elongated shaft and distal portion. The distal portion includes a pair of scissors-styled gripping elements, which clamp the open ends of the colon closed. One of the two scissors-styled gripping elements, the anvil portion, moves or pivots relative to the overall structure, whereas the other gripping element remains fixed relative to the overall structure. The actuation of this scissoring device, i.e., the pivoting of the anvil portion, is controlled by a grip trigger arranged in the handle. In addition to the scissoring device, the distal portion also includes a stapling mechanism. The fixed gripping element of the scissoring mechanism includes a staple cartridge receiving region and a mechanism for driving the staples through the clamped end of the tissue, against the anvil portion, thereby sealing the previously opened end. The scissoring elements may be integrally formed with the shaft or may be detachable such that various scissoring and stapling elements may be interchangeable.

Generally, these surgical devices are employed in the following manner: upon identification of cancerous or other anomalous tissue in the gastrointestinal tract (and upon determination that the cancerous tissue is located at a position in the colon), a patient's abdomen is initially opened to expose the bowel. A surgeon then cuts the tube of the colon on either side of the cancerous tissue, and staples closed the two open ends of the bowel (a distal end which is directed toward the anus, and the proximal end which is closest to the lower intestine). This temporary closure is performed in order to minimize contamination of the exposed abdomen by the bowel contents. More particularly, this temporary closure of the two open ends of the bowel is achieved when the colon is placed between the jaws of the surgical device. By actuating a first driving mechanism, the surgeon causes the jaws to come together. A second driving mechanism is then actuated to drive a series of staples and a cutting blade through the clamped end of the colon, thereby closing and transecting the ends. This procedure is typically repeated a second time on the other side of the cancerous or anomalous tissue.

One problem with the foregoing surgical devices is that the devices may be difficult to maneuver. Because these devices may be employed corporally, e.g., inside the body of a patient, the device should be configured so as to be maneuverable inside the body of a patient. Conventional surgical devices, such as those illustrated in FIGS. 1(a) and 1(b), are difficult to maneuver, especially inside the patient's body.

SUMMARY OF THE INVENTION

The present invention, according to one example embodiment thereof, relates to a surgical device. The surgical device includes a first jaw and a second jaw in opposed correspondence with the first jaw. A first driver is configured to cause relative movement of the first jaw and the second jaw in a plane. The first driver is configured to engage a drive shaft rotatable about a rotation axis arranged in non-parallel correspondence to the plane. The surgical device may also include a surgical member disposed within the first jaw. A second driver is configured to cause relative movement of the surgical member in a direction parallel to the plane. The second driver is configured to engage a drive shaft rotatable about a rotation axis arranged in non-parallel correspondence to the plane.

According to one example embodiment of the present invention, a first drive socket is configured to couple to one end of a first rotatable drive shaft, arranged at an angle, e.g., perpendicular, to the plane of the first and second jaws of an electro-mechanical driver, wherein the electro-mechanical driver is configured to rotate the first rotatable drive shaft. The first rotatable drive shaft is rotated in a first direction to effect opening of the jaws and is rotated in a second direction opposite to the first direction to effect closing of the jaws. The first driver may include, for example, a pair of spur gears, a worm and a worm gear in turning and gearing relationship with each other. The first driver may also include an externally-threaded screw fixedly connected at one end to one of the worm gears and in engagement with an internally-threaded bore of the second jaw, the rotation of the gears thereby causing relative movement of the first jaw and the second jaw.

As indicated above, the surgical device may also include a surgical member, such as a cutting element, e.g., a knife, and a stapling element mounted to a thrust plate disposed within the first jaw. According to this example embodiment, a second driver is disposed within the first jaw. The second driver is configured to move the surgical member in a direction parallel to the plane of movement of the first and second jaws. The second driver includes a second drive socket, which is arranged at an angle, e.g., perpendicular, to the plane.

According to one example embodiment of the present invention, the second drive socket of the second driver is configured to couple to one end of a second rotatable drive shaft, arranged at an angle, e.g., perpendicular, to the plane of the first and second jaws of an electro-mechanical driver, wherein the electro-mechanical driver is configured to rotate the second rotatable drive shaft. The second rotatable drive shaft is rotated in a first direction to lower the surgical member and rotated in a second direction opposite to the first direction to raise the surgical member. The second driver may include, for example, a pair of spur gears, a worm and a pair of worm gears in turning and gearing relationship with each other.

Each of this pair of worm gears has a centrally-disposed, internally-threaded bore in engagement with a respective one of a pair of externally-threaded screws fixedly connected the surgical member. The rotation of the gears causes relative movement of the surgical member.

BRIEF DESCRIPTION OF THE DRAWINGS

FIG. 9(a) is a perspective view of the cutting and stapling attachment illustrated in FIG. 8(a);

FIGS. 21(a) to 21(c) illustrate a flowchart of a jaw-closing routine of the main operating program illustrated in FIGS. 20(a) to 20(c) in accordance with one example embodiment of the present invention;

FIGS. 25(a) to 25(b) illustrate a flowchart of a testing routine of the main operating program illustrated in FIGS. 20(a) to 20(c) in accordance with one example embodiment of the present invention.

DETAILED DESCRIPTION

Figure 3:
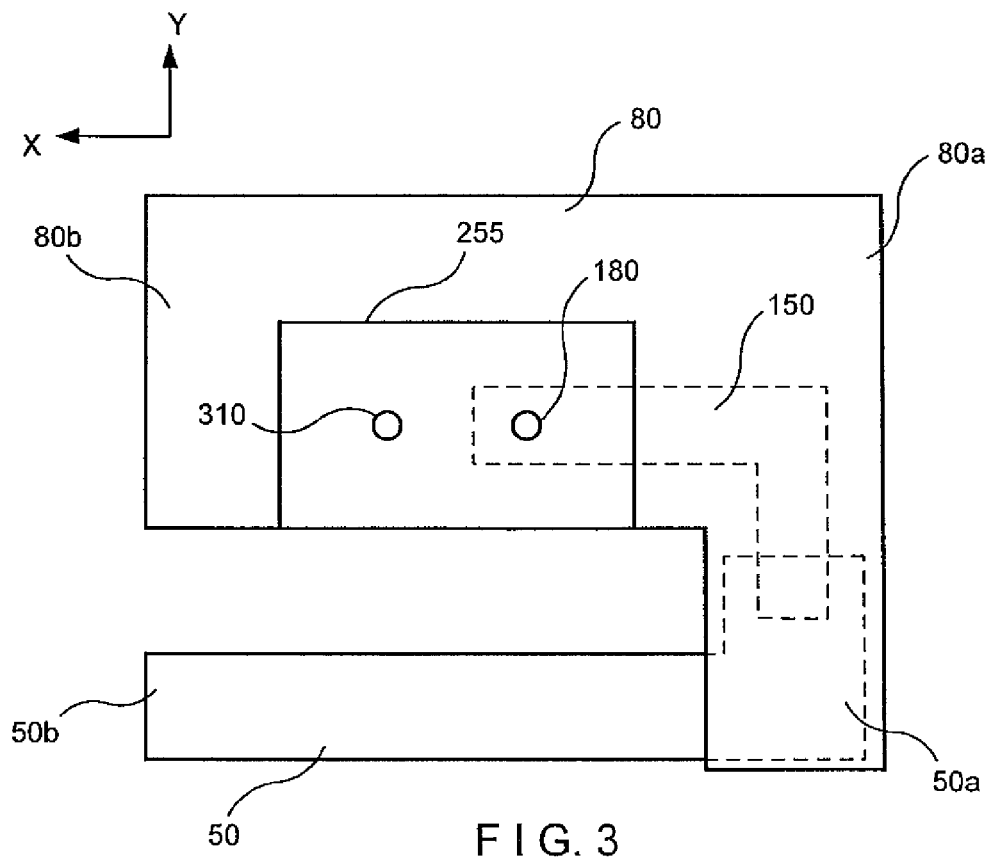
FIG. 3 is a side view of a cutting and stapling attachment according to one example embodiment of the present invention in an extended position.
Figure 4:
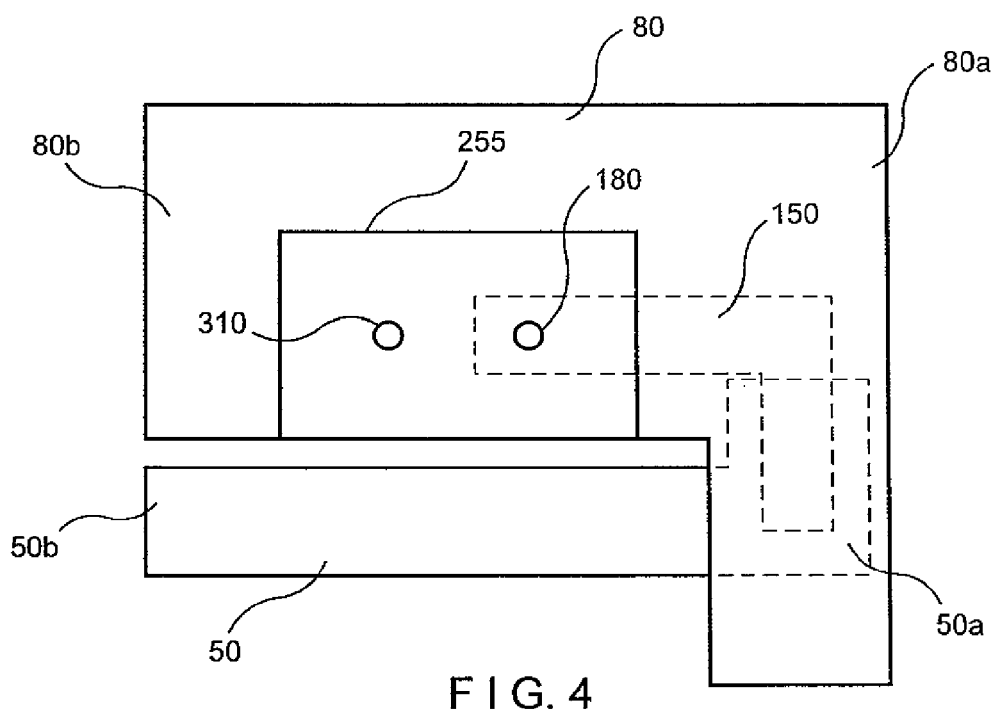
FIG. 4 is a side view of the cutting and stapling attachment illustrated in FIG. 3 in a retracted position.

One example embodiment of a surgical device 11 according to the present invention is illustrated in FIGS. 3 to 7. Referring to FIGS. 3 and 4, an example embodiment of the surgical device 11, e.g., a clamping, cutting and stapling device, is illustrated. In this example embodiment, the surgical device 11 includes a parallel separating jaw system having a second jaw 50 in opposite correspondence to a first jaw 80. A first end 50a of second jaw 50 is mechanically coupled to a first end 80a of first jaw 80. The opposing jaws 50 and 80 may remain parallel relative to each other. Alternatively, opposing jaws 50 and 80 may open and close in scissor-like fashion, wherein the first ends 50a and 80a of the second jaw 50 and the first jaw 80 are mechanically connected by a hinge or other rotational element such that the first jaw 80 is rotatably coupled to the second jaw 50.

FIG. 3 illustrates the surgical device 11 in an open position, wherein the second jaw 50 and the first jaw 80 are in contact with each other at their first ends 50a and 80a. The first jaw 80 and the second jaw 50 are maintained and move in a longitudinal plane defined by the x and y axes illustrated in FIG. 3. Mounted on a side of the first jaw 80a is a gear housing 255. The gear housing 255 includes a first drive socket 180 coupled to a first driver 150, which for purposes of clarity is illustrated schematically. The first driver 150 is coupled to a first end 50a of the second jaw 50 to open and close the first jaw 80 and the second jaw 50. In addition, the gear housing 255 also includes a second drive socket 310.

FIG. 4 illustrates the surgical device 11 in a closed position. In the closed position, the second jaw 50 and the first jaw 80 are in contact with each other at their first ends 50a and 80a and also at their second ends 50a and 50b. In the closed position, a section of tissue is clamped between the second jaw 50 and the first jaw 80.

Figure 5:
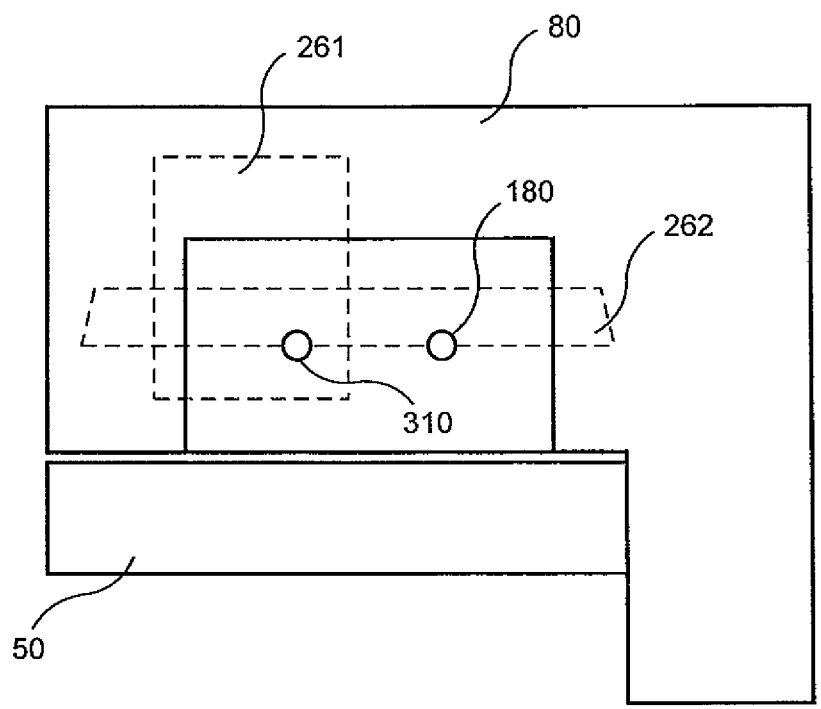
FIG. 5 is a side view of the cutting and stapling attachment illustrated in FIGS. 3 and 4 in the retracted position.
Figure 6:
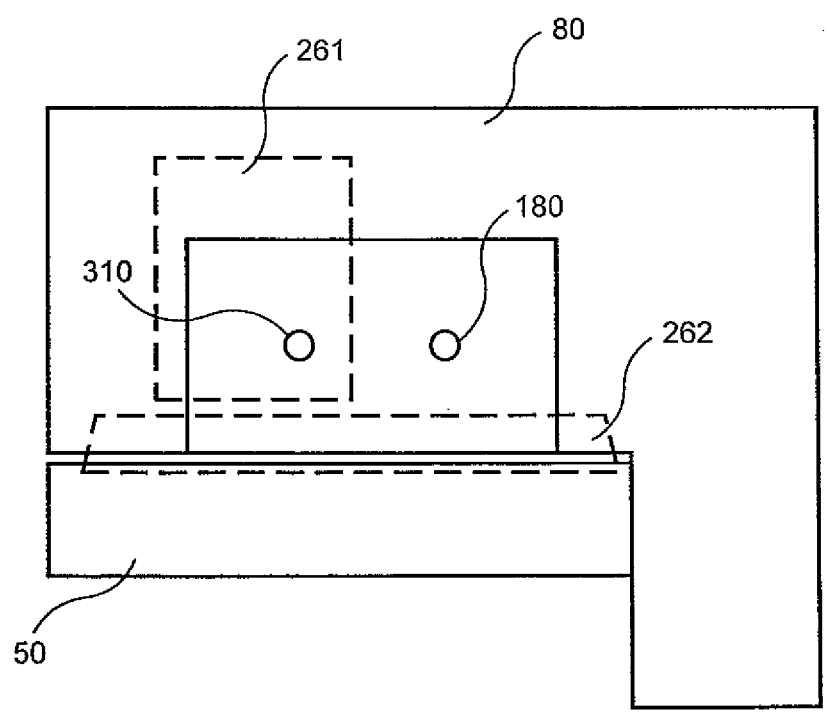
FIG. 6 is a side view of the cutting and stapling attachment illustrated in FIGS. 3 to 5 in the retracted position.

FIGS. 5 and 6 also illustrate the surgical device 11 in the closed position.

FIGS. 5 and 6 illustrate the second drive socket 310 of the gear housing 255 coupled to a second driver 261, which is illustrated schematically. The second driver 261 is coupled to a surgical member 262. The surgical member 262 may include a cutting and stapling assembly 262, although other types of surgical members may be provided.

The second driver 261 is coupled to cutting and stapling assembly 262 to move the cutting and stapling assembly 262 from a first retracted position, as illustrated in FIG. 5, to a second extended position, as illustrated in FIG. 6. While two drive sockets, e.g., the first drive socket 180 and the second drive socket 310, and two corresponding drive shafts, e.g., the first drive shaft 630 and the second drive shaft 632, are illustrated, it is possible to provide any suitable number of drive sockets and drive shafts. For example, a single drive shaft may be provided to drive the surgical device.

Figure 7:
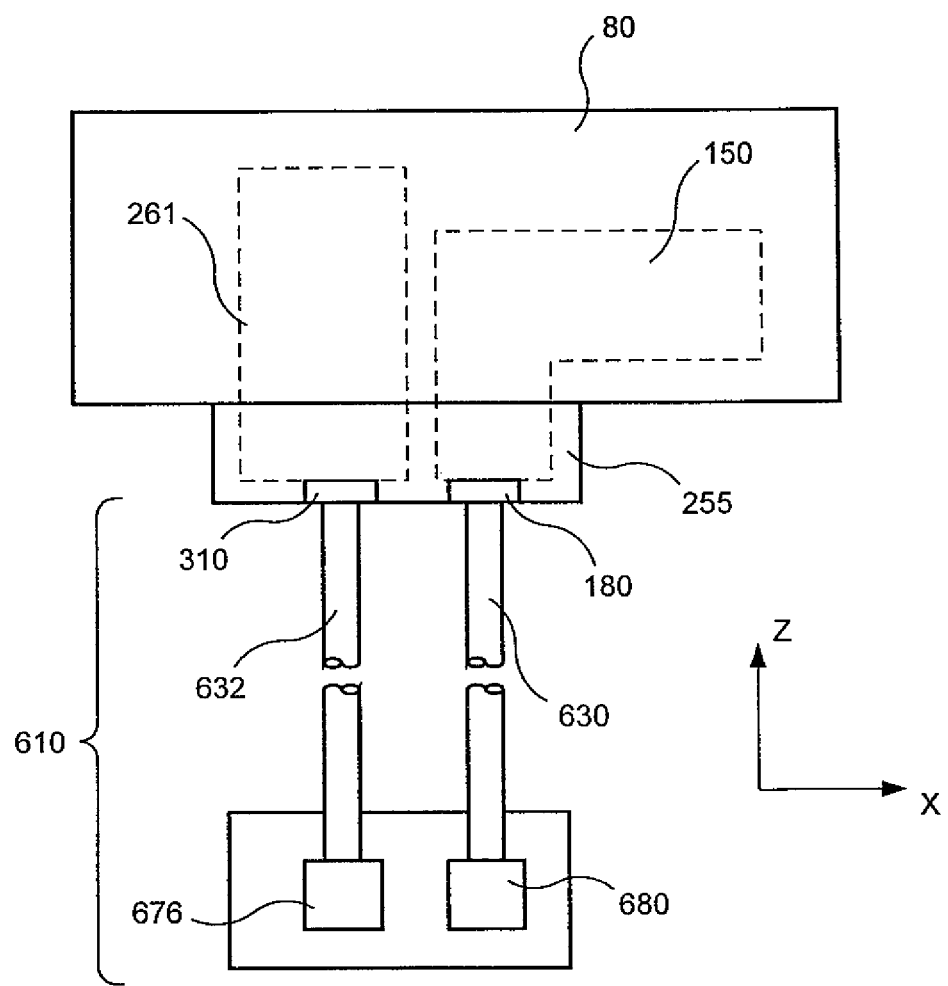
FIG. 7 is a top view of the cutting and stapling attachment illustrated in FIGS. 3 and 4.

FIG. 7 is a top view of the surgical device 11 illustrated in FIGS. 3 to 6. FIG. 7 illustrates the surgical device 11 coupled, e.g., removably or permanently, to an electro-mechanical driver component 610. FIG. 7 illustrates the surgical device 11 including the first driver 150, which is coupled via first drive socket 180 to a first motor 680 of the system 610 by a first drive shaft 630. The first driver 150, when engaged by system 610, operates to open and close the first jaw 80 relative to the second jaw 50. In addition, FIG. 7 illustrates the surgical device 11 including a second driver 261, which is coupled via the second drive socket 310 to a second motor 676 of system 610 by a second drive shaft 632. The second driver 261, when engaged by the system 610, operates to drive a cutting and stapling assembly 262. As illustrated in FIG. 7, the first drive socket 180 and the second drive socket 310 are disposed on the surgical device 11 so that the first drive shaft 630 and the second drive shaft 632 are coupled to the surgical device 11 at an angle, e.g., perpendicularly, to the x-y plane illustrated in FIG. 3. That is, the first drive shaft 630 and the second drive shaft 632 are coupled to the surgical device 11 in the direction of the z-axis illustrated in FIG. 7.

Figure 8A:
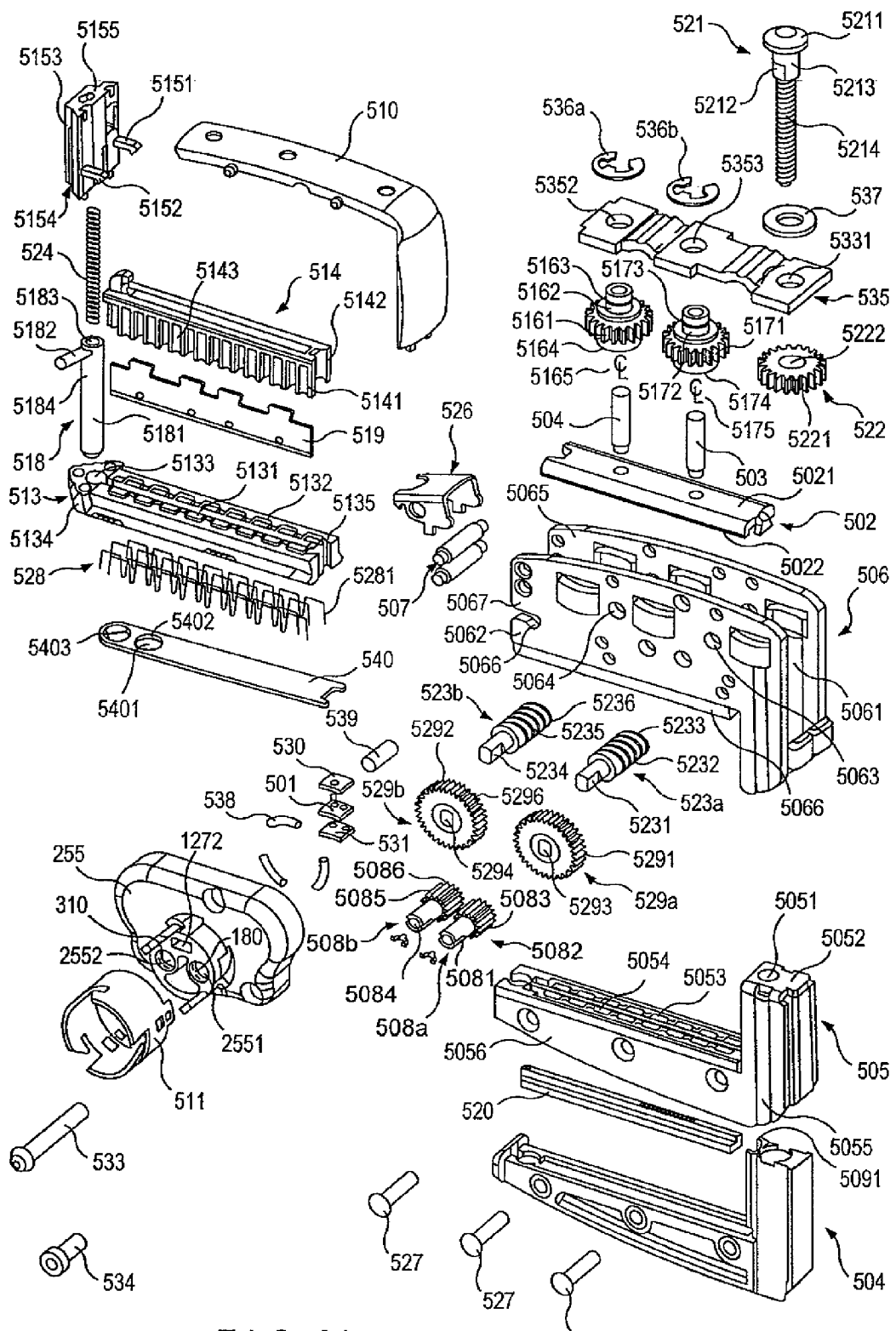
FIG. 8(a) is an exploded view of a cutting and stapling attachment according to one example embodiment of the present invention.

FIG. 8(a) is an exploded view of the surgical device 11 according to one example embodiment of the present invention, and FIG. 9(a) is a perspective view of the surgical device 11 assembled. According to this example embodiment, the second jaw 50 includes an anvil 505, which is coupled to an anvil filler 509 by fasteners 527, e.g., rivets. The anvil 505 includes a vertically-disposed, internally-threaded bore 5051 at its upper end 5052. In addition, the anvil 505 includes a plurality of staple guides 5053 in a parallel-disposed arrangement along a region 5054 of the anvil 505 that is in opposite correspondence to first jaw 80. A knife pad 520 is disposed between the plurality of staple guides 5053.

The first jaw 80 includes a housing frame 506. The housing frame 506 includes a pair of internally disposed guides 5061 along which a pair of ribs 5055 of the anvil 505 may travel, so that the housing frame 506 may move parallel with, and in opposite correspondence to, the anvil 505. A gear housing 255 is mounted to one side 5062 of the housing frame 506 via fasteners 533 and 534, e.g., screws.

A quick-connect coupling 511 is mounted onto the gear housing 255 and is biased via a set of springs 538. The gear housing 255 includes the first drive socket 180 and the second drive socket 310. In this example embodiment, the first drive socket 180 includes the first pinion 508a, one end 5081 of which extends through an opening 2551 of the gear housing 255 and the other end 5082 of which includes spur gear teeth 5083. The second drive socket 310 includes the second pinion 508b, one end 5084 of which extends through a second opening 2552 of the gear housing 255 and the other end 5085 of which includes spur gear teeth 5086. A memory module 501 is arranged in the gear housing 255 and includes a connector 2554 that extends through, or is accessible through, an opening 2553 of the gear housing 255. The memory module 501 is maintained in position within the gear housing 255 by an inboard shim 530 and an outboard shim 531. The memory module 501 is also biased in its position by a spring 539.

Each of the first and second pinions 508a and 508b engages a respective spur gears 529a and 529b. The first spur gear 529a includes an internal bore 5293 which non-rotatably engages an end 5231 of the first worm 523a. The second spur gear 529b includes an internal bore 5294 which non-rotatably engages an end 5234 of the second worm 523b. As illustrated in FIG. 8(a), the bores 5293 and 5294 and the ends 5231, 5234 may be, e.g., square. It should be understood that the bores 5293, 5294 and the ends 5231, 5234 may have any shape or configuration that provides non-rotatable engagement therebetween.

In this example embodiment, the first worm 523a has one end 5231, which non-rotatably engages the internal bore 5293 of the first spur gear 529a, and a second end 5232, which includes circumferentially-disposed thread(s) 5233. The second worm 523b has one end 5234, which non-rotatably engages the internal bore 5294 of the second spur gear 529b, and a second end 5235 which includes circumferentially-disposed threads 5236. The second end 5232 of the first worm 523a is disposed within the frame housing 506, and the end 5231 of the worm 523a extends through a hole 5063 in the side of the frame housing 506 to engage the first spur gear 529a in the gear housing 255. The second end 5235 of the second worm 523b is disposed within the frame housing 506, and the end 5234 of the worm 523b extends through a hole 5064 in the side of the frame housing 506 to engage the second spur gear 529b in the gear housing 255.

Also disposed within the frame housing 506 is worm gear 522. Worm gear 522 has circumferentially-disposed teeth 5221, which engage the thread(s) 5233 of the second end 5232 of the worm 523a. The worm gear 522 includes an internal bore 5222 through which is disposed a screw 521. The screw 521 has a head 5211 with a portion 5212, which non-rotatably engages the internal bore 5222 of worm gear 522. The internal bore 5222 and the portion 5212 of the screw 521 may be complementary, e.g., square. The screw 521 also includes a portion 5213 of the head 5211 that extends through a washer 537 and a hole 5351 in a bearing plate 535. The screw 521 also has externally-disposed threads 5214, which engage the internally-threaded bore 5051 of the anvil 505.

A worm gear 516 and a worm gear 517 are disposed within the frame housing 506. The worm gear 516 and the worm gear 517 are positioned on opposite sides of the worm 523b. Specifically, the worm gear 516 includes circumferentially-disposed gear teeth 5161, which engage a first side of the worm 523b, and the worm gear 517 includes circumferentially-disposed gear teeth 5171, which engage a second side of the worm 523b. The worm gear 516 includes a cylindrical projection 5162, which extends through a hole 5352 in the bearing plate 535. Retaining ring 536a engages a groove 5163 of the cylindrical projection 5162 so that the worm gear 516 is rotatable about its vertical central axis 5165 relative to the bearing plate 535. The worm gear 517 includes a cylindrical projection 5172, which extends through a hole 5353 in the bearing plate 535. Retaining ring 536b engages a groove 5173 of the cylindrical projection 5172 so that the worm gear 517 is rotatable about its vertical central axis 5175 relative to the bearing plate 535.

An externally-threaded screw 504 is disposed through an internally-threaded bore 5164 of the worm gear 516. An externally-threaded screw 503 is disposed through an internally-threaded bore 5174 of worm gear 517. Because the worm gears 516 and 517 are located on, and engage, opposite sides of the worm 523b, the internally-threaded bores 5164 and 5174 of the worm gears 516 and 517, as well as the externally-threaded screws 504 and 503, may be oppositely threaded relative to each other. In the example embodiment illustrated, the internally-threaded bore 5164 of the worm gear 516 may have a right-hand thread, which engages the right-hand external thread of the screw 504, and the internally-threaded bore 5174 of the worm gear 517 may have a left-handed thread, which engages the left-handed external thread of the screw 503. Both the screws 503 and 504 are fixedly coupled to a top surface 5021 of a thrust plate 502. The thrust plate 502 is positioned between the opposite sides of the housing frame 506.

A staple pusher 514 is attached to a bottom surface 5022 of the thrust plate 502. The staple pusher 514 includes parallel rows 5141 and 5142 of downwardly-disposed teeth 5143, each of which corresponds to and aligns with a staple guide 5053 of the anvil 505. A knife 519 having a cutting edge 5191 facing downwardly is disposed between the parallel rows of downwardly-disposed teeth 5143 of the staple pusher 514.

A staple holder 513 is disposed below the staple pusher 514. The staple holder 513 includes a cartridge having vertically-disposed slots 5132, each of which corresponds to and aligns with the downwardly-disposed teeth 5143 of the staple pusher 514 and with the staple guides 5053 of the anvil 505. A staple 228, which includes prongs 5281, is provided in each slot 5132. The staple holder 513 also includes a longitudinally-disposed slot 5131, which extends through the staple holder 513 and through which knife 519 may be passed. The staple holder 513 includes a hole 5133 adjacent to one end 5134.

A staple retainer 540 is attached to the lower parallel edges 5066 of the frame housing 506 or to a bottom surface of the staple holder 513. The staple retainer 540 is configured to cover the bottom surface of the staple holder 513 so as to maintain the staples 528 within the staple holder 513 and to prevent foreign material from entering the slots 5132 of the staple holder 513 during shipping of the surgical device 11. The staple retainer 540 has a through-hole 5401 having a tapered or beveled edge 5402. The staple retainer 540 also has a grip region 5403 that is configured to be gripped by a user.

The hole 5133 of the staple holder 513 that is adjacent to the one end 5134 of the staple holder 513 is configured to receive an end 5181 of a pin 518. The end 5181 of the pin 518 is tapered so as to seat against the tapered edge 5402 of the through-hole 5401 of the staple retainer 540. In the example embodiment, the pin 518 is maintained in a substantially vertical position so as to be perpendicular to the staple holder 513. The pin 518 includes a centrally-disposed internal bore 5183 at its opposite end 5184 configured to receive a spring 524. Also located at the end 5184 of the pin 518 is a lever 5182 which is attached perpendicularly to the pin 518. When the staple holder 540 is removed from the surgical device 11, the spring 524 biases the end 5181 of the pin 518 into an orifice 5057 of the anvil 505.

A cartridge cap 515 is attached, such as by welding, to an end 5067 of the frame housing 506. Latches 5151 and 5152 of the cartridge cap 515 engage notches 5068 of the housing frame 506. The cartridge cap 515 also includes an internally-disposed bore 5154 which is configured to receive pin 518. Bore 5154 of the cartridge cap 515 includes a slot 5153 in communication therewith, the slot 5153 configured to guide the lever 5182 of the pin 518. In the example embodiment, the internally-disposed bore 5154 of the cartridge cap 515 does not extend through the top surface 5155 of the cartridge cap 515; instead, it maintains the spring 524 within the internally-disposed bore 5154. The biasing force of the spring 524 pushes the end 5181 of the pin 518 into the hole 5133 of the staple holder 513 and tends to ensure that the staple holder 513 is positioned so that the slots 5132 align with the downwardly-disposed teeth 5143 of the staple pusher 514 and with the staple guides 5053 of the anvil 505. The cartridge cap 515 is also maintained in position by a latch 526, which is pivotably attached to the housing frame 506 by fasteners 507. A housing top 510 is arranged between the opposite sides 5062 and 5065 of the housing frame 506 and protects the components within the housing frame 506.

Figure 8B:
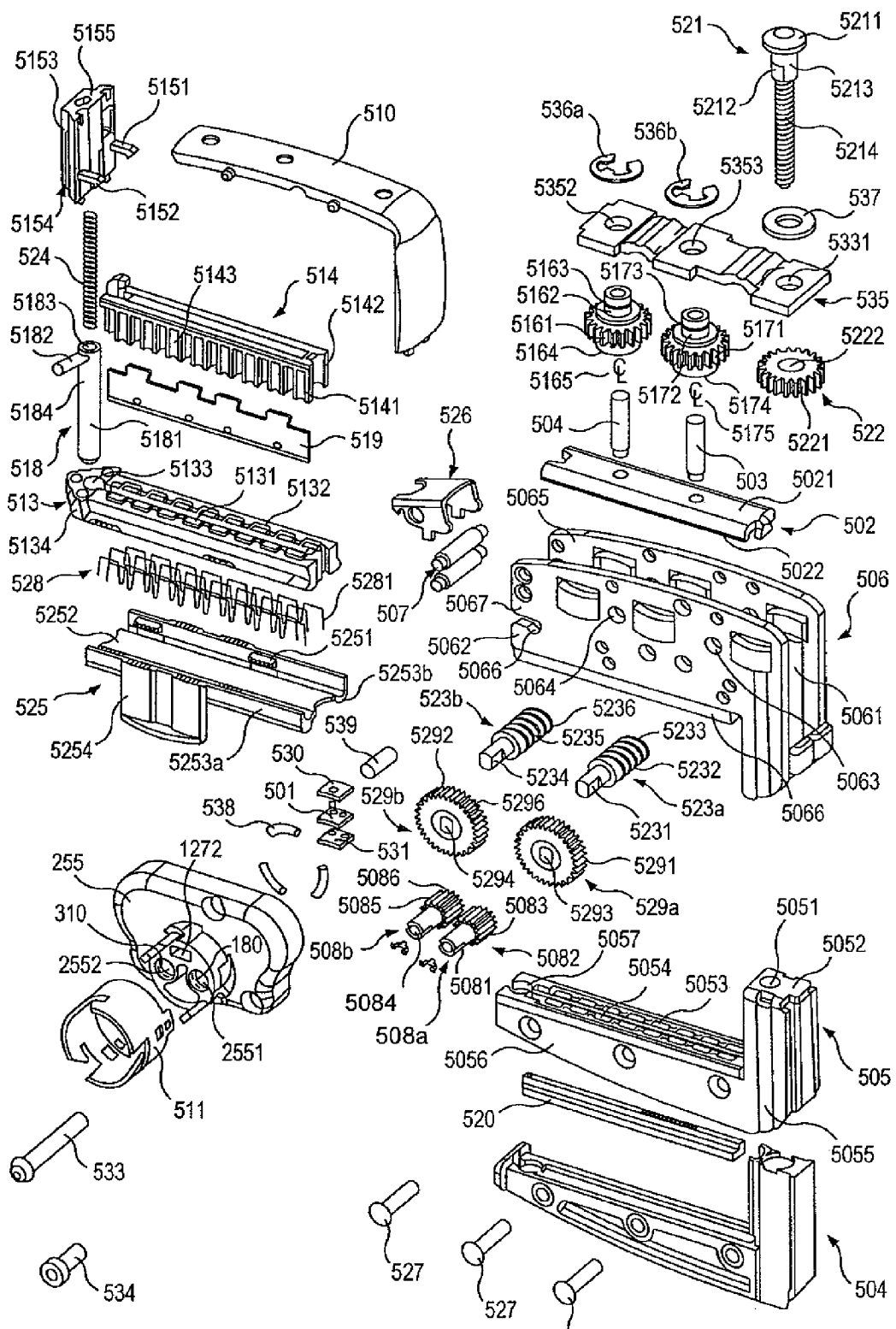
FIG. 8(b) is an exploded view of a cutting and stapling attachment according to another example embodiment of the present invention.
Figure 9B:
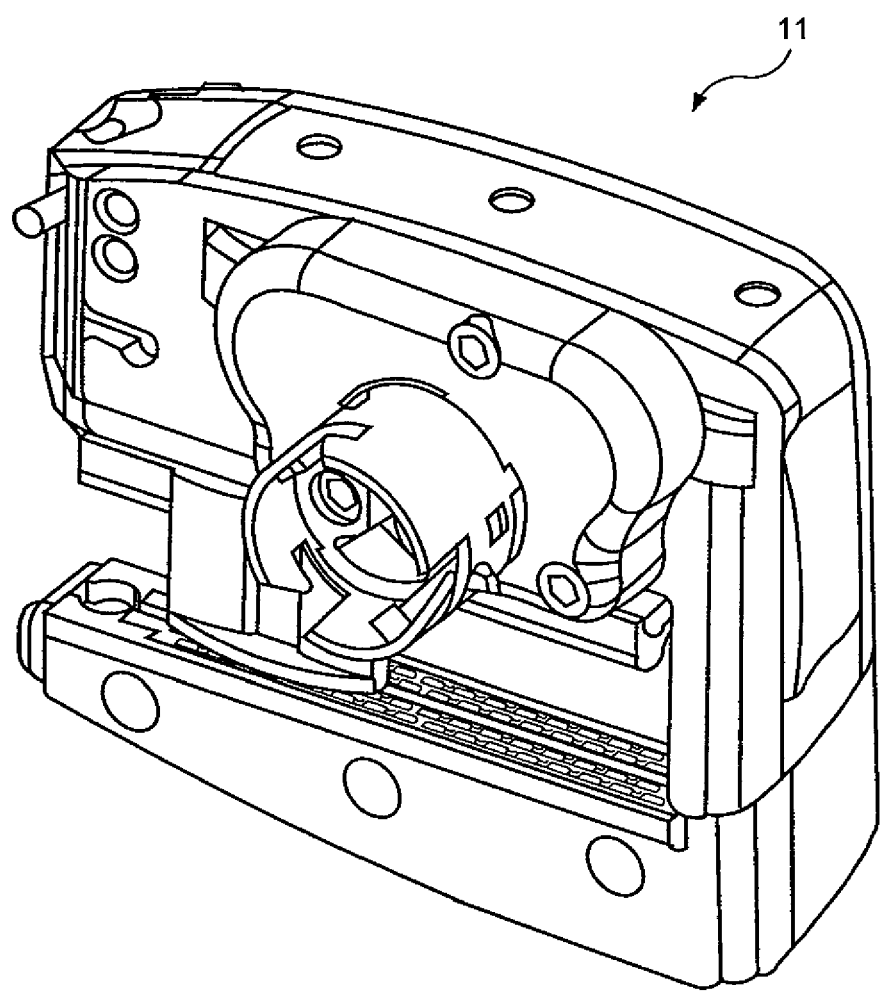
FIG. 9(b) is a perspective view of the cutting and stapling attachment illustrated in FIG. 8(b)

The example embodiment illustrated in FIG. 8(a) includes a thin flat staple retainer 540. This configuration of the staple retainer 540 is adapted to maintain the staples 528 in the staple holder 513 when the surgical device is initially maintained in the closed position, e.g., when the surgical device 11 is initially shipped to a user such that the first jaw 80 and the second jaw 50 contact opposite sides of the staple retainer 540. This configuration of the staple retainer 540 ensure that, during transportation, the staples 528 are maintained within the staple holder 513 and prevents damage to the staples 528 and to the staple guides 5053 of the anvil 505. However, in accordance with another example embodiment of the present invention, the surgical device 11 may initially be maintained in the open position. FIG. 8(b) is an exploded view of the surgical device 11, according to one example embodiment of the present invention, and FIG. 9(b) is a perspective view of the surgical device 11 illustrated in FIG. 8(b) assembled. More specifically, FIG. 8(b) illustrates the surgical device 11 having a staple retainer 525 configured to initially maintain the surgical device 11 in the open position, e.g., when the surgical device 11 is initially shipped to a user such that the first jaw 80 and the second jaw 50 are separated.

As illustrated in FIG. 8(b), the staple retainer 525 is attached via tabs 5251 to the lower parallel edges 5066 of the frame housing 506 and is configured to maintain the staples 528 within the staple holder 513 and to prevent damage to the staples 528 and to the staple guides 5053 of the anvil 505 during transportation. The staple retainer 525 includes a pair of guides 5254 positioned along the side edges 5253a and 5253b and which extend downwardly. Guides 5254 are configured to contact the outer sides 5056 of the anvil 505 so as to maintain the first jaw 80, e.g., the housing frame 506, etc., of the surgical device 11 in parallel correspondence with the second jaw 50 during the shipping and handling process. Thus, the guides 5254 may prevent misalignment of the first jaw 80 and second jaw 50 that may occur when the surgical device 11 is transported with the first jaw 80 and the second jaw 50 in the open position.

It should be understood that while the example embodiments of the present invention illustrated in FIGS. 3 to 9(b) include a guillotine-type arrangement of the stapling and cutting elements, in another embodiment, a stapling and cutting element is moved between a proximal end and a distal end of the surgical device 11. For example, an alternative example embodiment of the surgical device 11 may include gears coupled to a stapling and cutting element that is moved between a proximal end and a distal end of the surgical device 11, the gears driven by drive shafts that are coupled in non-parallel, e.g., perpendicular, correspondence to the plane of movement of the first jaw 80 and the second jaw 50.

According to one example embodiment of the present invention, the surgical device 11 may be configured as an attachment to, or may be integral with, an electro-mechanical surgical system, such as electro-mechanical driver component 610. In another example embodiment, the surgical device may be an attachment to, or may integral with, a mechanical driver system.

Figure 1A:
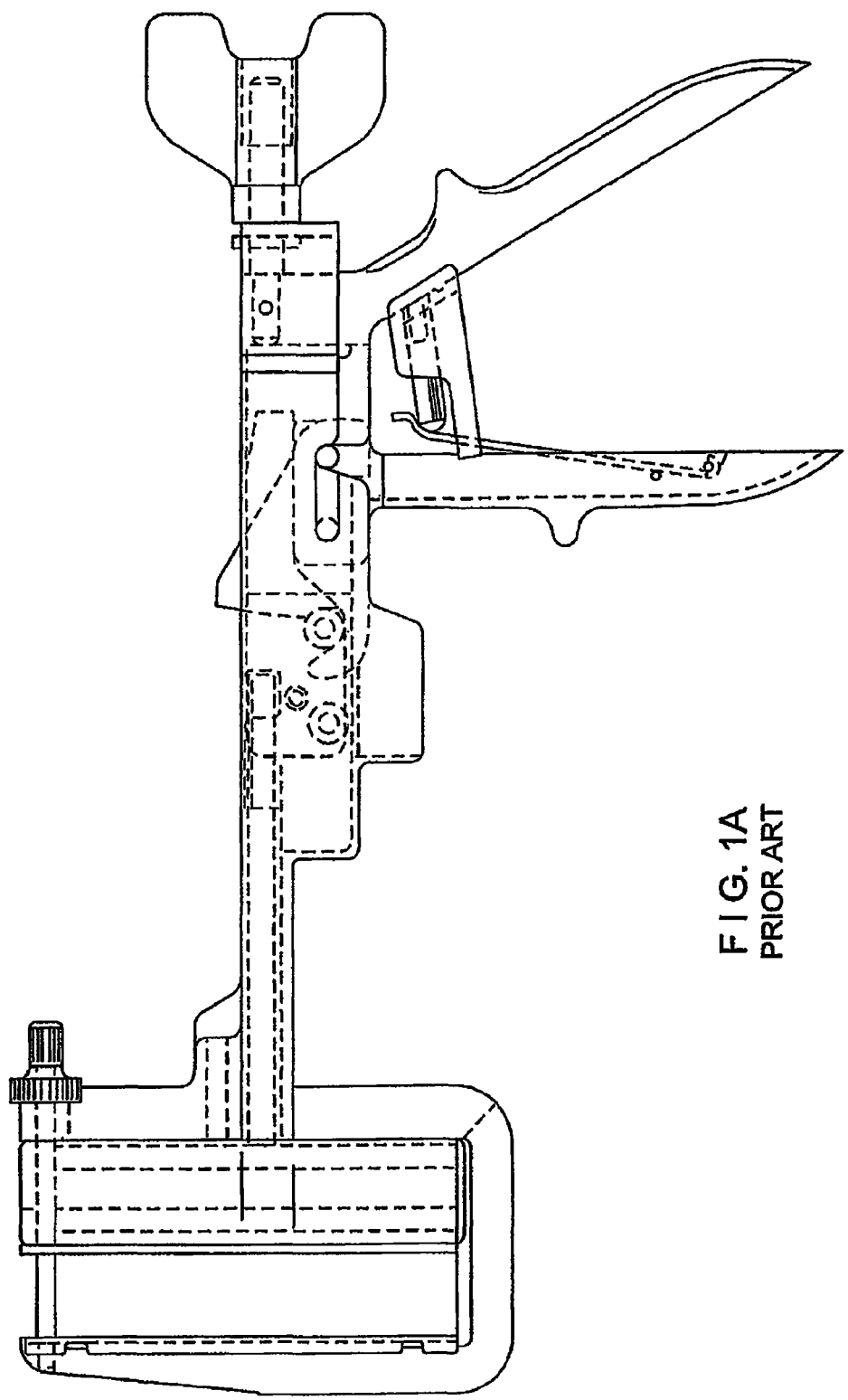
FIG. 1(a) is a side view of a conventional surgical device.
Figure 1B:
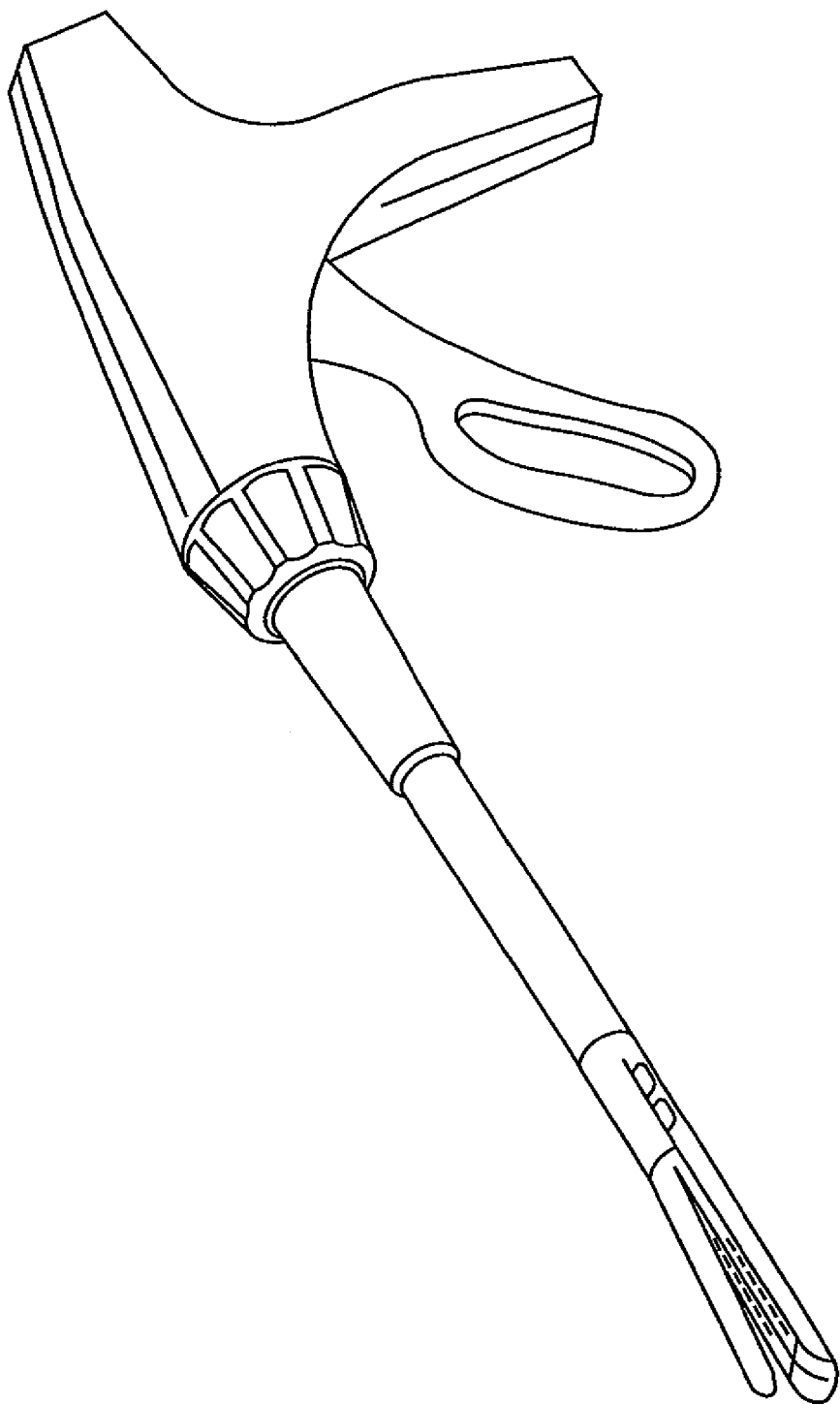
FIG. 1(b) is a perspective view of a conventional linear clamping, cutting and stapling device.
Figure 2:
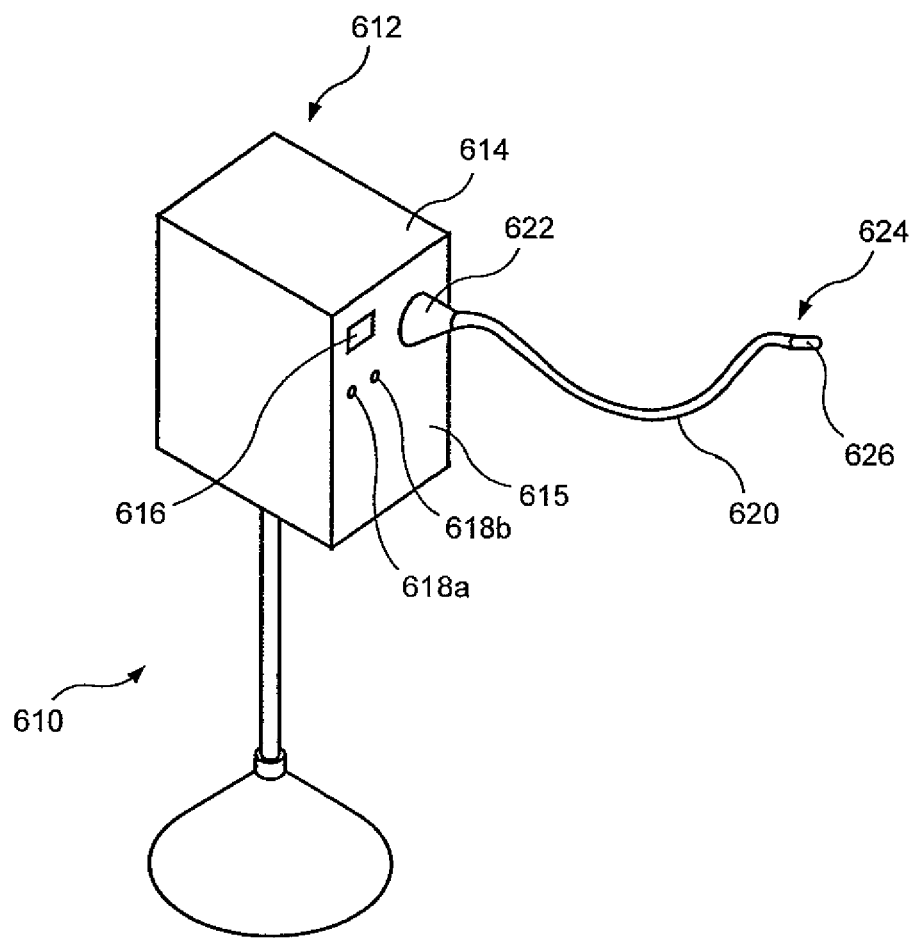
FIG. 2 is a perspective view of an electro-mechanical surgical system according to one example embodiment of the present invention.

FIG. 2 is a perspective view of an example embodiment of an electro-mechanical driver component 610 according to the present invention. Examples of such an electro-mechanical driver component are described in, e.g., U.S. patent application Ser. No. 09/723,715 (now U.S. Pat. No. 6,793,652), U.S. patent application Ser. No. 09/836,781 (now U.S. Pat. No. 6,981,941) and U.S. patent application Ser. No. 09/887,789 (now U.S. Pat. No. 7,032,798), each of which is expressly incorporated herein in their entirety by reference thereto. Electro-mechanical driver component 610 may include, for example, a remote power console 612, which includes a housing 614 having a front panel 615. Mounted on front panel 615 are a display device 616 and indicators 618a, 618b. A flexible shaft 620 may extend from housing 614 and may be detachably attached thereto via a first coupling 622. The distal end 624 of flexible shaft 620 may include a second coupling 626 adapted to detachably attach, e.g., the surgical device 11 described above, to the distal end 624 of flexible shaft 620. The second coupling 626 may also be adapted to detachably attach a different surgical instrument or attachment. In another example embodiment, the distal end 624 of the flexible shaft 620 may permanently attach to or be integral with a surgical instrument.

Figure 10:
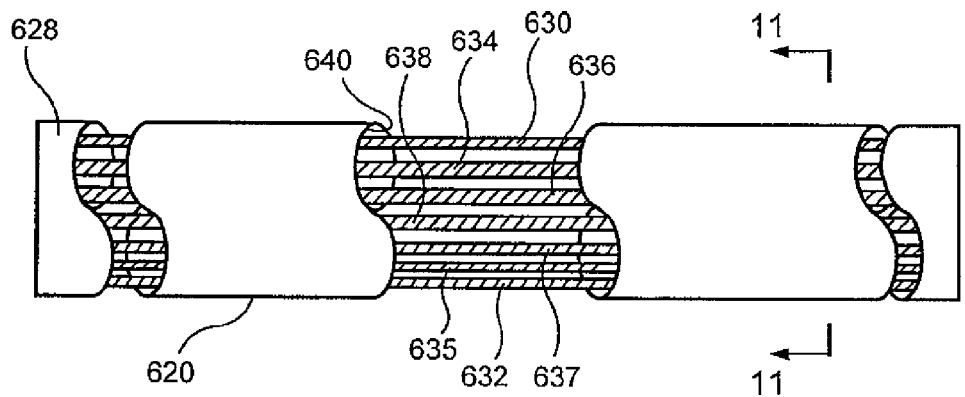
FIG. 10 is a side elevational view, partially in section, of a flexible shaft of the electro-mechanical surgical device illustrated in FIG. 2.
Figure 11:
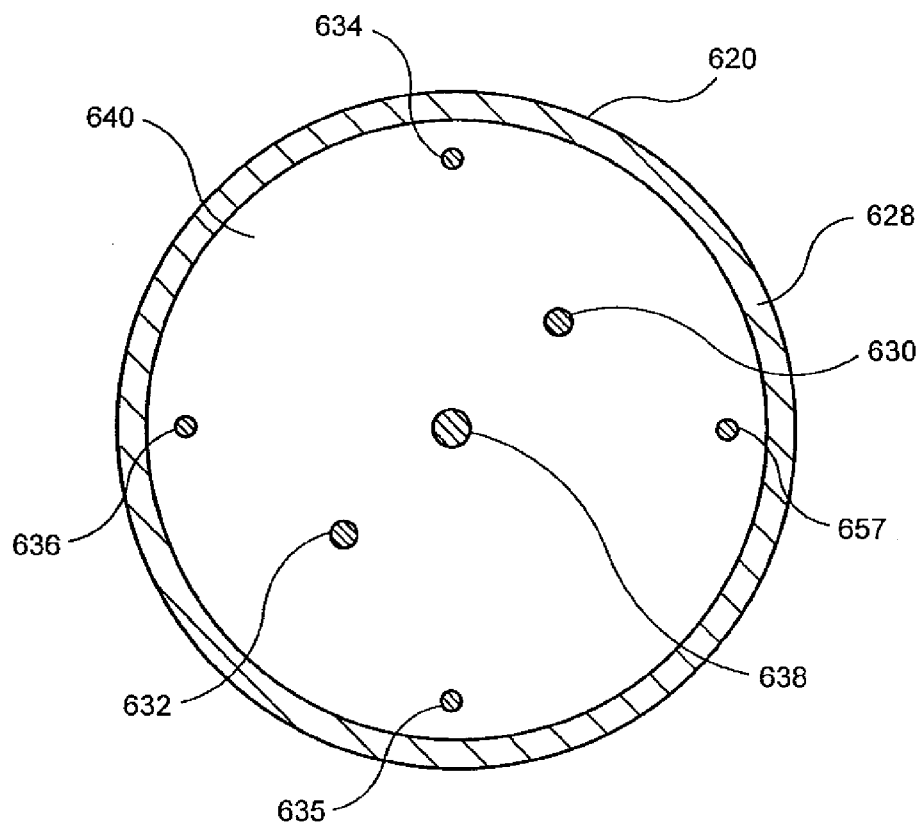
FIG. 11 is a cross-sectional view of the flexible shaft taken along the line 11-11 shown in FIG. 10.

Referring to FIG. 10, there is seen a side view, partially in section, of flexible shaft 620. According to one example embodiment, flexible shaft 620 includes a tubular sheath 628, which may include a coating or other sealing arrangement configured to provide a fluid-tight seal between the interior channel 640 thereof and the environment. Sheath 628 may be formed of a tissue-compatible, sterilizable elastomeric material. The sheath 628 may also be formed of a material that is autoclavable. Disposed within the interior channel 640 of flexible shaft 620, and extending along the entire length thereof, may be a first rotatable drive shaft 630, a second rotatable drive shaft 632, a first steering cable 634, a second steering cable 635, a third steering cable 636, a fourth steering cable 637 and a data transfer cable 638. FIG. 11 is a cross-sectional view of flexible shaft 620 taken along the line 11-11 illustrated in FIG. 10 and further illustrates the several cables 630, 632, 634, 635, 636, 637, 638. Each distal end of the steering cables 634, 635, 636, 637 is affixed to the distal end 624 of the flexible shaft 620. Each of the several cables 630, 632, 634, 635, 636, 637, 638 may be contained within a respective sheath.

The first rotatable drive shaft 630 and the second rotatable drive shaft 632 may be configured, for example, as highly flexible drive shafts, such as, for example, braided or helical drive cables. It should be understood that such highly flexible drive cables may have limited torque transmission characteristics and capabilities. It should also be understood that the surgical device 11, or other attachments connected to the flexible shaft 620, may require a higher torque input than the torque transmittable by the drive shafts 630, 632. The drive shafts 630, 632 may thus be configured to transmit low torque but high speed, the high-speed/low-torque being converted to low-speed/high-torque by gearing arrangements disposed, for example, at the distal end and/or the proximal end of the drive flexible shaft 620, in the surgical instrument or attachment and/or in the remote power console 612. It should be appreciated that such gearing arrangement(s) may be provided at any suitable location along the power train between the motors disposed in the housing 614 and the attached surgical instrument or other attachment connected to the flexible shaft 620. Such gearing arrangement(s) may include, for example, a spur gear arrangement, a planetary gear arrangement, a harmonic gear arrangement, cycloidal drive arrangement, an epicyclic gear arrangement, etc.

Figure 12:
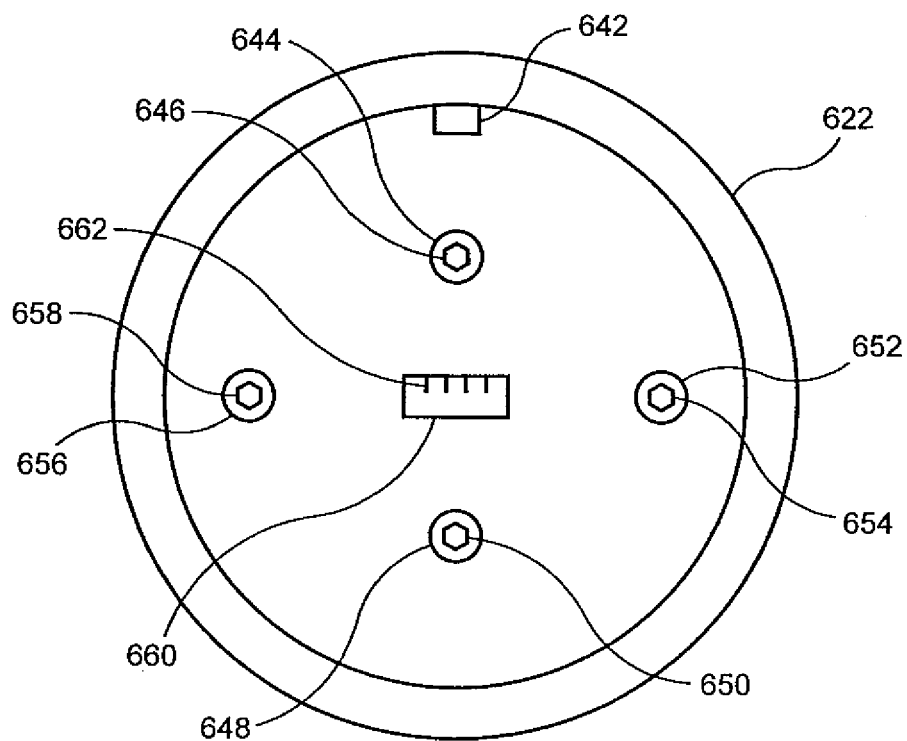
FIG. 12 is a rear end view of a first coupling of the flexible shaft illustrated in FIG. 10.

Referring now to FIG. 12, there is seen a rear end view of first coupling 622.

First coupling 622 includes a first connector 644, a second connector 648, a third connector 652 and a fourth connector 656, each rotatably secured to first coupling 622. Each of the connectors 644, 648, 652, 656 includes a respective recess 646, 650, 654, 658. As illustrated in FIG. 12, each recess 646, 650, 654, 658 may be hexagonally shaped. It should be appreciated, however, that the recesses 646, 650, 654, 658 may have any shape and configuration adapted to non-rotatably couple and rigidly attach the connectors 644, 648, 652, 656 to respective drive shafts of the motor arrangement contained within the housing 612. It should be appreciated that complementary projections may be provided on respective drive shafts of the motor arrangement to thereby drive the drive elements of the flexible shaft 620. It should also be appreciated that the recesses may be provided on the drive shafts and complementary projections may be provided on the connectors 644, 648, 652, 656. Any other coupling arrangement configured to non-rotatably and releasably couple the connectors 644, 648, 652, 656 and the drive shafts of the motor arrangement may be provided.

One of the connectors 644, 648, 652, 656 is non-rotatably secured to the first drive shaft 630, and another one of the connectors 644, 648, 652, 656 is non-rotatably secured to the second drive shaft 632. The remaining two of the connectors 644, 648, 652, 656 engage with transmission elements configured to apply tensile forces on the steering cables 634, 635, 636, 637 to thereby steer the distal end 624 of the flexible shaft 620. The data transfer cable 638 is electrically and logically connected with data connector 660. Data connector 660 includes, for example, electrical contacts 662, corresponding to and equal in number to the number of individual wires contained in the data cable 638. First coupling 622 includes a key structure 642 configured to properly orient the first coupling 622 to a mating and complementary coupling arrangement disposed on the housing 612. Such key structure 642 may be provided on either one, or both, of the first coupling 622 and the mating and complementary coupling arrangement disposed on the housing 612. First coupling 622 may include a quick-connect type connector, which may engage the first coupling 622 to the housing 612 by a simple pushing motion. Seals may be provided in conjunction with any of the several connectors 644, 648, 652, 656, 660 to provide a fluid-tight seal between the interior of first coupling 622 and the environment.

Figure 13:
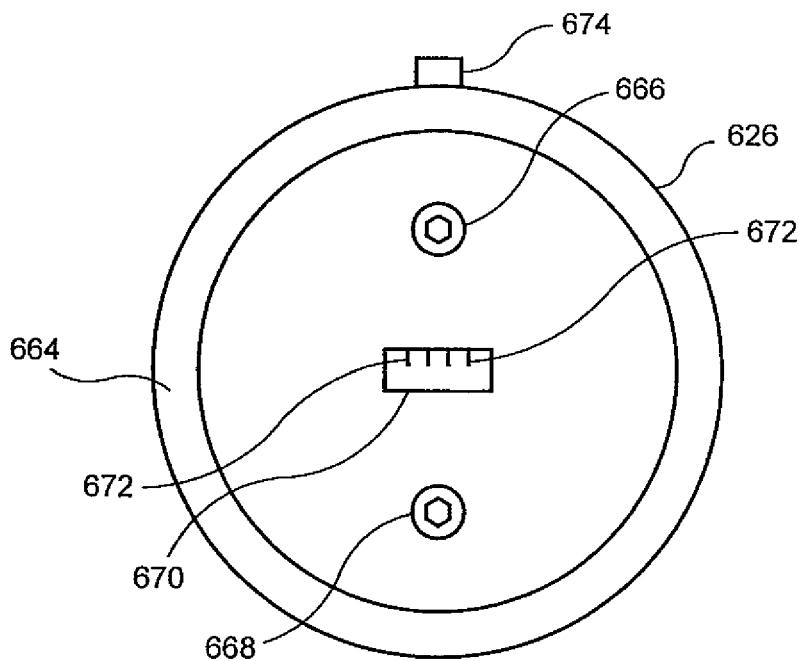
FIG. 13 is a front end view of a second coupling of the flexible shaft illustrated in FIG. 10.

Referring now to FIG. 13, there is seen a front end view of the second coupling 626 of flexible shaft 620. In the example embodiment, the second coupling 626 includes a first connector 666 and a second connector 668, each rotatably secured to the second coupling 626 and each non-rotatably secured to a distal end of a respective one of the first and second drive shafts 630, 632. A quick-connect type fitting 664 is provided on the second coupling 626 to detachably secure the device 11 thereto. The quick-connect type fitting 664 may be, for example, a rotary quick-connect type fitting, a bayonet type fitting, etc. A key structure 674 is provided on the second coupling 626 and configured to properly align the device 11 to the second coupling 626. The key structure or other arrangement configured to properly align the device 11 to the flexible shaft 620 may be provided on either one, or both, of the second coupling 626 and the device 11. In addition, the quick-connect type fitting may be provided on the device 11, as illustrated in FIG. 8(*a*) as the quick connect coupling 511. A data connector 670 having electrical contacts 672 is also provided in the second coupling 626. Like the data connector 660 of first coupling 622, the data connector 670 of second coupling 626 includes contacts 672 electrically and logically connected to the respective wires of data transfer cable 638 and contacts 662 of data connector 660. Seals may be provided in conjunction with the connectors 666, 668, 670 to provide a fluid-tight seal between the interior of second coupling 626 and the environment.

Disposed within housing 614 of the remote power console 612 are electro-mechanical driver elements configured to drive the drive shafts 630, 632 and the steering cables 634, 635, 636, 637 to thereby operate the electro-mechanical driver component 610 and the surgical device 11 attached to the second coupling 626. In the example embodiment illustrated schematically in FIG. 14, five electric motors 676, 680, 684, 690, 696, each operated via a power source, may be disposed in the remote power console 612. It should be appreciated, however, that any appropriate number of motors may be provided, and the motors may operate via battery power, line current, a DC power supply, an electronically controlled DC power supply, etc. It should also be appreciated that the motors may be connected to a DC power supply, which is in turn connected to line current and which supplies the operating current to the motors.

Figure 14:
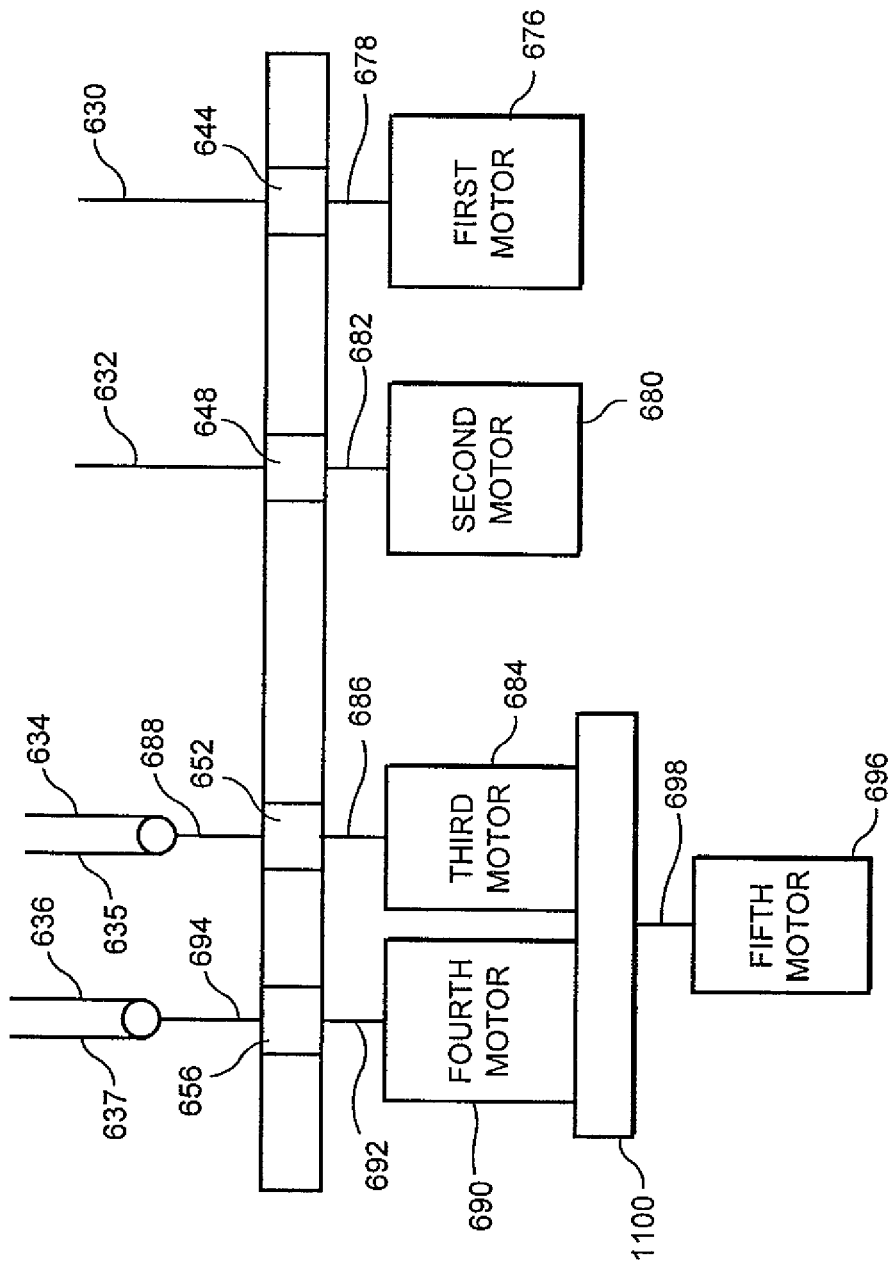
FIG. 14 is a schematic view of a motor arrangement of the electro-mechanical surgical system illustrated in FIG. 2.

FIG. 14 illustrates schematically one possible arrangement of motors. An output shaft 678 of a first motor 676 engages with the first connector 644 of the first coupling 622 when the first coupling 622, and, therefore, flexible shaft 620, is engaged with the housing 614 to thereby drive the first drive shaft 630 and first connector 666 of second coupling 626. Similarly, an output shaft 682 of a second motor 680 engages the second connector 648 of first coupling 622 when first coupling 622, and, therefore, flexible shaft 620 is engaged with the housing 614 to thereby drive the second drive shaft 632 and second connector 668 of second coupling 626. An output shaft 686 of a third motor 684 engages the third connector 652 of the first coupling 622 when the first coupling 622, and, therefore, flexible shaft 620, is engaged with the housing 614 to thereby drive the first and second steering cables 634, 635 via a first pulley arrangement 688. An output shaft 692 of a fourth motor 690 engages the fourth connector 656 of the first coupling 622 when the first coupling 622, and, therefore, flexible shaft 620, is engaged with the housing 614 to thereby drive the third and fourth steering cables 636, 637 via a second pulley arrangement 694. The third and fourth motors 684, 690 may be secured on a carriage 1100, which is selectively movable via an output shaft 698 of a fifth motor 696 between a first position and a second position to selectively engage and disengage the third and fourth motors 684, 690 with the respective pulley arrangement 688, 694 to thereby permit the flexible shaft 620 to become taut and steerable or limp as necessary. It should be appreciated that other mechanical, electrical and/or electro-mechanical mechanisms, etc., may be used to selectively engage and disengage the steering mechanism. The motors may be arranged and configured as described, for example, in U.S. patent application Ser. No. 09/510,923, entitled A Carriage Assembly for Controlling a Steering Wire Mechanism Within a Flexible Shaft," (now U.S. Pat. No. 6,517,565) which is expressly incorporated herein in its entirety by reference thereto.

It should be appreciated that any one or more of the motors 676, 680, 684, 690, 696 may be, for example, a high-speed/low-torque motor, a low-speed/high-torque motor, etc. As indicated above, the first rotatable drive shaft 630 and the second rotatable drive shaft 632 may be configured to transmit high speed and low torque. Thus, the first motor 676 and the second motor 680 may be configured as high-speed/low-torque motors. Alternatively, the first motor 676 and the second motor 680 may be configured as low-speed/high-torque motors with a torque-reducing/speed-increasing gear arrangement disposed between the first motor 676 and the second motor 680 and a respective one of the first rotatable drive shaft 630 and the second rotatable drive shaft 632. Such torque-reducing/speed-increasing gear arrangements may include, for example, a spur gear arrangement, a planetary gear arrangement, a harmonic gear arrangement, cycloidal drive arrangement, an epicyclic gear arrangement, etc. It should be appreciated that any such gear arrangement may be disposed within the remote power console 612 or in the proximal end of the flexible shaft 620, such as, for example, in the first coupling 622. It should be appreciated that the gear arrangement(s) may be provided at the distal and/or proximal ends of the first rotatable drive shaft 630 and/or the second rotatable drive shaft 632 to prevent windup and breakage thereof.

Figure 15:
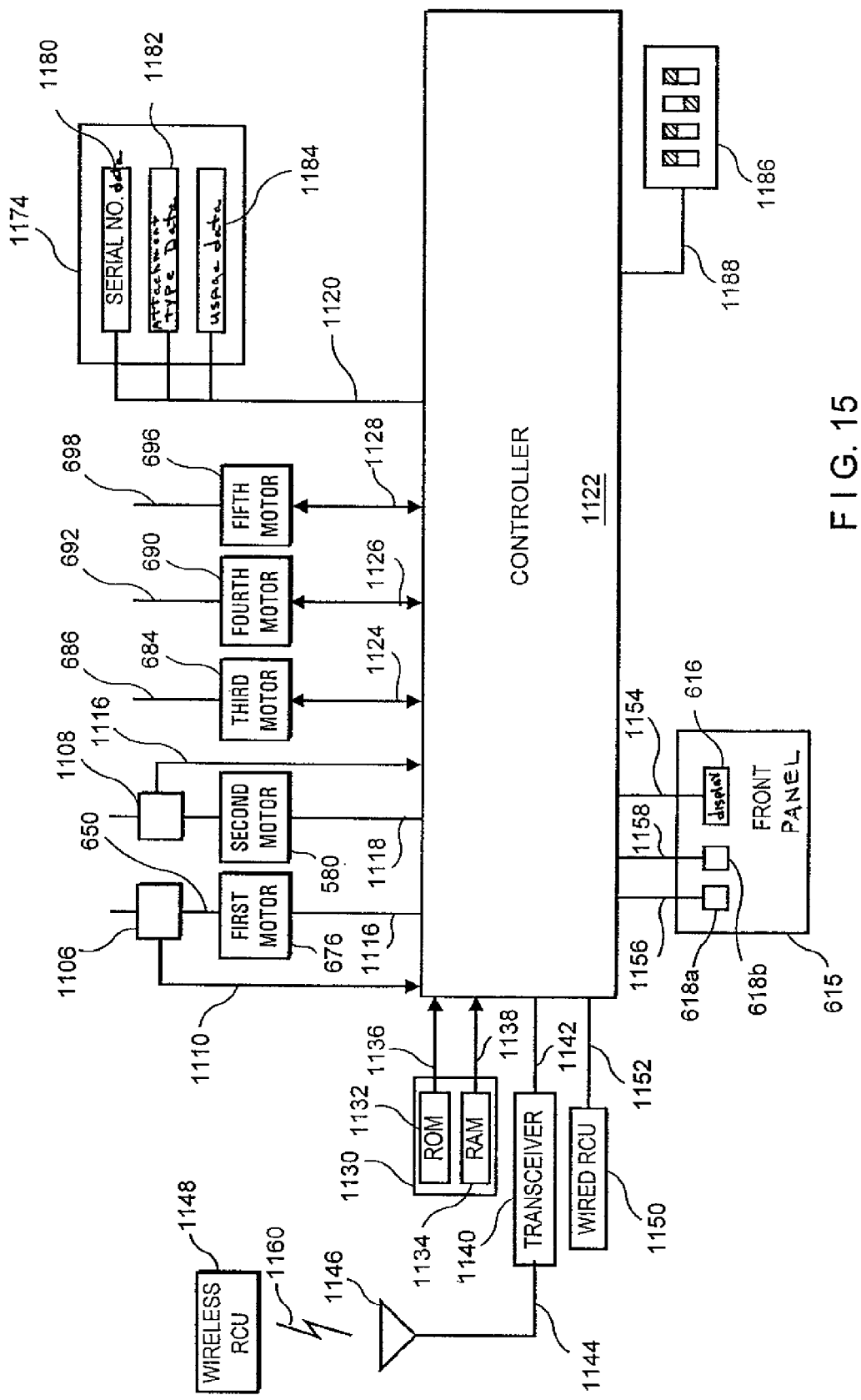
FIG. 15 is a schematic view of the electro-mechanical surgical system illustrated in FIG. 2.

Referring now to FIG. 15, there is seen a schematic view of the electro-mechanical driver component 610. A controller 1122 is provided in the housing 614 of remote power console 612 and is configured to control all functions and operations of the electro-mechanical driver component 610 and the linear clamping, cutting and stapling device 11 or other surgical instrument or attachment attached to the flexible shaft 620. A memory unit 1130 is provided and may include memory devices, such as, a ROM component 1132, a RAM component 1134, etc. ROM component 1132 is in electrical and logical communication with controller 1122 via line 1136, and RAM component 1134 is in electrical and logical communication with controller 1122 via line 1138. RAM component 1134 may include any type of random-access memory, such as, for example, a magnetic memory device, an optical memory device, a magneto-optical memory device, an electronic memory device, etc. Similarly, ROM component 1132 may include any type of read-only memory, such as, for example, a removable memory device, such as a PC-Card or PCMCIA-type device. It should be appreciated that ROM component 1132 and RAM component 1134 may be configured as a single unit or may be separate units and that ROM component 1132 and/or RAM component 1134 may be provided in the form of a PC-Card or PCMCIA-type device.

Controller 1122 is further connected to front panel 615 of housing 614 and, more particularly, to display device 616 via line 1154 and indicators 618a, 618b via respective lines 1156, 1158. Lines 1116, 1118, 1124, 1126, 1128 electrically and logically connect controller 1122 to first, second, third, fourth and fifth motors 676, 680, 684, 690, 696, respectively. A wired remote control unit ("RCU") 1150 is electrically and logically connected to controller 1122 via line 1152. A wireless RCU 1148 is also provided and communicates via a wireless link 1160 with a receiving/sending unit 1146 connected via line 1144 to a transceiver 1140. The transceiver 1140 is electrically and logically connected to controller 1122 via line 1142. Wireless link 1160 may be, for example, an optical link, such as an infrared link, a radio link or any other form of wireless communication link.

A switch device 1186, which may include, for example, an array of DIP switches, may be connected to controller 1122 via line 1188. Switch device 1186 may be configured, for example, to select one of a plurality of languages used in displaying messages and prompts on the display device 616. The messages and prompts may relate to, for example, the operation and/or the status of the electro-mechanical driver component 610 and/or to the surgical device 11 attached thereto.

According to the example embodiment of the present invention, a first encoder 1106 is provided within the second coupling 626 and is configured to output a signal in response to and in accordance with the rotation of the first drive shaft 630. A second encoder 1108 is also provided within the second coupling 626 and is configured to output a signal in response to and in accordance with the rotation of the second drive shaft 632. The signal output by each of the encoders 1106, 1108 may represent the rotational position of the respective drive shaft 630, 632 as well as the rotational direction thereof. Such encoders 1106, 1108 may include, for example, Hall-effect devices, optical devices, etc. Although the encoders 1106, 1108 are described as being disposed within the second coupling 626, it should be appreciated that the encoders 1106, 1108 may be provided at any location between the motor system and the surgical device 11. It should be appreciated that providing the encoders 1106, 1108 within the second coupling 626 or at the distal end of the flexible shaft 620 may provide an accurate determination of the drive shaft rotation. If the encoders 1106, 1108 are disposed at the proximal end of the flexible shaft 620, windup of the first and second rotatable drive shafts 630, 632 may result in measurement error.

Figure 16:
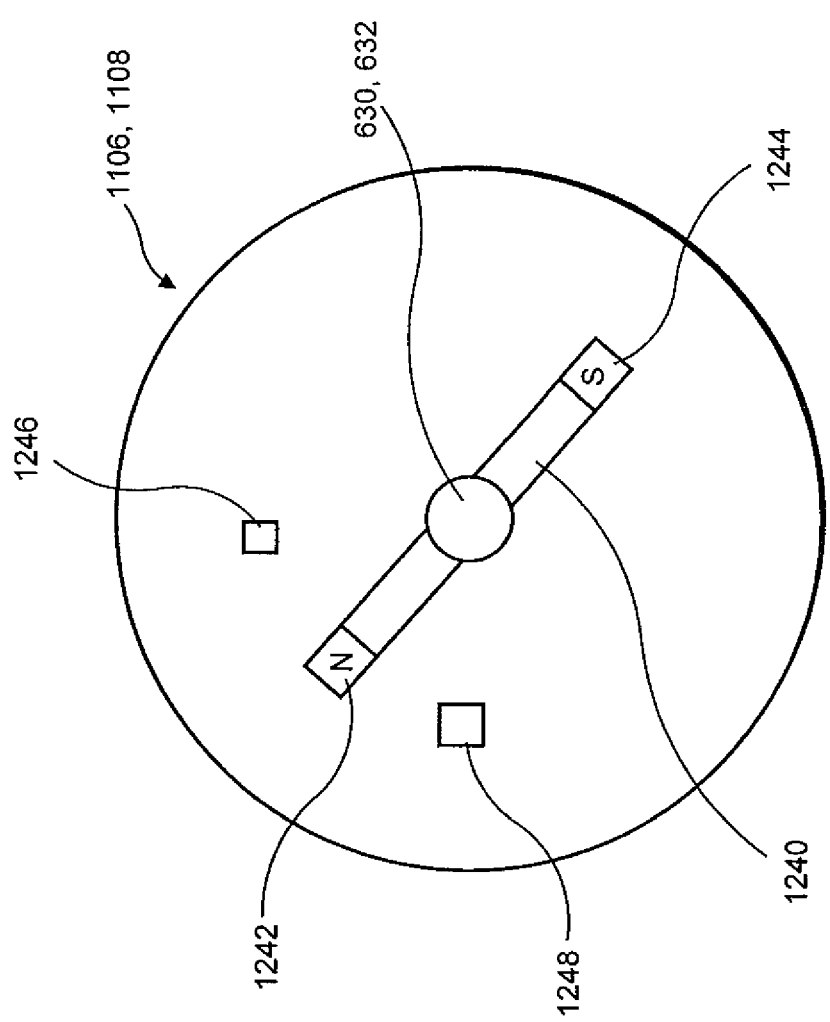
FIG. 16 is a schematic view of an encoder of the flexible shaft illustrated in FIG. 10.

FIG. 16 is a schematic view of an encoder 1106, 1108, which includes a Hall-effect device. Mounted non-rotatably on drive shaft 630, 632 is a magnet 1240 having a north pole 1242 and a south pole 1244. The encoder 1106, 1108 further includes a first sensor 1246 and second sensor 1248, which are disposed approximately 90° apart relative to the longitudinal, or rotational, axis of drive shaft 630, 632. The output of the sensors 1246, 1248 is persistent and changes its state as a function of a change of polarity of the magnetic field in the detection range of the sensor. Thus, based on the output signal from the encoders 1106, 1108, the angular position of the drive shaft 630, 632 may be determined within one-quarter revolution and the direction of rotation of the drive shaft 630, 632 may be determined. The output of each encoder 1106, 1108 is transmitted via a respective line 1110, 1112 of data transfer cable 638 to controller 1122. The controller 1122, by tracking the angular position and rotational direction of the drive shafts 630, 632 based on the output signal from the encoders 1106, 1108, may thereby determine the position and/or state of the components of the surgical device connected to the electro-mechanical driver component 610. That is, by counting the revolutions of the drive shaft 630, 632, the controller 1122 may determine the position and/or state of the components of the surgical device connected to the electro-mechanical driver component 610.

For example, the advancement distance between the first jaw 80 and the second jaw 50 and the thrust plate 502 are functions of, and ascertainable on the basis of, the rotation of the respective drive shafts 630, 632. By ascertaining an absolute position of the second jaw 50 and the thrust plate 502 at a point in time, the relative displacement of the second jaw 50 and the thrust plate 502, based on the output signal from the encoders 1106, 1108 and the known pitches of the screw 521 and of the screws 503 and 504, may be used to ascertain the absolute position of the first jaw 80 and the thrust plate 502 at all times thereafter. The absolute position of the second jaw 50 and the thrust plate 502 may be fixed and ascertained at the time that the surgical device 11 is first coupled to the flexible shaft 620. Alternatively, the position of the second jaw 50 and the thrust plate 502 relative to, for example, the first jaw 80 may be determined based on the output signal from the encoders 1106, 1108.

The surgical device 11 may further include, as illustrated in FIG. 8(a), a data connector 1272 adapted by size and configuration to electrically and logically connect to connector 670 of second coupling 626. In the example embodiment, data connector 1272 includes contacts equal in number to the number of leads 672 of connector 670. The memory module 501 is electrically and logically connected with the data connector 1272. Memory module 501 may be in the form of, for example, an EEPROM, EPROM, etc. and may be contained, for example, within the second jaw 50 of the surgical device 11.

Figure 17:
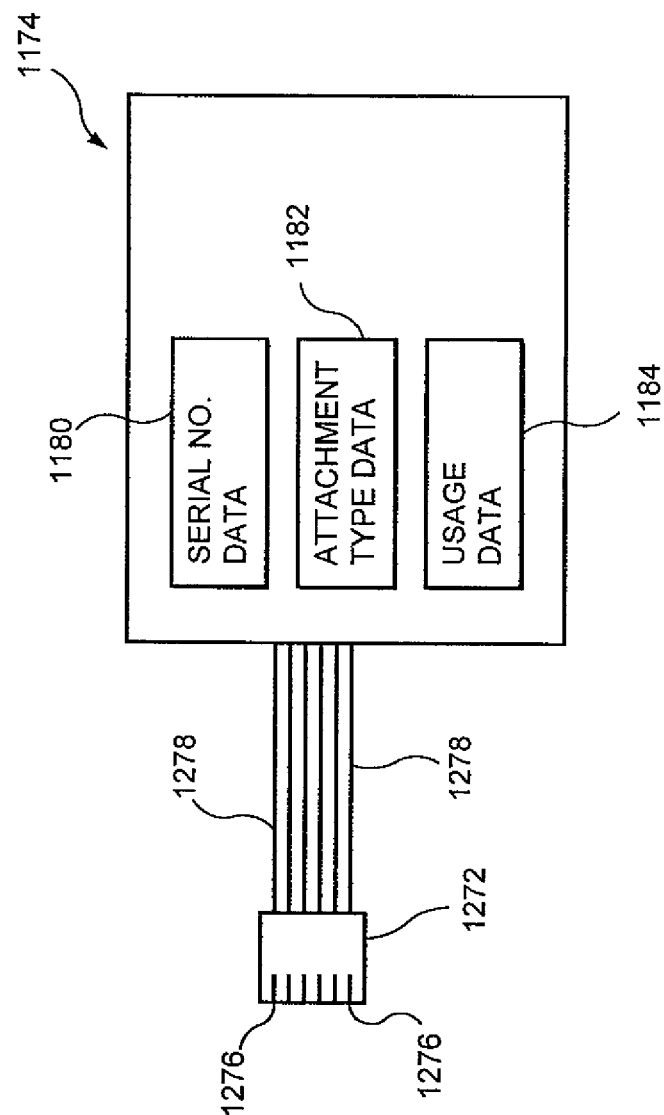
FIG. 17 is a schematic view of a memory device of a linear clamping, cutting and stapling device according to one example embodiment of the present invention.

FIG. 17 schematically illustrates the memory module 501. As seen in FIG. 17, data connector 1272 includes contacts 1276, each electrically and logically connected to the memory module 501 via a respective line 1278. The memory module 501 may be configured to store, for example, a serial number data 1180, an attachment type identifier (ID) data 1182 and a usage data 1184. The memory module 501 may additionally store other data. Both the serial number data 1180 and the ID data 1182 may be configured as read-only data. The serial number data 1180 and/or the ID data 1182 may be stored in a read-only section of the memory module 501. In the example embodiment, serial number data 1180 may be data uniquely identifying the particular surgical device, whereas the ID data 1182 may be data identifying the type of the attachment, such as, for example, in a system 610 in which other types of surgical instruments or attachments are attachable thereto. The usage data 1184 represents usage of the particular attachment, such as, for example, the number of times the first jaw 80 of the surgical device 11 has been opened and closed, or the number of times that the thrust plate of the surgical device 11 has been advanced. The usage data 1184 may be stored in a read/write section of the memory module 501.

It should be appreciated that the attachment attachable to the distal end 624 of the flexible shaft 620, e.g., surgical device 11, may be designed and configured to be used a single time or multiple times. The attachment may also be designed and configured to be used a predetermined number of times. Accordingly, the usage data 1184 may be used to determine whether the surgical device 11 has been used and whether the number of uses has exceeded the maximum number of permitted uses. As more fully described below, an attempt to use the attachment after the maximum number of permitted uses has been reached will generate an ERROR condition.

Referring again to FIG. 15, the controller 1122 is configured to read the ID data 1182 from the memory module 501 of the surgical device 11 when the surgical device 11 is initially connected to the flexible shaft 620. The memory module 501 is electrically and logically connected to the controller 1122 via the line 1120 of the data transfer cable 638. Based on the read ID data 1182, the controller 1122 is configured to read or select from the memory unit 1130, an operating program or algorithm corresponding to the type of surgical instrument or attachment connected to the flexible shaft 620. The memory unit 1130 is configured to store the operating programs or algorithms for each available type of surgical instrument or attachment, the controller 1122 selecting and/or reading the operating program or algorithm from the memory unit 1130 in accordance with the ID data 1182 read from the memory module 501 of an attached surgical instrument or attachment. As indicated above, the memory unit 1130 may include a removable ROM component 1132 and/or RAM component 1134. Thus, the operating programs or algorithms stored in the memory unit 1130 may be updated, added, deleted, improved or otherwise revised as necessary. The operating programs or algorithms stored in the memory unit 1130 may be customizable based on, for example, specialized needs of the user. A data entry device, such as, for example, a keyboard, a mouse, a pointing device, a touch screen, etc., may be connected to the memory unit 1130 via, for example, a data connector port, to facilitate the customization of the operating programs or algorithms. Alternatively or additionally, the operating programs or algorithms may be customized and preprogrammed into the memory unit 1130 remotely from the electro-mechanical driver component 610. It should be appreciated that the serial number data 1180 and/or usage data 1184 may also be used to determine which of a plurality of operating programs or algorithms is read or selected from the memory unit 1130. It should be appreciated that the operating program or algorithm may alternatively be stored in the memory module 501 of the surgical device 11 and transferred to the controller 1122 via the data transfer cable 638. Once the appropriate operating program or algorithm is read by or selected by or transmitted to, the controller 1122, the controller 1122 causes the operating program or algorithm to be executed in accordance with operations performed by the user via the wired RCU 1150 and/or the wireless RCU 1148. As indicated hereinabove, the controller 1122 is electrically and logically connected with the first, second, third, fourth and fifth motors 676, 680, 684, 690, 696 via respective lines 1116, 1118, 1124, 1126, 1128 and is configured to control such motors 676, 680, 684, 690, 696 in accordance with the read, selected or transmitted operating program or algorithm via the respective lines 1116, 1118, 1124, 1126, 1128.

Figure 18:
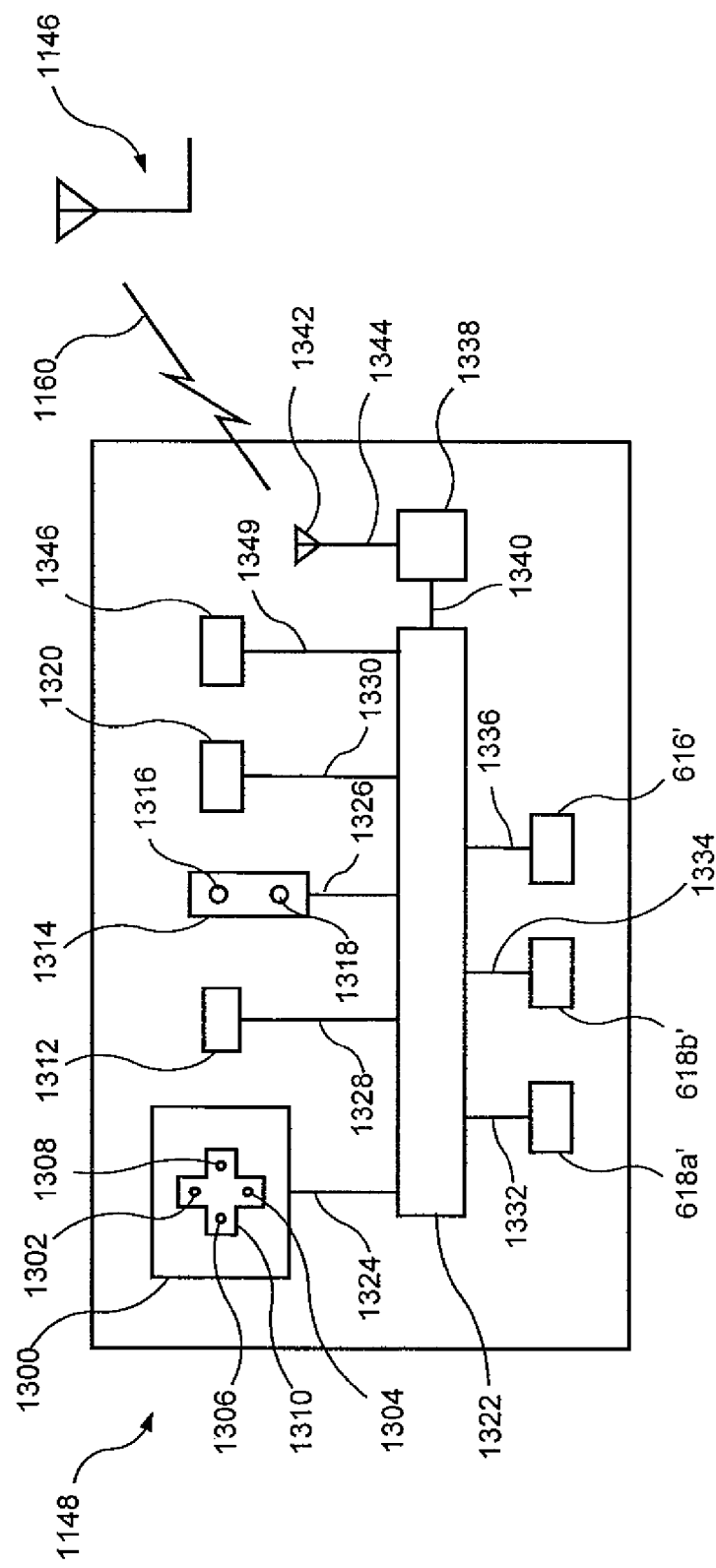
FIG. 18 is a schematic view of a wireless remote control unit of the electro-mechanical surgical system illustrated in FIG. 2.

Referring now to FIG. 18, there is seen a schematic view of wireless RCU 1148. Wireless RCU 1148 includes a steering controller 1300 having a plurality of switches 1302, 1304, 1306, 1308 arranged under a four-way rocker 1310. The operation of switches 1302, 1304, via rocker 1310, controls the operation of first and second steering cables 634, 635 via third motor 684. Similarly, the operation of switches 1306, 1308, via rocker 1310, controls the operation of third and fourth steering cables 636, 637 via fourth motor 692. It should be appreciated that rocker 1310 and switches 1302, 1304, 1306, 1308 are arranged so that the operation of switches 1302, 1304 steers the flexible shaft 620 in the north-south direction and that the operation of switches 1306, 1308 steers the flexible shaft 620 in the east-west direction. Reference herein to north, south, east and west is made to a relative coordinate system. Alternatively, a digital joystick, an analog joystick, etc. may be provided in place of rocker 1310 and switches 1302, 1304, 1306, 1308. Potentiometers or any other type of actuator may also be used in place of switches 1302, 1304, 1306, 1308.

Wireless RCU 1148 further includes a steering engage/disengage switch 1312, the operation of which controls the operation of fifth motor 696 to selectively engage and disengage the steering mechanism. Wireless RCU 1148 also includes a two-way rocker 1314 having first and second switches 1316, 1318 operable thereby. The operation of these switches 1316, 1318 controls certain functions of the electro-mechanical driver component 610 and any surgical instrument or attachment, such as the surgical device 11, attached to the flexible shaft 620 in accordance with the operating program or algorithm corresponding to the attached device 11. For example, operation of the two-way rocker 1314 may control the opening and closing of the first jaw 80 and the second jaw 50 of the surgical device 11. Wireless RCU 1148 is provided with yet another switch 1320, the operation of which may further control the operation of the electro-mechanical driver component 610 and the device attached to the flexible shaft 620 in accordance with the operating program or algorithm corresponding to the attached device. For example, operation of the switch 1320 may initiate the advancement of the thrust plate 502 of the surgical device 11.

Wireless RCU 1148 includes a controller 1322, which is electrically and logically connected with the switches 1302, 1304, 1306, 1308 via line 1324, with the switches 1316, 1318 via line 1326, with switch 1312 via line 1328 and with switch 1320 via line 1330. Wireless RCU 1148 may include indicators 618a', 618b', corresponding to the indicators 618a, 618b of front panel 615, and a display device 616', corresponding to the display device 616 of the front panel 615. If provided, the indicators 618a', 618b' are electrically and logically connected to controller 1322 via respective lines 1332, 1334, and the display device 616' is electrically and logically connected to controller 1322 via line 1336. Controller 1322 is electrically and logically connected to a transceiver 1338 via line 1340, and transceiver 1338 is electrically and logically connected to a receiver/transmitter 1342 via line 1344. A power supply, for example, a battery, may be provided in wireless RCU 1148 to power the same. Thus, the wireless RCU 1148 may be used to control the operation of the electro-mechanical driver component 610 and the device 11 attached to the flexible shaft 620 via wireless link 1160.

Wireless RCU 1148 may include a switch 1346 connected to controller 1322 via line 1348. Operation of switch 1346 transmits a data signal to the transmitter/receiver 1146 via wireless link 1160. The data signal includes identification data uniquely identifying the wireless RCU 1148. This identification data is used by the controller 1122 to prevent unauthorized operation of the electro-mechanical driver component 610 and to prevent interference with the operation of the electro-mechanical driver component 610 by another wireless RCU. Each subsequent communication between the wireless RCU 1148 and the electro-mechanical device surgical 610 may include the identification data. Thus, the controller 1122 may discriminate between wireless RCUs and thereby allow only a single, identifiable wireless RCU 1148 to control the operation of the electro-mechanical driver component 610 and the device 11 attached to the flexible shaft 620.

Based on the positions of the components of the device attached to the flexible shaft 620, as determined in accordance with the output signals from the encoders 1106, 1108, the controller 1122 may selectively enable or disable the functions of the electro-mechanical driver component 610 as defined by the operating program or algorithm corresponding to the attached device. For example, for the surgical device 11, the firing function controlled by the operation of the switch 1320 is disabled unless the space or gap between second jaw 50 and first jaw 80 is determined to be within an acceptable range.

Figure 19:
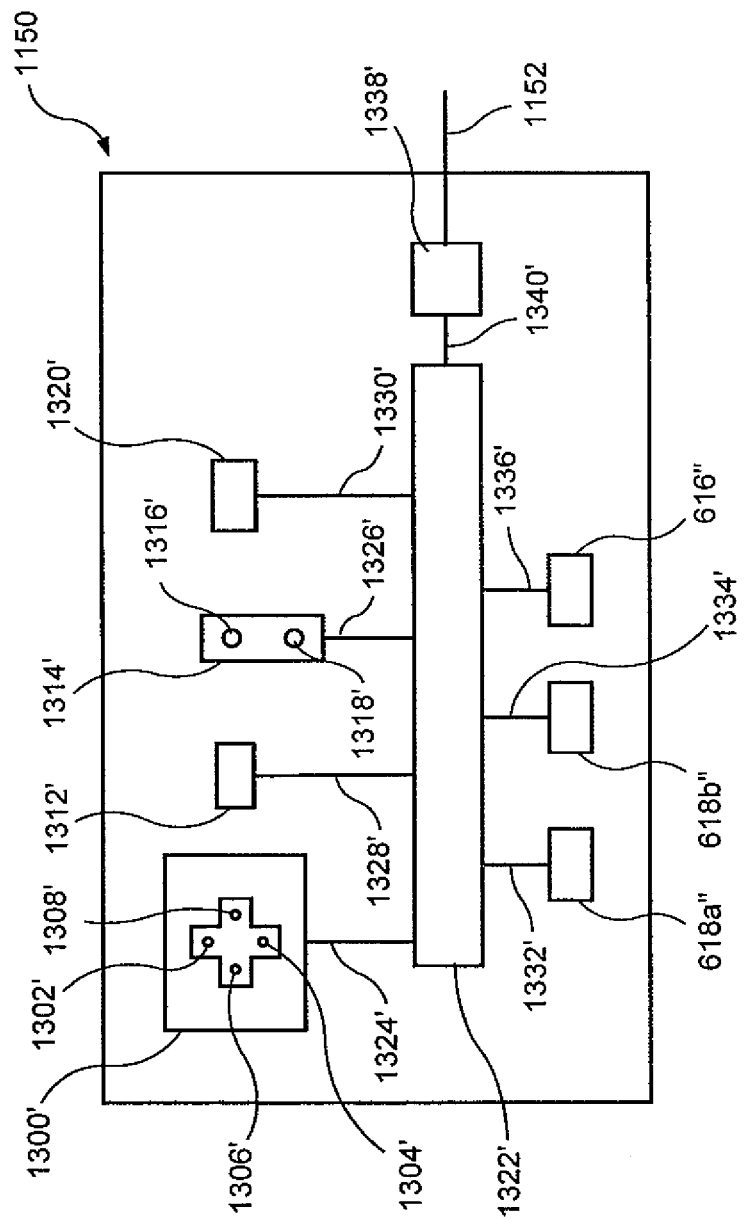
FIG. 19 is a schematic view of a wired remote control unit of the electro-mechanical surgical system illustrated in FIG. 2.

Referring now to FIG. 19, there is seen a schematic view of a wired RCU 1150. In the example embodiment, wired RCU 1150 includes substantially the same control elements as the wireless RCU 1148 and further description of such elements is omitted. Like elements are indicated in FIG. 19 with an accompanying prime. It should be appreciated that the functions of the electro-mechanical driver component 610 and the device attached to the flexible shaft 620, e.g., the surgical device 11, may be controlled by the wired RCU 1150 and/or by the wireless RCU 1148. In the event of a battery failure, for example, in the wireless RCU 1148, the wired RCU 1150 may be used to control the functions of the electro-mechanical driver component 610 and the device attached to the flexible shaft 620.

As described hereinabove, the front panel 615 of housing 614 includes display device 616 and indicators 618*a*, 618*b*. The display device 616 may include an alpha-numeric display device, such as an LCD display device. Display device 616 may also include an audio output device, such as a speaker, a buzzer, etc. The display device 616 is operated and controlled by controller 1122 in accordance with the operating program or algorithm corresponding to the device attached to the flexible shaft 620, e.g., the surgical device 11. If no surgical instrument or attachment is so attached, a default operating program or algorithm may be read by or selected by or transmitted to controller 1122 to thereby control the operation of the display device 616 as well as the other aspects and functions of the electro-mechanical driver component 610. If surgical device 11 is attached to flexible shaft 620, display device 616 may display, for example, data indicative of the gap between second jaw 50 and first jaw 80 as determined in accordance with the output signal of encoders 1106, 1108, as more fully described hereinabove.

Similarly, the indicators 618*a*, 618*b* are operated and controlled by controller 1122 in accordance with the operating program or algorithm corresponding to the device 11, attached to the flexible shaft 620, e.g., the surgical device 11. Indicator 618*a* and/or indicator 618*b* may include an audio output device, such as a speaker, a buzzer, etc., and/or a visual indicator device, such as an LED, a lamp, a light, etc. If the surgical device 11 is attached to the flexible shaft 620, indicator 618*a* may indicate, for example, that the electro-mechanical driver component 610 is in a power ON state, and indicator 618*b* may, for example, indicate whether the gap between second jaw 50 and first jaw 80 is determined to be within the acceptable range. It should be appreciated that although two indicators 618*a*, 618*b* are described, any number of additional indicators may be provided as necessary. Additionally, it should be appreciated that although a single display device 616 is described, any number of additional display devices may be provided as necessary.

The display device 616' and indicators 618*a*', 618*b*' of wired RCU 1150 and the display device 616" and indicators 618*a*", 618*b*" of wireless RCU 1148 are similarly operated and controlled by respective controller 1322, 1322' in accordance with the operating program or algorithm of the device attached to the flexible shaft 620.

As described above, the surgical device 11 may be configured to clamp, cut and staple a section of tissue. The operation of device 11 will now be described in connection with the removal of a cancerous or anomalous section of tissue in a patient's bowel, which is merely one type of tissue and one type of surgery that may be performed using the surgical device 11. Generally, in operation, after the cancerous or anomalous tissue in the gastrointestinal tract has been located, the patient's abdomen is initially opened to expose the bowel. In accordance with remote actuation provided by the electro-mechanical driver component 610, the first and second jaws 50, 80 of the surgical device 11 are driven into the open position by the first driver. As described above, the surgical device 11 may be initially maintained in the open position, thereby eliminating the need to initially drive the surgical device 11 into the open position. The tube of the bowel on a side adjacent to the cancerous tissue is placed between the open first jaw 80 and second jaw 50. By remote actuation, the first driver is engaged in reverse, and the first jaw 80 closes against the second jaw 50, clamping the section of bowel therebetween. Once the bowel has been sufficiently clamped, the second driver is engaged, which causes the thrust plate (having the staple pusher and the knife mounted thereto) to move between a first position as illustrated in FIG. 5 and a second position as illustrated in FIG. 6, thereby cutting and stapling the bowel. The second driver is then engaged in reverse, which causes the staple pusher and the knife to move back into the first position as illustrated in FIG. 5. The first driver is then engaged to drive the first jaw 80 and the second jaw 50 of the surgical device 11 back into the open position. These steps are then repeated on the other side of the cancerous tissue, thereby removing the section of bowel containing the cancerous tissue, which is stapled on either end to prevent spilling of bowel material into the open abdomen.

More specifically, according to the example embodiment of the present invention, the surgical device 11 is coupled to the attachment coupling 626 of the electro-mechanical driver component 610 such that the first drive socket 180 engages the first drive shaft 630 of the electro-mechanical driver component 610 and the second drive socket 310 engages the second drive shaft 632 of the electro-mechanical driver component 610. Thus, rotation of the pinion 508*a* is effected by rotation of the first drive socket 180 which is effected by rotation of the corresponding drive shaft 630 of the electro-mechanical driver component 610. Clockwise or counter-clockwise rotation of the pinion 508*a* is achieved depending on the direction of rotation of the motor 680. The rotation of the pinion 508*b* is effected by rotation of the second drive socket 310 which is effected by rotation of the corresponding drive shaft 632 of the electro-mechanical driver component 610. Clockwise or counter-clockwise rotation of the pinion 508*b* is achieved depending on the direction of the motor 676.

When the surgical device 11 is in an initial closed position as illustrated in FIG. 4, the first motor 680 is operated in order to place the surgical device in the open position. Specifically, the first motor 680 corresponding to the first drive shaft 630 is activated, which engages the first drive socket 180, thereby causing the pinion 508*a* to turn in a first, e.g., counter-clockwise, rotation direction. Since the circumferentially-disposed gear teeth 5083 of the pinion 508*a* are engaged with the circumferentially-disposed gear teeth 5291 of the spur gear 529*a*, the rotation of the pinion 508*a* causes the spur gear to rotate in a first, e.g., clockwise, direction which is opposite to the direction of rotation of the pinion 508a. The internal bore 5293 of the first spur gear 529a engages the end 5231 of the first worm 523a so as to cause the first worm 523a to rotate in the same direction as that of the first spur gear 529a, e.g., clockwise. The thread(s) 5233 of worm 523a engage the gear teeth 5221 of worm gear 522 so as to cause rotation of the worm gear 522 in a first, e.g., counter-clockwise when viewed from the top, direction. The internal bore 5222 of the worm gear 522 engages the portion 5212 of the head 5211 of the screw 521, thereby causing the screw 521 to rotate in a first, e.g., counter-clockwise when viewed from the top, direction. The externally-disposed thread(s) 5214 of the screw 521 engage the threads of the internally-threaded bore 5051 of the anvil 505, thereby causing anvil 505 to move in a downward direction, e.g., away from the frame housing 506. Thus, the second jaw 50 is opened in a continuous fashion. In the embodiment illustrated, the second jaw is opened in parallel alignment, e.g., in a plane, with the first jaw 80, and begins separating from the first jaw 80. Continuous operation of the motor in this manner eventually places the surgical device 11 in an open state, providing a space between the first jaw 80 and the second jaw 50, as illustrated in FIG. 3.

Next, the staple retainer 540 that is attached to the lower parallel edges 5066 of the frame housing 506 or to a bottom surface of the staple holder 513 is removed. According to one example embodiment, the staple holder is configured to be removed by pulling up the lever 5182 of the pin 518 so as to lift the end 5181 of the pin 518 out of the through-hole 5401 of the staple retainer 540. The grip region 5403 of the staple retainer 540 may be gripped and the staple retainer 540 may be pulled off of the surgical device 11. Next, a section of tissue is placed between the first jaw 80 and second jaw 50. With the staple holder 540 removed from the surgical device 11 and with the section of tissue disposed between the first jaw 80 and the second jaw 50, the end 5181 of the pin 518 is inserted into the orifice 5057 of the anvil 505 and maintained in the inserted position in accordance with the bias of spring 524 to maintain the section of tissue between the jaws.

The first motor 680 is operated in reverse in order to place the surgical device in the closed position. Specifically, the first motor 680 corresponding to the first drive shaft 630 is activated, which engages the first drive socket 180, thereby causing the pinion 508a to turn in a second, e.g., clockwise, direction of rotation. Since the circumferentially-disposed gear teeth 5083 of the pinion 508a are engaged with the circumferentially-disposed gear teeth 5291 of the spur gear 529a, the rotation of the pinion 508a causes the spur gear 529a to rotate in a second, e.g., counter-clockwise direction which is opposite to the direction of rotation of the pinion 508a. The internal bore 5293 of the first spur gear 529a is engaged with the end 5231 of the first worm gear 523a, such that the rotation of the first spur gear 529a causes the first worm 523a to rotate in the same direction as the first spur gear 529a, e.g., counter-clockwise. The thread(s) 5233 of the worm gear 523a are engaged with the worm gear teeth 5221 of worm gear 522, such that the rotation of the first worm 523a causes rotation of the worm gear 522 in a second, e.g., clockwise when viewed from the top, direction. The internal bore 5222 of the worm gear 522 is engaged with the portion 5212 of the head 5211 of the screw 521, such that the rotation of the worm gear 522 causes the screw 521 to rotate in a second, e.g., clockwise when viewed from the top, direction. The externally-disposed thread(s) 5214 of the screw 521 are engaged with the threads of the internally-threaded bore 5051 of the anvil 505, such that the rotation of the screw 521 causes anvil 505 to move in an upward direction, e.g., toward the frame housing 506. Thus, the second jaw 50 is closed in a continuous fashion and begins approaching the first jaw 80. Continuous operation of the motor in this manner eventually places the surgical device 11 in a closed state, as illustrated in FIG. 4, wherein the tissue is clamped between the first jaw 80 and the second jaw 50. In this closed state, the section of tissue to be stapled and cut is clamped between the pair of parallel-disposed edges 5253a and 5253b of the staple holder 513 and the region 5054 of the anvil 505.

To begin the stapling and cutting procedure, the second motor 676 is actuated in order to move the thrust plate 502 from a first, raised, e.g., retracted, position to a second, lowered, e.g., extended, position. Specifically, the second motor 676 corresponding to the second drive shaft 632 is activated. The second drive shaft 632 is engaged with the second drive socket 310, such that rotation of the second drive shaft 632 in a first direction, e.g., counter-clockwise, causes the pinion 508b to rotate in a first, e.g., counter-clockwise, direction of rotation. The circumferentially-disposed gear teeth 5086 of the pinion 508b are engaged with the circumferentially-disposed gear teeth 5292 of the spur gear 529b, such that the rotation of the pinion 508b causes the spur gear 529b to rotate in a first, e.g., clockwise, direction which is opposite to the direction of rotation of the pinion 508b. The internal bore 5294 of the spur gear 529b is engaged with the end 5234 of the second worm gear 523b, such that the rotation of the spur gear 529b causes the second worm 523b to rotate in the same direction as that of the first spur gear 529b, e.g., clockwise. The threads 5236 of the worm 523b are engaged with the worm gear teeth 5161 of worm gear 516, such that rotation of the second worm 523b causes rotation of the worm gear 516 in a first, e.g., counter-clockwise when viewed from the top, direction. The thread(s) of the internally-threaded bore 5164 of the worm gear 516 are engaged with the thread(s) of the screw 504. Because the screw 504 is non-rotatably coupled to the thrust plate 502, screw 504 and thrust plate 502 move together in a downward direction. Simultaneously, the threads 5236 of the worm 523b are engaged with the worm gear teeth 5171 of the worm gear 517, such that the rotation of the worm 523b causes rotation of the worm gear 517 in a first, e.g., clockwise when viewed from the top, direction. The thread(s) of the internally-threaded bore 5174 of the worm gear 517 engages the thread(s) of the screw 503. Because the screw 503 is non-rotatably coupled to the thrust plate 502, the screw 503 and the thrust plate 502 move together in a downward direction. Thus, the thrust plate 502 is lowered in a continuous fashion, and the staple pusher 514 and the knife 519, which are mounted to the bottom surface 5022 of the thrust plate 502, are also lowered in a continuous fashion.

As the staple pusher 514 is lowered, the downwardly-disposed teeth 5143 of the staple pusher 514 are pushed through the slots 5132 of the staple holder 513. The staples 528, which are initially disposed within the slots 5132 of the staple holder 513, are pushed downwardly and out of the lower openings of the slots 5132 and through the clamped tissue until the prongs 5281 of the staples 528 contact corresponding staple guides 5053 of the anvil 505. The staple guides 5053 bend and close the prongs 5281 of the staples 528, thereby stapling the tissue. Simultaneously, the knife 519 mounted to the bottom surface 5022 of the thrust plate 502 passes through the longitudinally-disposed slot 5131 of the staple holder 513 until it contacts the knife pad 520 of the anvil 505, thereby cutting the clamped tissue.

Having performed a stapling and cutting procedure, the second motor 676 is actuated to move the thrust plate 502 from the second lowered position to the first raised position. Specifically, the second motor 676 corresponding to the second drive shaft 632 is activated, which is engaged with the second drive socket 310. The rotation of the second drive shaft 632 causes the pinion 508*b* to rotate in a second, e.g., clockwise, direction. The gear teeth 5086 of the pinion 508*b* are engaged with the gear teeth 5292 of the spur gear 529*b*, such that this rotation of the pinion 508*b* causes the spur gear 529*b* to rotate in a second, e.g., counter-clockwise, direction. The internal bore 5294 of the spur gear 529*b* is engaged with the end 5234 of the second worm 523*b*, such that the rotation of the spur gear 529*b* causes the second worm 523*b* to rotate in a second, e.g., counter-clockwise, direction. The thread(s) 5236 of the worm 523*b* are engaged with the circumferentially-disposed worm gear teeth 5161 of worm gear 516, such that the rotation of the worm 523*b* causes the rotation of the worm gear 516 in a second, e.g., clockwise when viewed from the top, direction. The thread(s) of the internally-threaded bore 5164 of the worm gear 516 are engaged with the thread(s) of the screw 504, and, because the screw 504 is non-rotatably coupled to the thrust plate 502, screw 504 and thrust plate 502 are together moved in an upward direction. Simultaneously, the thread(s) 5236 of the worm 523*b* engage the worm gear teeth 5171 of the worm gear 517, such that the rotation of the worm 523*b* causes rotation of the worm gear 517 in a second, e.g., counter-clockwise when viewed from the top, direction. The thread(s) of the internally-threaded bore 5174 of the worm gear 517 is engaged with the threads of the screw 503, and, because the screw 503 is non-rotatably coupled to the thrust plate 502, the screw 503 and the thrust plate 502 move together in an upward direction. Thus, the thrust plate 502 is raised in a continuous fashion, and the staple pusher 514 and the knife 519, which are mounted to the bottom surface 5022 of the thrust plate 502, are also raised in a continuous fashion to their initial retracted positions.

Having performed the cutting and stapling of the tissue and having returned the knife 519 to its retracted position, the first motor 680 is actuated to place the surgical device in the open position. Specifically, the first motor 680 corresponding to the first drive shaft 630 is activated. The first drive shaft 630 is engaged with the first drive socket 180, such that the rotation of the first drive shaft 630 causes the pinion 508*a* to rotate in a first direction of rotation, e.g., counter-clockwise. The gear teeth 5083 of the pinion 508*a* are engaged with the gear teeth 5291 of the spur gear 529*a*, such that the rotation of the pinion 508*a* causes the spur gear to rotate in a first, e.g., clockwise, direction. The internal bore 5293 of the first spur gear 529*a* is engaged with the end 5231 of the first worm 523*a*, such that the rotation of the first spur gear 529*a* causes the first worm 523*a* to rotate in the same direction as the first spur gear 529*a*, e.g., clockwise. The thread(s) 5233 of the worm gear 523*a* are engaged with the worm gear teeth 5221 of the worm gear 522, such that the rotation of the worm gear 523*a* causes the rotation of the worm gear 522 in a first, e.g., counter-clockwise when viewed from the top, direction. The internal bore 5222 of the worm gear 522 is engaged with the portion 5212 of the head 5211 of the screw 521, such that the rotation of the worm gear 522 causes the screw 521 to rotate in a first, e.g., counter-clockwise when viewed from the top, direction. The externally-disposed thread(s) 5214 of the screw 521 are engaged with the thread(s) of the internally-threaded bore 5051 of the anvil 505, such that the rotation of the screw 521 causes anvil 505 to move in an downward direction, e.g., away from the frame housing 506. Thus, the second jaw 50 is separated from the first jaw 80, until the surgical device 11 is again in an open position, providing a space between the first jaw 80 and the second jaw 50, as illustrated in FIG. 3.

Thereafter, the surgical device 11 may be separated from the electro-mechanical driver component and replaced with another surgical device 11 so that the same clamping, cutting and stapling procedure may be performed on a different section of the tissue, e.g., on the opposite side of the anomalous or cancerous tissue. Once the second end of the bowel is also clamped, cut and stapled, the surgical device 11 may be separated from the electro-mechanical driver component 610. If necessary, an operator may discard the attachments or sterilize them for reuse.

It is noted that prior to actuation of the surgical device 11, a calibration procedure may be performed. Such a procedure is described in U.S. Provisional Patent Application No. 60/337,544, entitled "Calibration of a Surgical Instrument", filed on Dec. 4, 2001, which is expressly incorporated in its entirety herein by reference thereto.

According to the example embodiments of the present invention illustrated in FIGS. 8(*a*) and 8(*b*), the surgical device 11 may be non-reloadable, e.g., the staple holder 513 may not be removable from the housing 506 by an operator to reload the surgical device 11 with a subsequent array of staples 523 and reuse the surgical device 11 for the same, or other, patient or for the same, or other, procedure. Thus, after the surgical device 11 has been actuated once to staple a section of tissue using the staples 528 in the staple holder 513, the surgical device 11 cannot be actuated again to staple another section of tissue using a new set of staples 528 or a new staple holder 513. By configuring the surgical device 11 so as to be non-reloadable, the risk of contamination or infection is reduced, since the surgical device 11 may not be intentionally or unintentionally used on two different patients and may not be re-used on a single patient. However, in accordance with one example embodiment of the present invention, the surgical device 11 may be reloadable. For example, in this example embodiment, the surgical device 11 may be configured such that certain components are removable from the surgical device 11 and replaceable with respect to the surgical device 11. For example, in accordance with one example embodiment, the cartridge cap 515, the pin 518, the staple pusher 514 having the knife 519 mounted thereon, and the staple holder 513 having the staple retainer 540 attached thereto, form a replaceable cartridge that is detachably attached to the housing 506 and that may be removed from the housing 506 after being used in order to be replaced by another cartridge. The replaceable cartridge may be removable when the upper jaw 80 and the lower jaw 50 are in the fully open position to prevent the cartridge from being inadvertently removed when the upper jaw 80 and the lower jaw 50 are clamped onto a section of tissue to be cut and stapled. The example embodiments illustrated in FIGS. 8(*a*) and 8(*b*) include rails 5091 located on the anvil filler 509 that engage rail slots 5135 of the staple retainer 513 when the upper jaw 80 and the lower jaw 50 are not in the fully open position, but that disengage when the upper jaw 80 and the lower jaw 50 are in the fully open position, thereby enabling the staple retainer 513 and the other components of a replaceable cartridge to be slideably detached from the housing 506 for replacement. In an alternative example embodiment, the staple holder 513 is slideable into and out of the housing 506, such that a user may slide a new staple holder 513 having a new set of staples 528 into the housing 506 after the first set of staples 528 has been used. Alternatively, when the first set of staples 528 in the staple holder 513 has been used, the operator may replace the staples 528 in the same staple holder 513 and reuse the same staple holder 513. The pin 518 may be retractable out of the hole 5133 of the staple holder 513 and that the cartridge cap 515 may be removably or moveably connected to the housing 506.

In accordance with another example embodiment of the present invention, the surgical device 11 may provide limited reloadability. For example, the surgical device 11 may be configured to permit the staple holder 513 to be replaced once, so that the clamping, cutting and stapling operation may be performed twice on a single patient, e.g., on opposite sides of a cancerous section of tissue, but does not permit the staple holder 513 to be replaced more than twice.

In another example embodiment of the present invention, the surgical device 11 may be configured to maintain two sets of staples 528 within the staple holder 513, a first set of which is used on one side of a cancerous section of tissue and a second set of which is used on the other side of the cancerous section of tissue. It should be understood that the surgical device 11 may be configured for any number of uses and that usage may be determined in accordance with the usage data 1184. That is, the memory module 501 may be configured to store data representing the number of times that the surgical device 11 is reloaded. Thus, in accordance with the operating program, the electro-mechanical driver component 610 may limit the number of times that a reloaded surgical device 11 may be fired in accordance with the usage information stored in the memory module 501.

A surgical device 11 that is configured to be reloadable may be operated in a similar manner to the non-reloadable surgical device 11 described above. However, the reloadability of the surgical device 11 permits the operator to perform additional steps during the operation of the surgical device 11. For example, once the surgical device 11 is initially placed in the open position, the staple holder 513 may be accessed by the operator and may be inspected to determine whether the staples 528 are ready for the procedure and/or whether the need exists to replace the staple holder 513 with a more suitable staple holder 513. Similarly, once a clamping, cutting and stapling operation has been performed and the set of staples 518 has been used, the staple holder 513 may be accessed by the operator again in order to replace the staple holder 513 with another staple holder 513 or to insert another set of staples 518 into the same staple holder 513.

According to the example embodiments of the present invention illustrated in FIGS. 8(*a*) and 8(*b*), the surgical device 11 may be configured to operate in more than one range of operation. This feature may provide the advantage that sections of tissue having different thicknesses may be more appropriately accommodated by the surgical device 11. For example, according to one example embodiment of the invention, the surgical device 11 may be configured to vary the distance between the upper jaw 80 and the lower jaw 50 when the surgical device 11 is in the closed position, or to vary the position of the thrust plate 535 relative to the upper jaw 80 when the thrust plate 535 is in the fully extended position. According to one example embodiment, the surgical device 11 may be reloadable so as to use two or more different sizes of staple holder 513, e.g., staple holders 513 that have different thicknesses or that house staples 518 having different lengths. In this example embodiment, an operator may select to employ one of two or more different staple holders 513 having different size staples 528 disposed therein. The staple holder 513 may include a memory module readable by the controller 1122 in order that the controller 1122 may recognize the staple holder 513 as including staples configured to staple the corresponding thickness of tissue. The controller 1122 may then control the first drive shaft 630 during operation so that the distance between the upper jaw 80 and the lower jaw 50 when the surgical device 11 is moved into the closed position corresponds to the thickness of the tissue to be cut and stapled by the staples 523. Similarly, the controller 1122 may control the second drive shaft 632 so that the position of the thrust plate 535, the staple pusher 514 and the knife 519 when moved into the extended position corresponds to the thickness of the tissue to be cut and stapled by the staples 523.

In accordance with another example embodiment of the invention, different sizes of a non-reloadable surgical device 11 may be used, each size of the non-reloadable surgical device 11 corresponding to a different thickness of tissue to be cut and stapled. In this example embodiment, the memory module 501 of the surgical device 11 may include data readable by the controller 1122 to identify to the controller 1122 that the surgical device 11 corresponds to a particular thickness of tissue to be cut and stapled.

In still another example embodiment of the invention, the controller 1122 is configured to provide more than one range of operation for the same set of staples 523. For example, the controller 1122 may be configured to enable an operator to select settings that correspond to different thicknesses of tissue to be cut or stapled. For example, according to one example embodiment, the controller 1122 is configured to actuate the first drive shaft 630 to close the upper jaw 80 to a first position relative to the lower jaw 50 in order to clamp a section of tissue disposed therebetween. The operator may then select whether to actuate the second drive shaft 632 in order to cut and staple the tissue or whether to actuate the first drive shaft 630 again in order to close the upper jaw 80 to a second position relative to the lower jaw 50. This example embodiment may provide the advantage that an operator is not required to pre-select a particular size of the surgical device 11 or to pre-select a replaceable cartridge for the surgical device 11 before the section of tissue to be cut and stapled has been exposed and its thickness is determined. This arrangement may prevent an operator from pre-selecting a wrong size or from maintaining an inventory of more than one size available for use.

The surgical device 11 may also be configured to be automatically calibrated upon attachment to the electro-mechanical driver component 610. For example, the controller 1122 may be configured to open or close the surgical device 11 in order to determine the fully-open or fully-closed position of the surgical device 11 before operation. According to one example embodiment, the surgical device 11 and the electro-mechanical driver component 610 are configured to perform the automatic calibration routine independent of the presence of, or of the thickness of, the staple retainer 540 by employing a mechanical hard-stop calibration feature. As mentioned above, an example of a calibration procedure for use with surgical devices is described in U.S. Provisional Patent Application No. 60/337,544, which is expressly incorporated herein in its entirety by reference thereto.

Figure 20A:
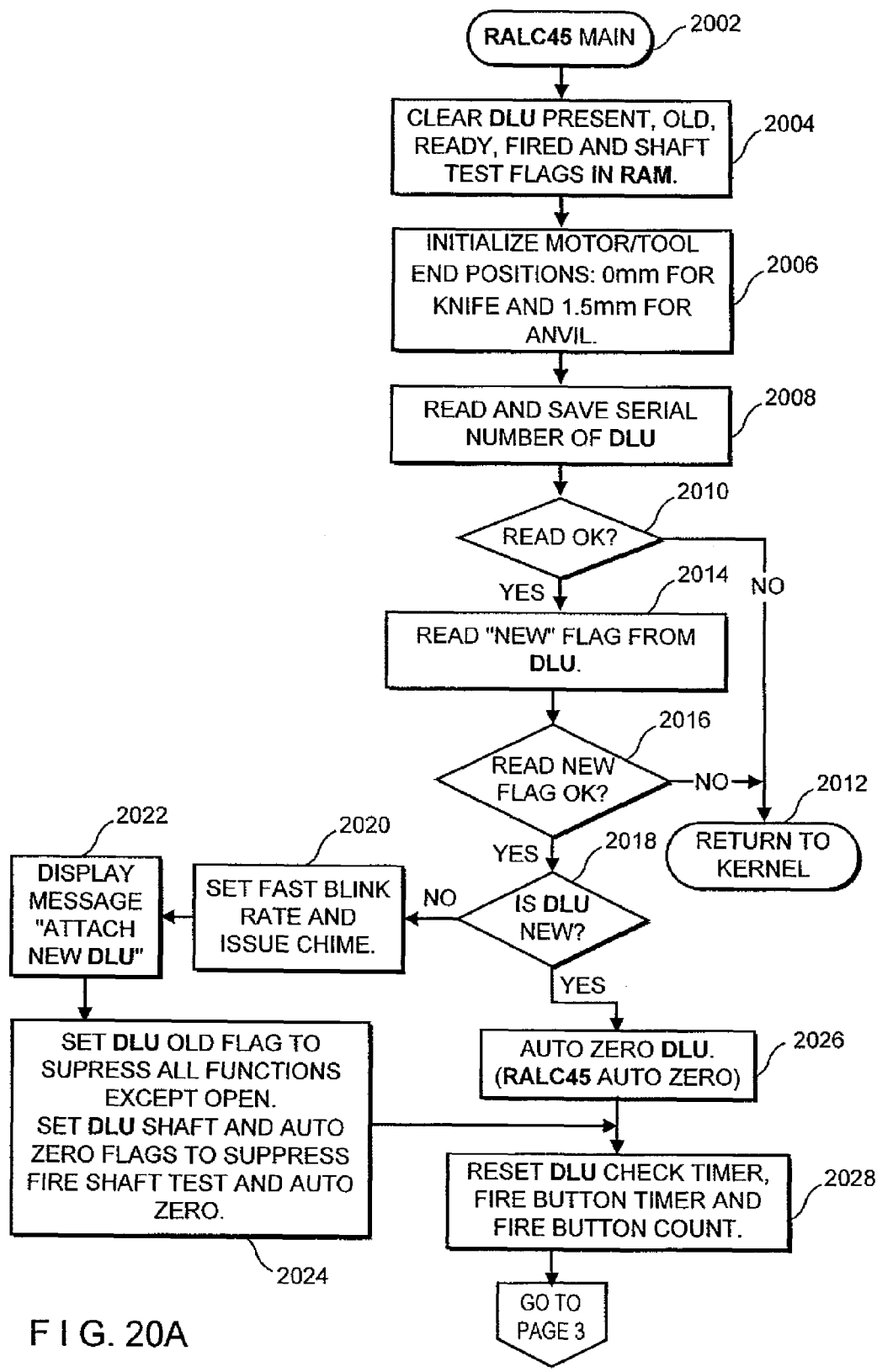
FIGS. 20(a) to 20(c) illustrate a flowchart of a main operating program, the steps of which are performed during the operation of the surgical device in accordance with one example embodiment of the present invention.

FIGS. 20(*a*) to 20(*c*) illustrate a flowchart for a main operating program according to one example embodiment of the present invention for operating the surgical device 11. According to one example embodiment of the invention, the main operating program is executed by the controller 1122, although it should be understood that other or additional controllers, electronic devices, etc. may be configured to execute some or all of the steps illustrated in the flowcharts. Referring to FIG. 20(*a*), in step 2002, the main operating program is initialized. This step 2002 may include, for example, the steps of obtaining the operating program from memory unit 1130 or from the memory module 501 of the surgical device 11, as described above. In step 2004, a DLU PRESENT flag, a DLU OLD flag, a DLU READY flag, a DLU FIRED flag and a SHAFT TEST flag are cleared in respective memory locations in the RAM 1134. The term "DLU" refers to the surgical device 11 or other instrument or attachment attached to the electro-mechanical driver component 610. In step 2006, the end positions of the motor/tool, e.g., motors 676 and 680 that drive the surgical device 11, are initialized. In accordance with one example embodiment of the present invention, the end position of the knife 519 is initialized at 0 mm, while the end position of the anvil 505 is initialized at 1.5 mm. In step 2008, the serial number of the surgical device 11, e.g., ID data 1182 that is stored in the memory module 501 of the surgical device 11, is read from the memory module 501 and saved. According to an example embodiment of the present invention, upon failure to read and save the serial number of the surgical device 11, step 2008 may be repeated a predetermined number of times within a predetermined time period or at predetermined time intervals. The predetermined number of times may be, for example, three, and the predetermined time period may be, for example, 100 mS. Failure to read and save the serial number of the surgical device, either initially or after a predetermined number of tries, may be determined as an error condition, in which case operation ends as described below.

In step 2010, it is determined whether the ID data 1182 was successfully read and/or whether the ID data 1182 is valid. If it is determined in step 2010 the ID data 1182 was successfully read and/or that the ID data 1182 is valid, then in step 2012, control returns to the kernel, e.g., the basic operating program of the electro-mechanical driver component 610. If, in step 2010, it is determined that the ID data 1182 has been successfully read in step 2008 and/or that the read ID data 1182 is valid, then in step 2014, the DLU NEW flag of the RAM 1134 is read. In step 2016, it is determined whether the DLU NEW flag has been successfully read and/or whether the DLU NEW flag is valid. If it is determined in step 2016 that the DLU NEW flag was not successfully read and/or is not valid, then control proceeds to step 2012, at which control returns to the kernel. If it is determined in step 2010 that the DLU NEW flag has been successfully read and/or that the DLU NEW flag is valid, then control proceeds to step 2018.

In step 2018, it is determined whether the surgical device 11 is new based on the DLU NEW flag. If it is determined in step 2018 that the surgical device 11 is new, then control proceeds to step 2026. In step 2026, an auto-zero operation is performed with respect to the surgical device 11, and control proceeds to step 2028. The auto-zero operation of step 2026 is explained in more detail in connection with the flowchart illustrated in FIGS. 22(a) to 22(c). If it is determined in step 2018 that the surgical device 11 is not new, then control proceeds to step 2020, in which the display device 616 of the electro-mechanical driver component 610 indicates that the surgical device 11 was determined in step 2018 to not be new. For example, in step 2020, the display device 616 may blink at a fast rate and/or to issue an audible chime. In step 2022, a message, such as "ATTACH NEW DLU" is displayed on display device 616. In step 2024, the DLU OLD flag of the memory device, e.g., RAM 1134, is set to thereby suppress all functions except an open function. In addition, the DLU SHAFT and the AUTO-ZERO flags of the memory device, e.g., RAM 1134, are set to suppress a fire shaft test function and an auto-zero function. In step 2028, a DLU CHECK timer, a FIRE BUTTON timer and a FIRE BUTTON counter are reset.

Figure 20B:
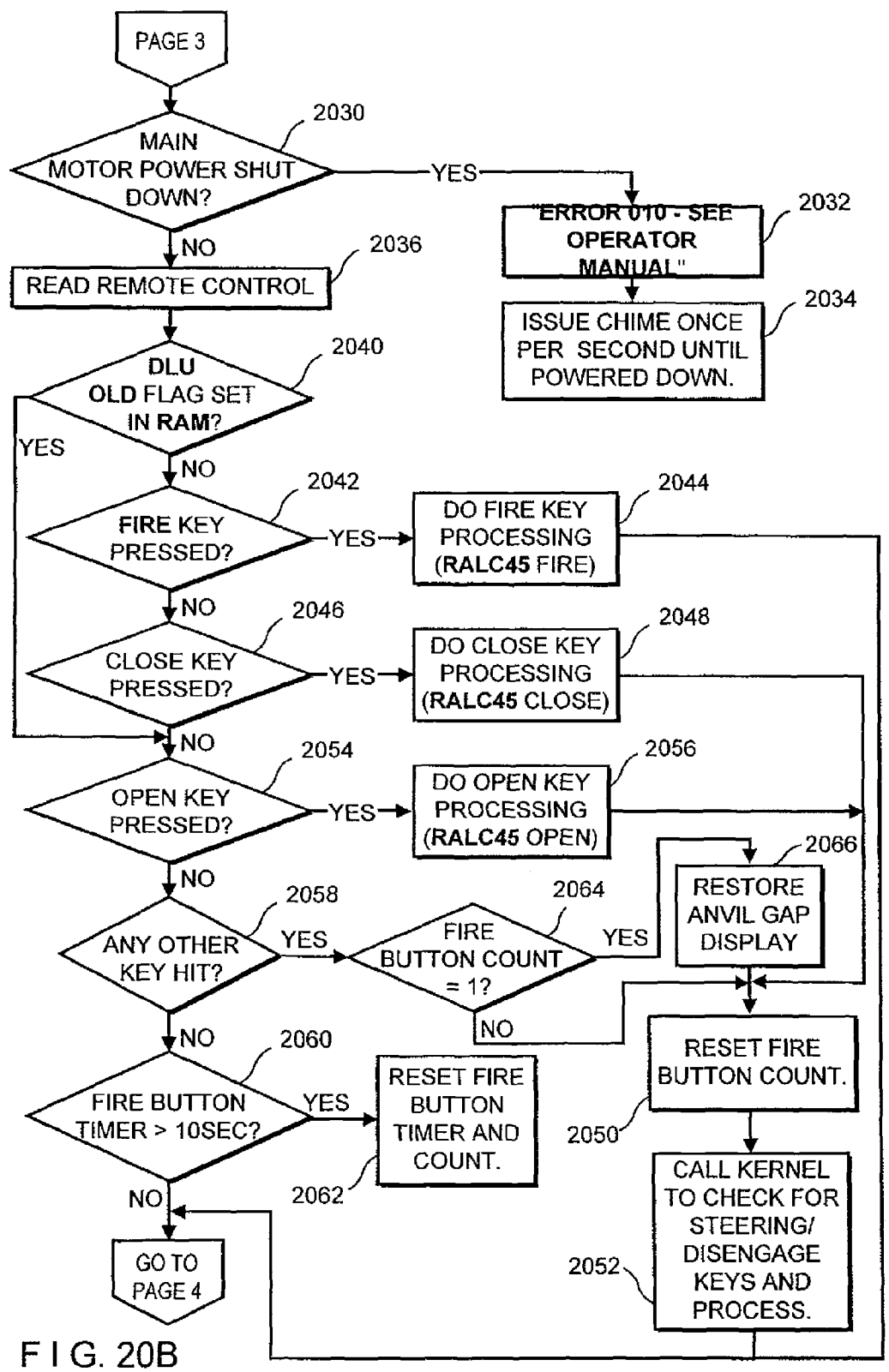
Figure 24A:
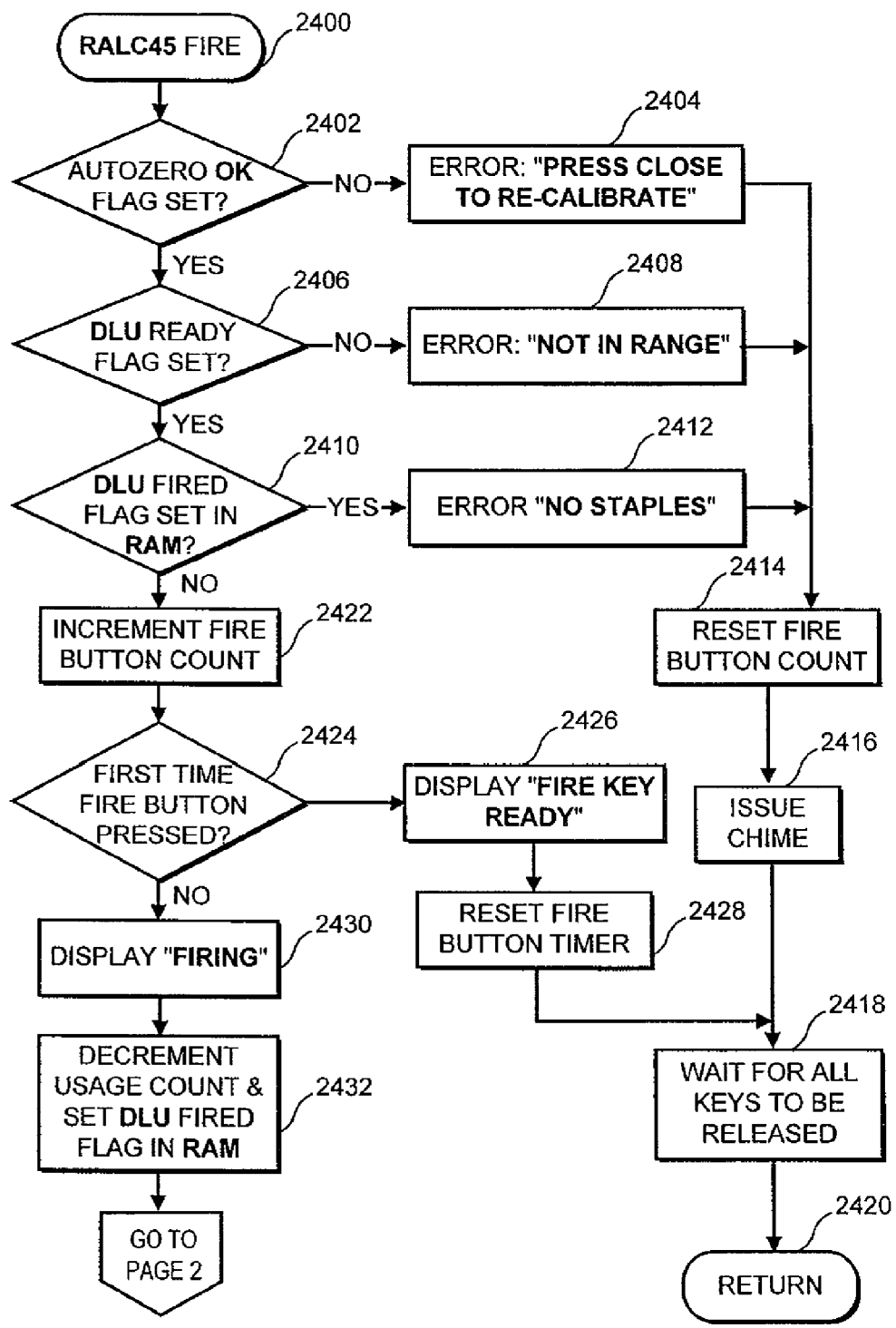
FIGS. 24(a) to 24(c) illustrate a flowchart of a clamping, cutting and stapling routine of the main operating program illustrated in FIGS. 20(a) to 20(c) in accordance with one example embodiment of the present invention.
Figure 24B:
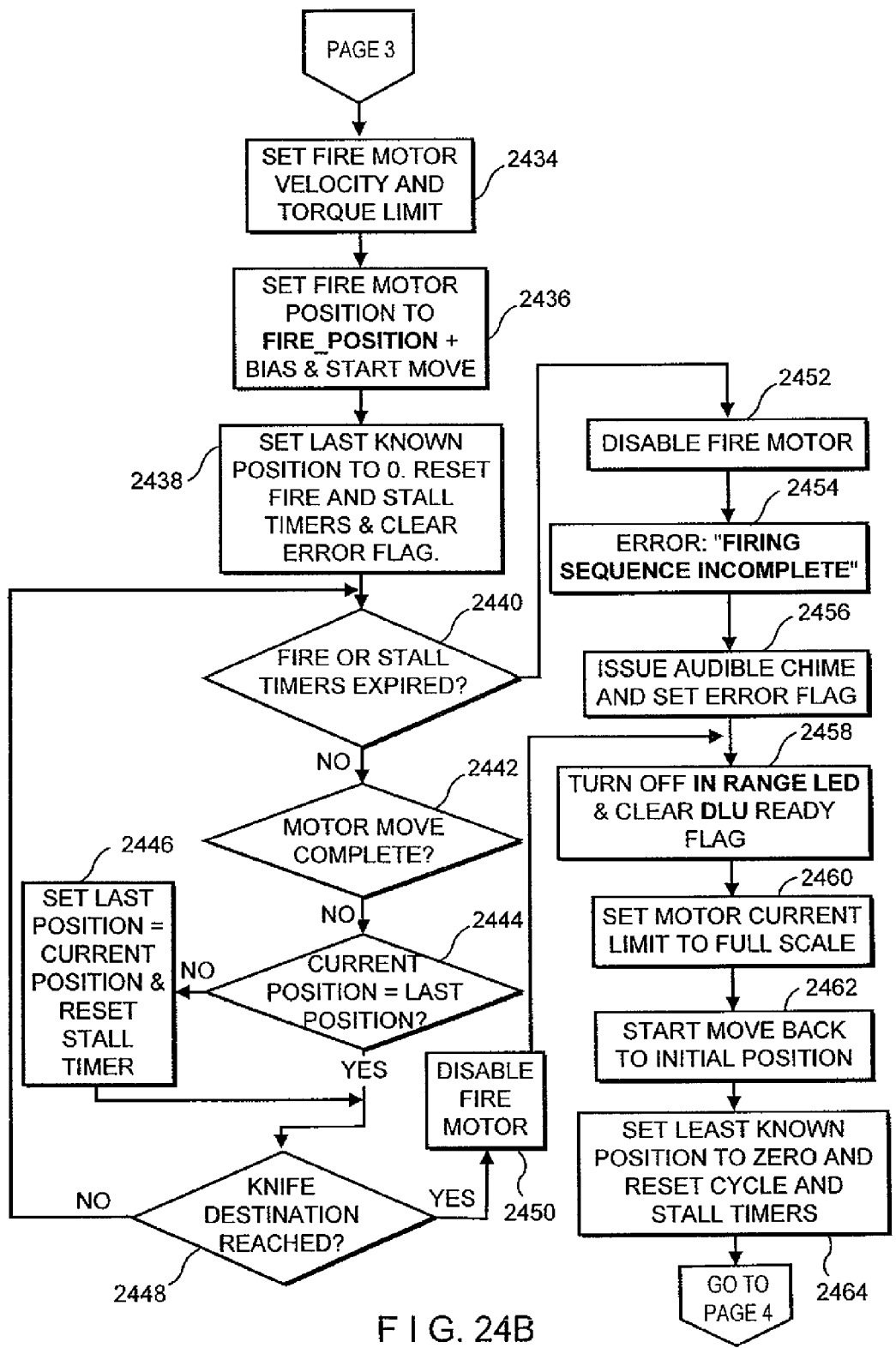
Figure 24C:
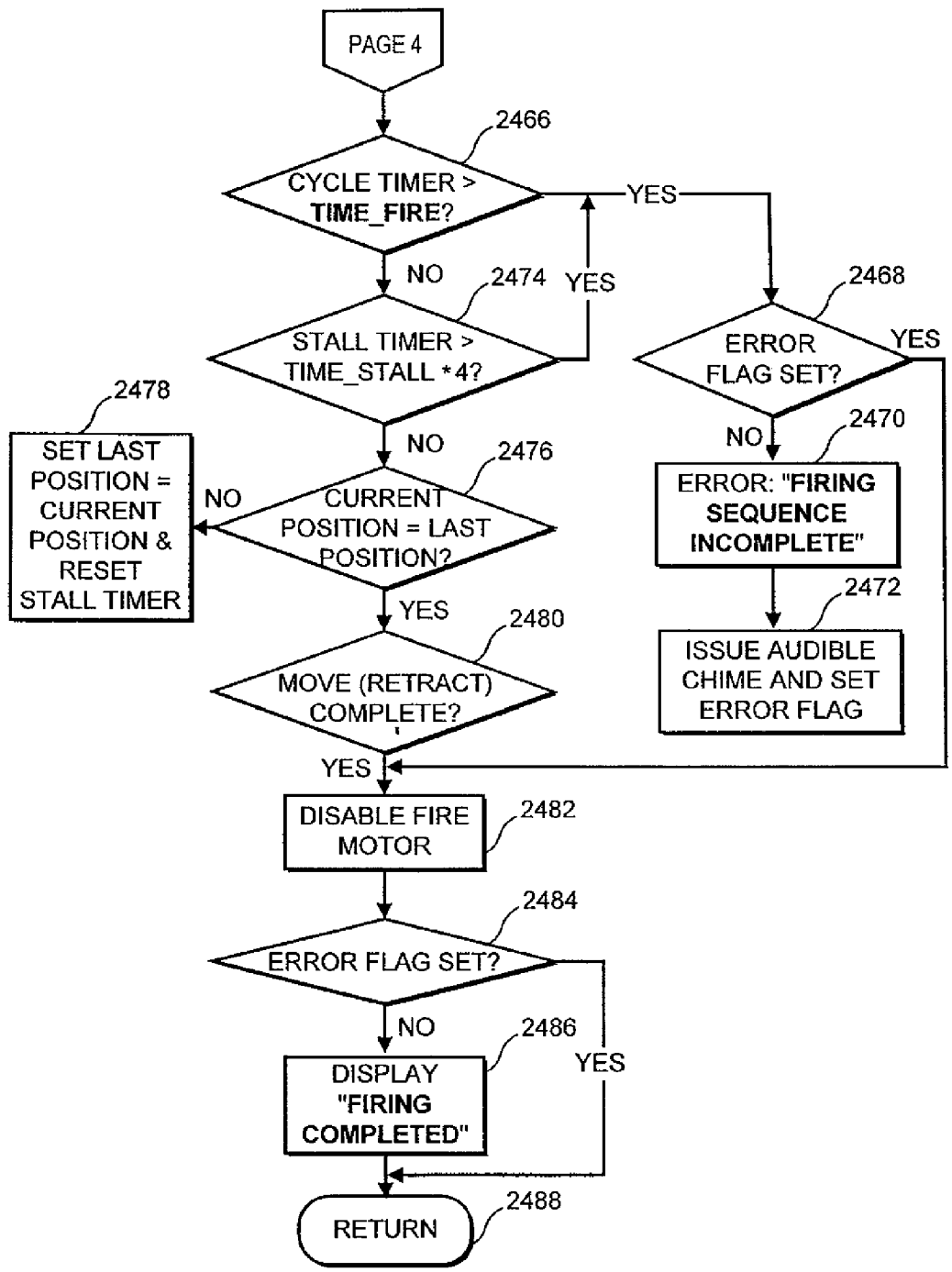

After step 2028 is performed, control proceeds to the steps illustrated in the flowchart of FIG. 20(b). In step 2030, it is determined whether the main motor power of the electro-mechanical driver component 610 has been shut down. If it is determined in step 2030 that the main motor power has been shut down, control proceeds to step 2032, in which a message, such as "ERROR 010—SEE OPERATOR MANUAL" is displayed, e.g., on display device 616. In step 2034, an indication is provided, e.g., a chime is issued repeatedly, e.g., once per second, until the electro-mechanical driver component 610 is shut down. If it is determined in step 2030 that the main motor power has not been shut down, the remote control device is read in step 2036. In step 2040, it is determined whether the DLU OLD flag is set, e.g., in RAM 1134. If the DLU OLD flag is set, then control proceeds to step 2054. If it is determined in step 2040 that the DLU OLD flag is not set, then control proceeds to step 2042, in which it is determined whether a FIRE key, e.g., the switch 1320 of the wireless RCU 1148 or the switch 1320' of the wired RCU 1150, is pressed. If it is determined in step 2042 that the FIRE key is pressed, then control proceeds to step 2044, in which a firing operation is performed. The firing operation is described below and illustrated in FIGS. 24(a) to 24(c). If it is determined in step 2042 that the FIRE key is not pressed, then control proceeds to step 2046.

Figure 21A:
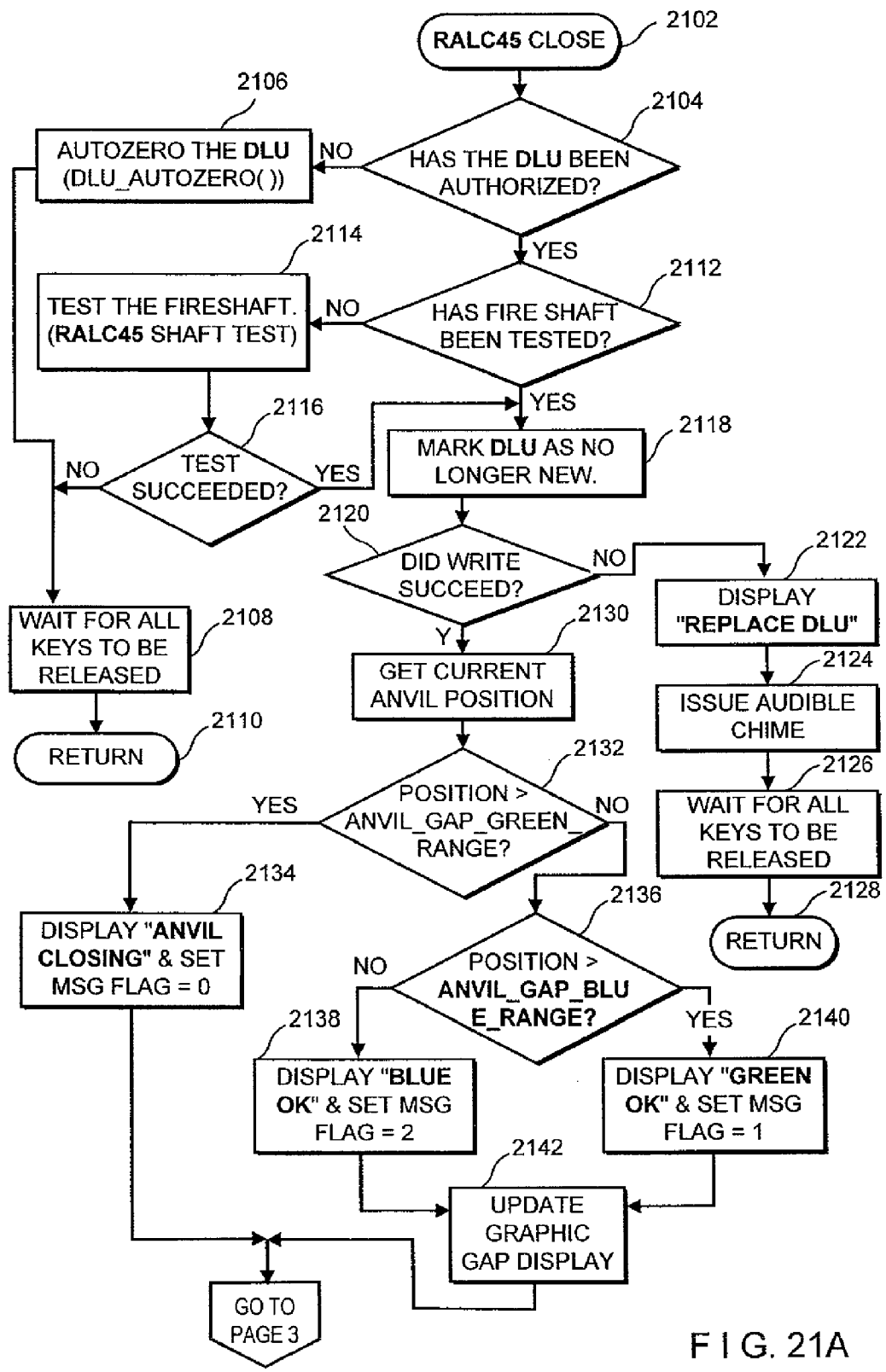
Figure 23:
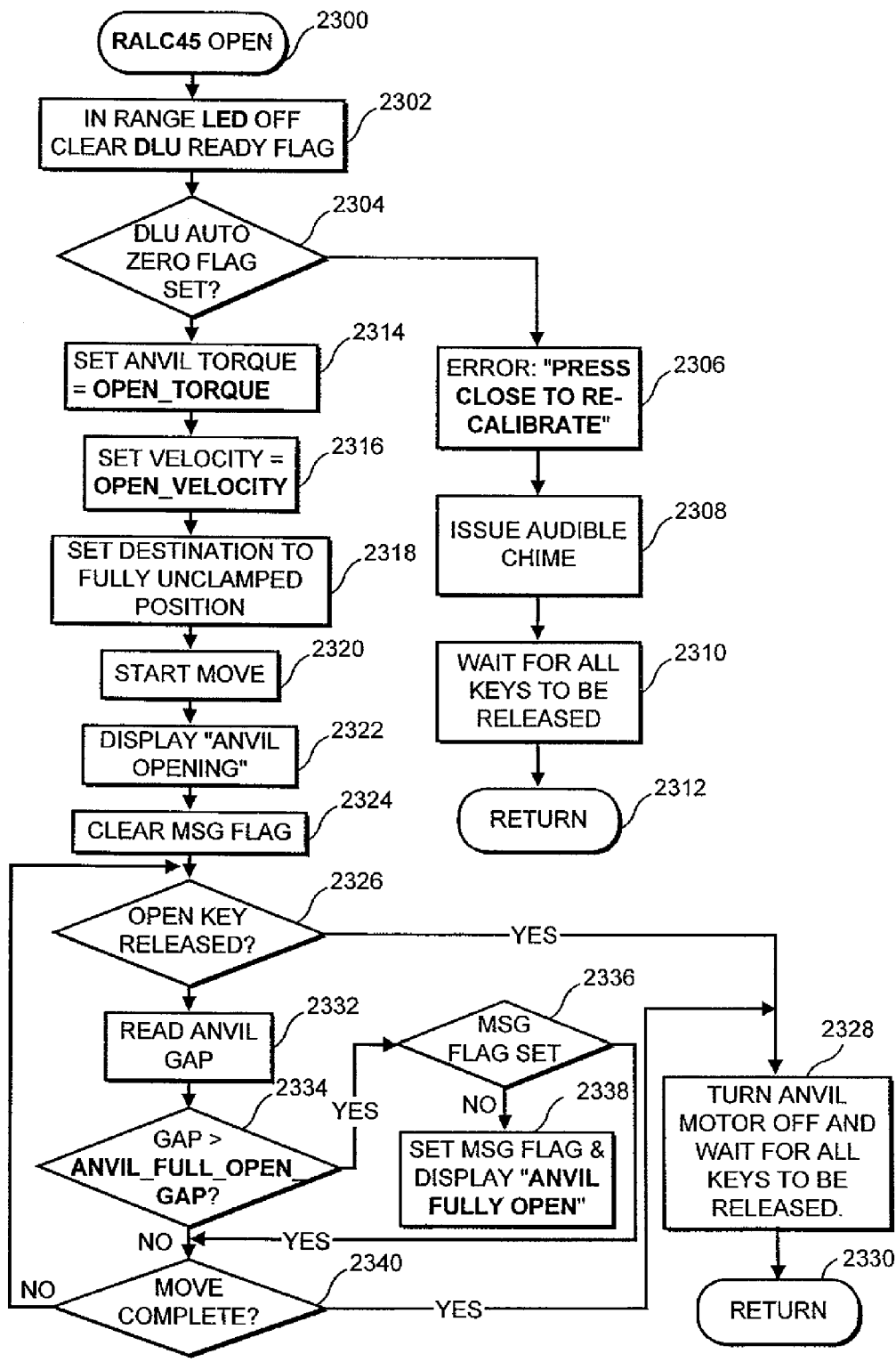
FIG. 23 illustrates a flowchart of a jaw opening routine of the main operating program illustrated in FIGS. 20(a) to 20(c) in accordance with one example embodiment of the present invention.

In step 2046, it is determined whether a CLOSE key, e.g., the switch 1320 of the wireless RCU 1148 or the switch 1320' of the wired RCU 1150, is pressed. If it is determined in step 2046 that the CLOSE key is pressed, then control proceeds to step 2048, in which a closing operation is performed as illustrated in FIGS. 21(a) to 21(c). If it is determined in step 2046 that the CLOSE key is not pressed, then control proceeds to step 2054, in which it is determined whether an OPEN key, e.g., the switch 1320 of the wireless RCU 1148 or the switch 1320' of the wired RCU 1150, is pressed. If it is determined in step 2054 that the OPEN key is pressed, then control proceeds to step 2056, in which an opening operation is performed as illustrated in FIG. 23. If it is determined in step 2054 that the OPEN key is not pressed, then control proceeds to step 2058.

In step 2058, it is determined whether any other key, e.g., of the wireless RCU 1148 or the wired RCU 1150, is pressed. If it is determined in step 2058 that another key is pressed, then control proceeds to step 2064. If it is determined in step 2058 that no other key is pressed, then control proceeds to step 2060. In step 2060, it is determined whether a fire button timer exceeds a predetermined period of time, e.g., ten seconds. If it is determined in step 2060 that the fire button timer does exceed the predetermined period of time, the fire button timer and count are reset in step 2062. Control then proceeds to step 2064 in which it is determined whether the fire button count has a value of "1". If it is determined in step 2064 that the fire button count has a value of "1", control proceeds to step 2066, in which the display of an anvil gap on display device 616 is restored. After step 2066 is performed, control proceeds to step 2050, in which the fire button count is reset. Thereafter, in step 2052, the kernel is called in order to check for steering or disengagement keys and to process the same.

Figure 20C:
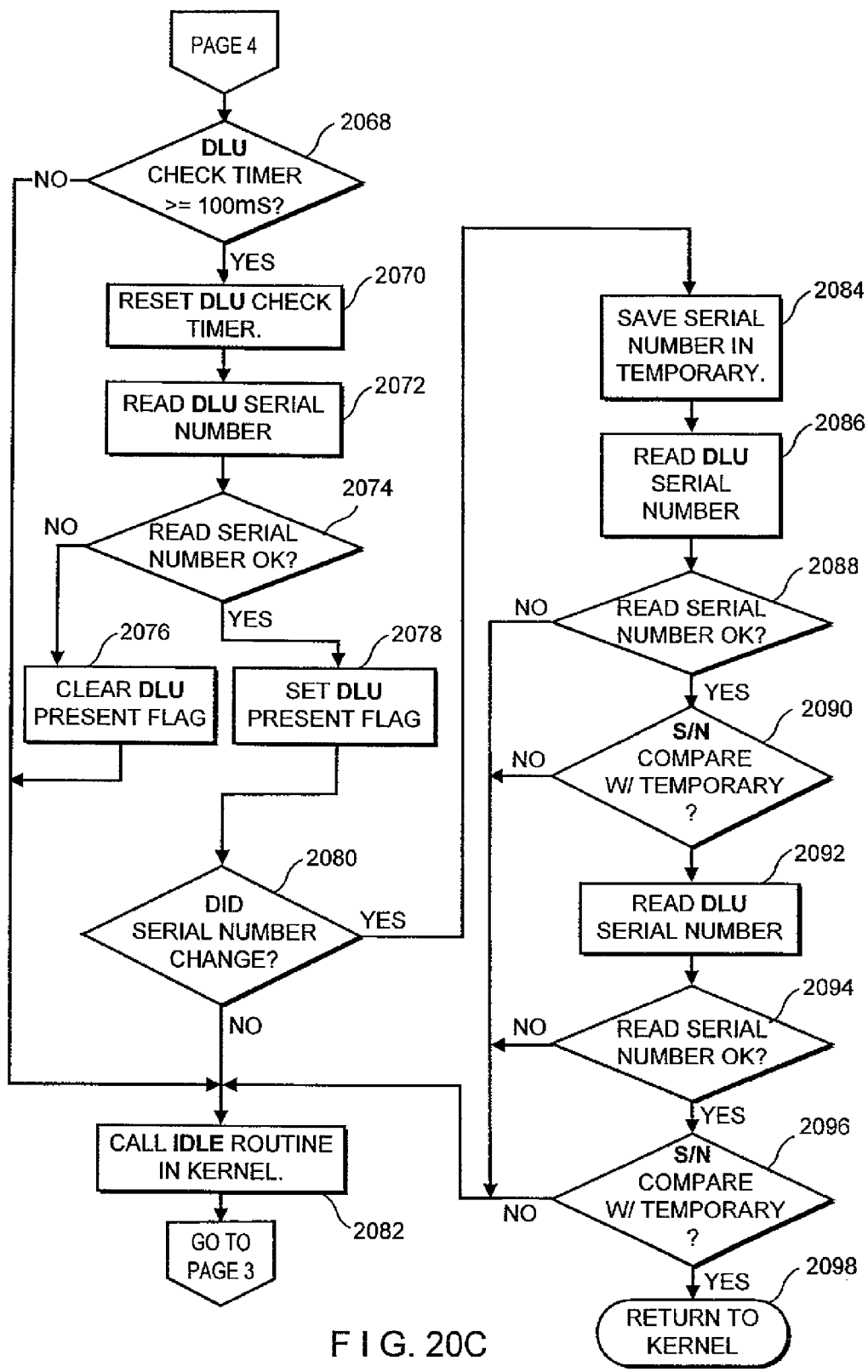

After step 2044, step 2052 or step 2060 is performed, control proceeds to the steps illustrated in FIG. 20(c). In step 2068, it is determined whether the DLU check timer has a value that is greater than or equal to a predetermined value, e.g., 100 mS. If it is determined in step 2068 that the DLU check timer does not have a value that is greater than or equal to a predetermined value, control proceeds to step 2082. If it is determined in step 2068 that the DLU check timer does have a value that is greater than or equal to the predetermined value, then, in step 2070, the DLU check timer is reset. In step 2072, the DLU serial number is read. In step 2074, it is determined whether the DLU serial number was able to be read. If it is determined in step 2074 that the DLU serial number was not able to be read, the DLU present flag in the RAM 1134 is cleared. If it is determined in step 2074 that the DLU serial number is able to be read, then, in step 2078, the DLU present flag is set.

In step 2080, it is determined whether the serial number of the surgical device 11 has changed. If it is determined in step 2080 that the serial number has not changed, control proceeds to step 2082, at which an IDLE routine is called. Thereafter, control returns to step 2030. If it is determined in step 2080 that the serial number has changed, then, in step 2084, the serial number is stored in a temporary memory location. In step 2086, the serial number of the surgical device 11 is read. In step 2088, it is determined whether the DLU serial number was able to be read. If it is determined in step 2088 that the DLU serial number was not able to be read, control proceeds to step 2082, at which the IDLE routine is called. If it is determined in step 2088 that the DLU serial number is able to be read, then, in step 2090, a comparison step is performed with respect to the DLU serial number and the serial number stored in the temporary storage location. If it is determined in step 2090 that the comparison between the DLU serial number and the serial number stored in the temporary storage location is not successful, then control proceeds to step 2082, in which the IDLE routine is called. If it is determined in step 2090 that the comparison between the DLU serial number and the serial number stored in the temporary storage location is successful, then, in step 2092, the serial number of the surgical device 11 is read. In step 2094, it is determined whether the DLU serial number was able to be read. If it is determined in step 2094 that the DLU serial number was not able to be read, control proceeds to step 2082, in which the IDLE routine is called. If it is determined in step 2094 that the DLU serial number is able to be read, then, in step 2096, a comparison step is performed with respect to the DLU serial number and the serial number stored in the temporary storage location. If it is determined in step 2096 that the comparison between the DLU serial number and the serial number stored in the temporary storage location is not successful, control proceeds to step 2082, at which the IDLE routine is called. If it is determined in step 2096 that the comparison between the DLU serial number and the serial number stored in the temporary storage location is successful, then, in step 2098, control returns to the kernel.

FIGS. 21(a) to 21(c) illustrate an example of a jaw-closing routine for closing the jaws of the surgical device 11 when attached to the electro-mechanical driver component 610. According to one example embodiment of the present invention, the closing routine may be executed by the controller 1122, although, as described above, it should be understood that other controllers, electronic devices, etc. may be configured to execute some or all of the steps illustrated in FIGS. 21(a) to 21(c).

Figure 22A:
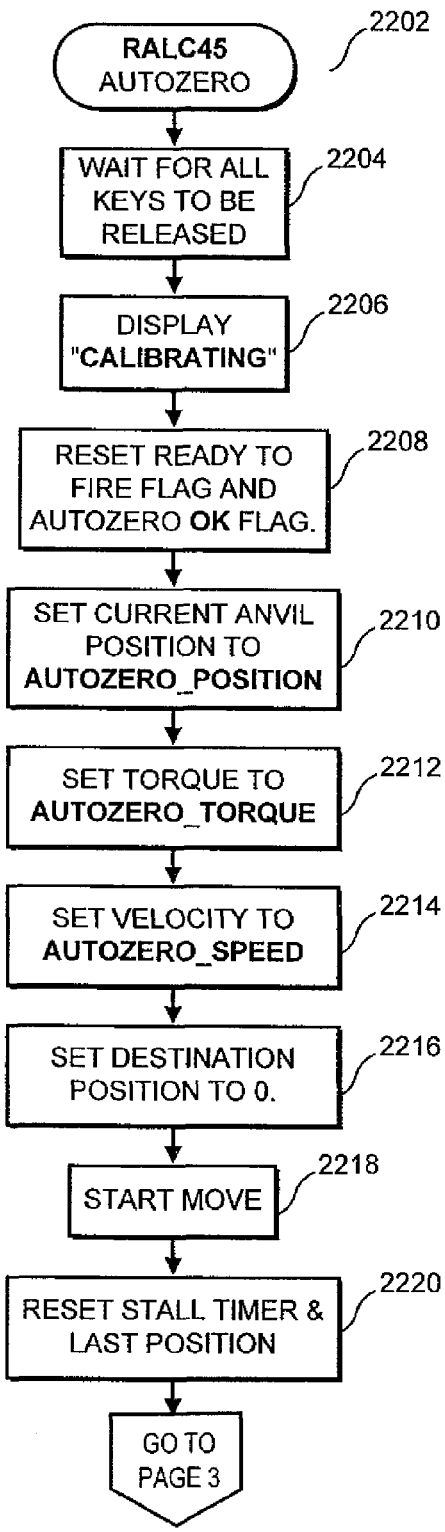
FIGS. 22(a) to 22(c) illustrate a flowchart of a calibration routine of the main operating program illustrated in FIGS. 20(a) to 20(c) in accordance with one example embodiment of the present invention.
Figure 22B:
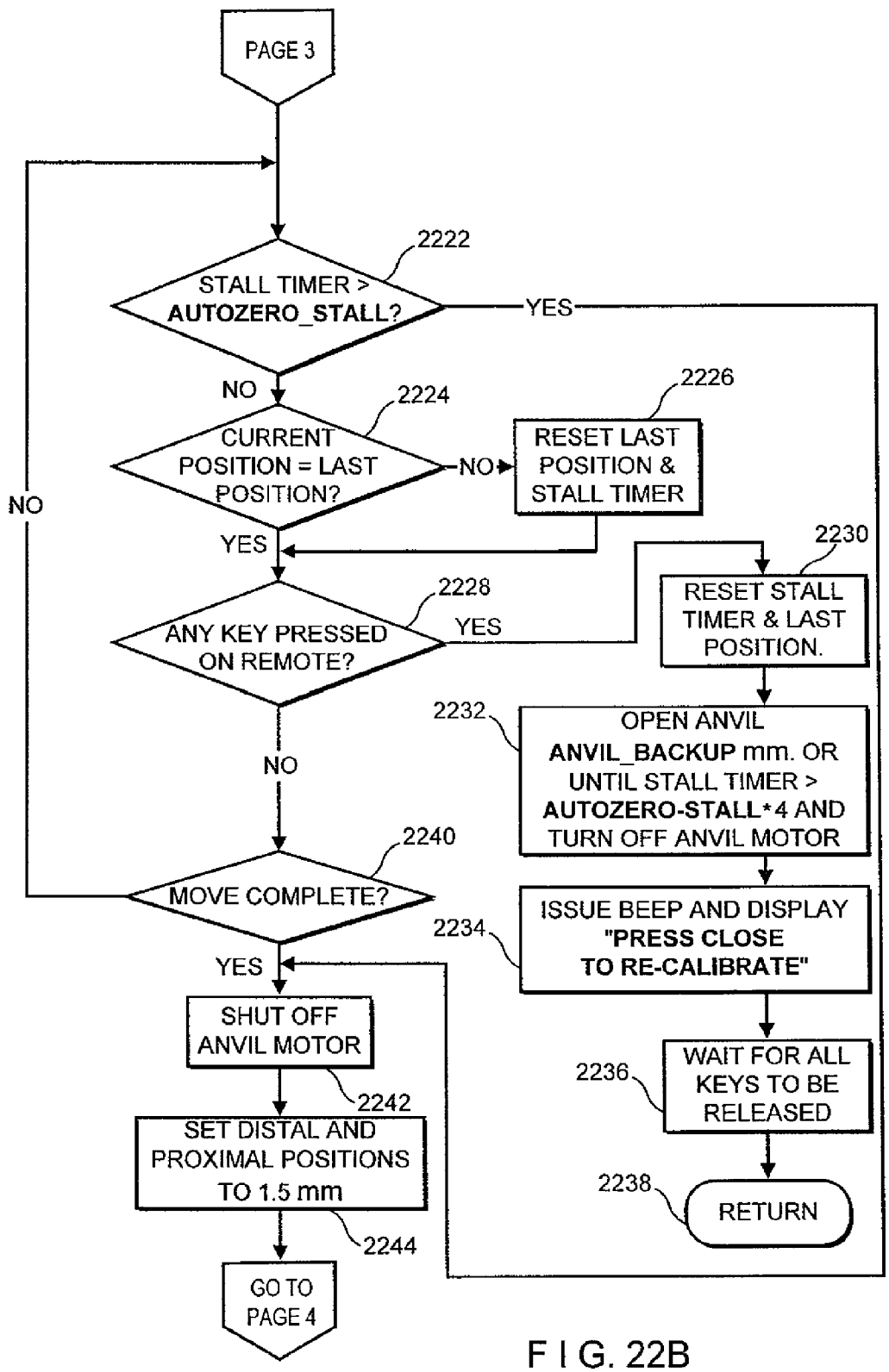
Figure 22C:
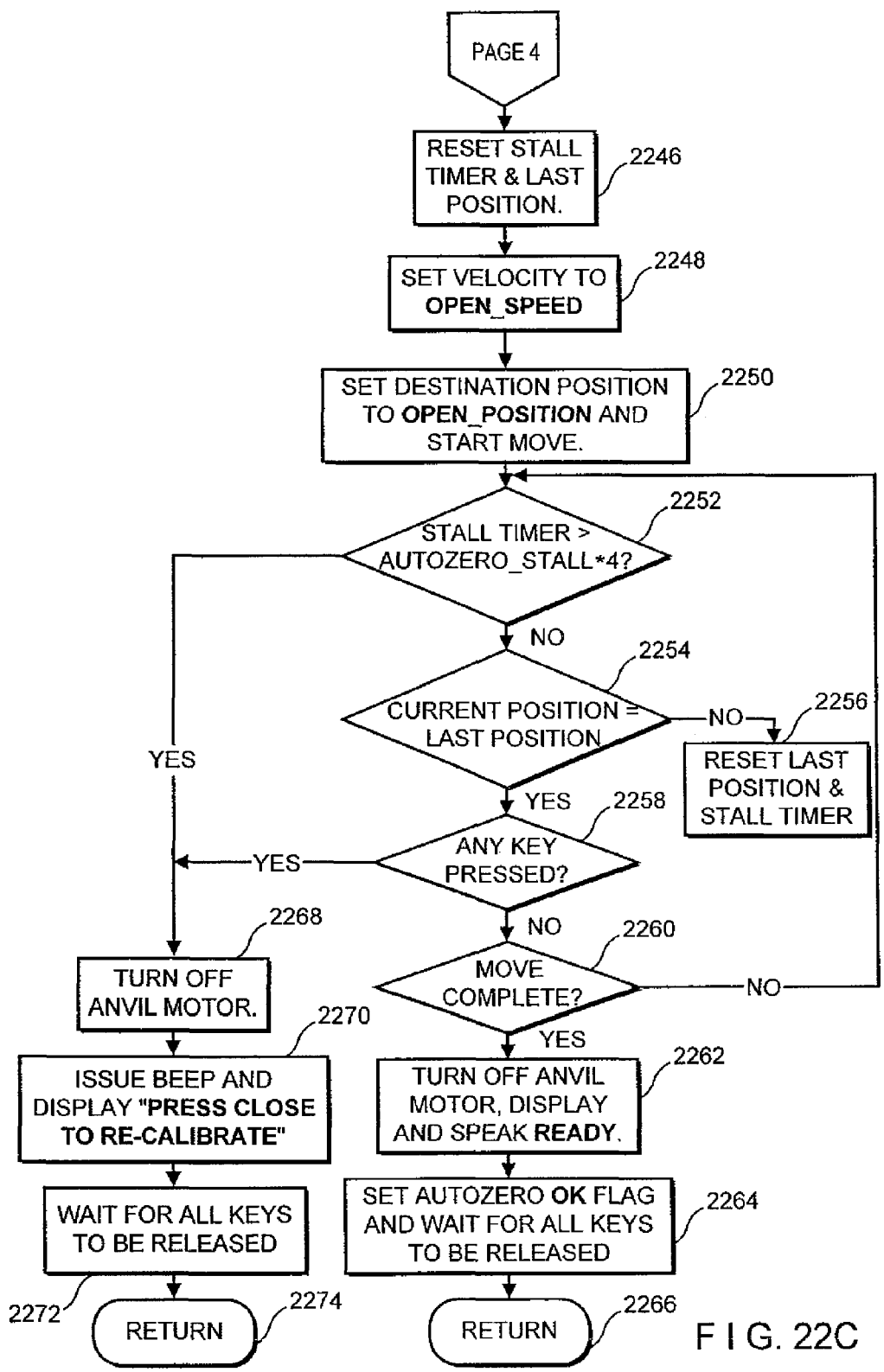
Figure 25A:
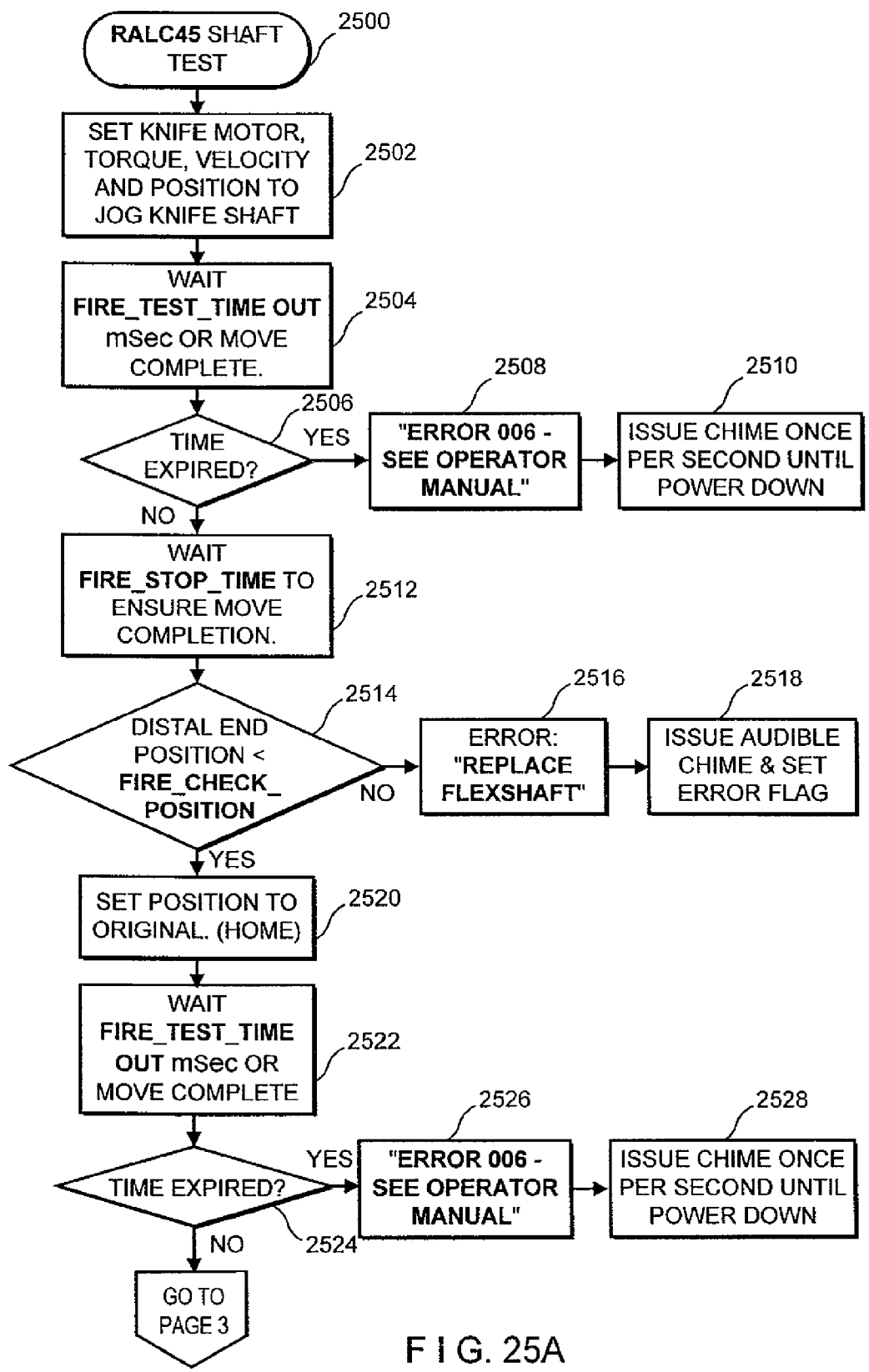

Referring to FIG. 21(a), in step 2102, the jaw-closing routine is initialized. In step 2104, it is determined whether the surgical device 11 has been auto-zeroed, e.g., has performed or has had performed thereon, an auto-zero operation. If it is determined in step 2104 that the surgical device 11 has not been auto-zeroed, then in step 2016 an auto-zero operation is performed. One example of an auto-zero operation is illustrated in the flowchart of FIGS. 22(a) to 22(c). Then, in step 2108, the release of all keys of the remote device, e.g., the wireless RCU 1148 or the wired RCU 1150, is awaited. In step 2110, control returns to the main operating program of FIGS. 20(a) to 20(c). If it is determined in step 2104, that the surgical device 11 has been auto-zeroed, then control proceeds to step 2112, at which it is determined whether the flexible shaft 620 has been tested. If in step 2112 it is determined that the flexible shaft 620 has not been tested, then in step 2114, a shaft test routine is performed. An example of a shaft test routine is illustrated in FIGS. 25(a) and 25(b). If in step 2116 it is determined that the shaft test performed in step 2114 did not succeed, then control proceeds to step 2108. As described above, in step 2108, the release of all keys of the remote device is awaited and in step 2110, control returns to the main operating program.

If it is determined in step 2112 that the flexible shaft 620 has not been tested, or if it is determined in step 2116 that the shaft test did not succeed, then control proceeds to step 2118, in which the surgical device 11 is marked as no longer being new. For example, the memory module 501 may be written to in step 2118 to indicate that the surgical device 11 is no longer new. In step 2120, it is determined whether the marking step 2118 was successful. If it is determined in step 2120 that the marking step 2118 was not successful, then control proceeds to step 2122, in which a message, such as "REPLACE DLU" is displayed, e.g., on display device 616. In step 2124, an audible chime is issued. In step 2126, the release of all keys of the remote device 1148 or 1150 is awaited. Control then returns in step 2128 to the main operating program illustrated in FIGS. 20(a) to 20(c).

If it is determined in step 2120 that the marking step performed in step 2118 was successful, then control proceeds to step 2130. In step 2130, a value corresponding to the current position of the anvil 505 is obtained. In step 2132, it is determined whether the value corresponding to the current position of anvil 505 is greater than a value referred to as ANVIL_GAP_GREEN_RANGE. The value of ANVIL_GAP_GREEN_RANGE may be stored, for example, in a memory location of memory unit 1130. If it is determined in step 2132 that the value corresponding to the current position of anvil 505 is greater than the value referred to as ANVIL_GAP_GREEN_RANGE, then in step 2134, a message, such as "ANVIL CLOSING" is displayed, e.g., on display device 616, and a msg flag is set to a value of "0". If it is determined in step 2132 that the value corresponding to the current position of anvil 505 is not greater than the value referred to as ANVIL_GAP_GREEN_RANGE, then, in step 2136, it is determined whether the value corresponding to the current position of anvil 505 is greater than a value referred to as ANVIL_GAP_BLUE_RANGE. If it is determined in step 2136 that the value corresponding to the current position of anvil 505 is greater than a value referred to as ANVIL_GAP_BLUE_RANGE, then, in step 2140, a message, such as "GREEN OK" is displayed, e.g., on display device 616 and a msg flag is set to a value of "1". If it is determined in step 2136 that the value corresponding to the current position of anvil 505 is not greater than a value referred to as ANVIL_GAP_BLUE_RANGE, then, in step 2138, a message, such as "BLUE OK" is displayed, e.g., on display device 616, and a msg flag is set to a value of "2". Thus, the message displayed on the display device 616 provides an indication to a user whether the gap between the first jaw 80 and the second jaw 50 is within, e.g., a "green" range for sections of tissue that are within a first predetermined thickness range, and a "blue" range for sections of tissue that are within a second predetermined thickness range. In accordance with one example embodiment of the present invention, the "green" range corresponds to sections of tissue that are within a thickness range between approximately 1.5 mm and 2.0 mm, and the "blue" range corresponds to sections of tissue that are within a thickness range less than approximately 1.5 mm. After either step 2138 or 2140 are performed, control proceeds to step 2142, in which a graphic gap display is updated, such as on display device 616. After either of steps 2134 or 2142 have been performed, control proceeds to step 2144, illustrated in FIG. 21(b).

Referring to the flowchart in FIG. 21(b), in step 2144, it is determined whether the gap between the first jaw 80 and the second jaw 50 is greater than a predetermined value referred to as ANVIL_GAP_MIN, which may be stored for example, in a memory location of memory unit 1130. If it is determined in step 2144 that the gap between the first jaw 80 and the second jaw 50 is not greater than a predetermined value referred to as ANVIL_GAP_MIN, then control proceeds to step 2186 as shown in the flowchart in FIG. 21(c). If it is determined in step 2144 that the gap between the first jaw 80 and the second jaw 50 is greater than the value of ANVIL_GAP_MIN, then control proceeds to step 2146. In step 2146, values are set for velocity to a value referred to as CLOSE_SPEED, for torque to a value referred to as CLOSE_TORQUE, and for position to a value referred to as CLOSE_POSITION, each of which may be stored for example, in a memory location of memory unit 1130. In step 2148, movement of the jaws of the surgical device 11 is started, and a stall timer is reset. In step 2150, it is determined whether the CLOSE key is released. If it is determined in step 2150 that the CLOSE key is released, then control proceeds to step 2186 as shown in the flowchart of FIG. 21(c). If it is determined in step 2150 that the CLOSE key is not released, then control proceeds to step 2152, in which it is determined whether the stall timer has a value that is greater than a predetermined value referred to as CLOSE_STALL, which may be stored, for example, in a memory location of memory unit 1130. If it is determined in step 2152 that the stall timer has a value that is greater than the predetermined value referred to as CLOSE_STALL, then, in step 2154, it is determined whether a value corresponding to the gap between the first jaw 80 and the second jaw 50 of the surgical device 11 is less than or equal to a value referred to as ANVIL_GAP_MAX, which may be stored for example, in a memory location of memory unit 1130. If it is determined in step 2154 that the value corresponding to the gap between the first jaw 80 and the second jaw 50 of the surgical device 11 is less than or equal to the predetermined value referred to as ANVIL_GAP_MAX, control proceeds to step 2186 as shown in the flowchart of FIG. 21(c). If it is determined in step 2154 that the value corresponding to the gap between the first jaw 80 and the second jaw 50 of the surgical device 11 is not less than or equal to the predetermined value referred to as ANVIL_GAP_MAX, then in step 2156, a message, such as "FAILED TO CLOSE" is displayed, e.g., on display device 616. In step 2158, an audible chime is issued, and control proceeds to step 2186 illustrated in FIG. 21(c).

Referring back to step 2152, if it is determined in step 2152 that the stall timer has a value that is greater than the value referred to as CLOSE_STALL, then control proceeds to step 2160, in which a current anvil position is obtained. In step 2162, it is determined whether the position of the anvil 505 has changed. If it is determined in step 2162 that the position of the anvil 505 has changed, then, in step 2164, the last known position of the anvil 505 is updated and the stall timer is reset. If it is determined in step 2164 that the position of the anvil 505 has not changed, then control proceeds to step 2166. In step 2166, it is determined whether the current position of the anvil 505 is less than or equal to a value referred to as ANVIL_GAP_GREEN_RANGE, which may be stored, for example, in a memory location of memory unit 1130. If it is determined in step 2166 that the current position of the anvil 505 is not less than or equal to a value referred to as ANVIL_GAP_GREEN_RANGE, control proceeds to step 2168, in which it is determined whether the current position of the anvil 505 is less than or equal to a predetermined value referred to as ANVIL_GAP_MIN, which may be stored, for example, in a memory location of memory unit 1130. If it is determined in step 2168 that the current position of the anvil 505 is less than or equal to the predetermined value referred to as ANVIL_GAP_MIN, then control proceeds to step 2186 as shown in the flowchart of FIG. 21(c). If it is determined in step 2168 that the current position of the anvil 505 is not less than or equal to a predetermined value referred to as ANVIL_GAP_MIN, then in step 2170, it is determined whether the jaws of the surgical device 11 have completed moving. If it is determined in step 2170 that the first jaw 80 and the second jaw 50 of the surgical device 11 have completed their movement, then control proceeds to step 2186 as shown in the flowchart of FIG. 21(c). If it is determined in step 2170 that the first jaw 80 and the second jaw 50 of the surgical device 11 have not completed moving, then control returns to step 2150.

Referring back to step 2166, if it is determined that the current position of the anvil 505 is greater than a value referred to as ANVIL_GAP_GREEN_RANGE, control proceeds to step 2172, in which it is determined whether the current position of the anvil 505 is greater than a predetermined value referred to as ANVIL_GAP_BLUE_RANGE, which may be stored, for example, in a memory location of memory unit 1130. If it is determined in step 2172 that the current position of the anvil 505 is greater than a predetermined value referred to as ANVIL_GAP_BLUE_RANGE, then control proceeds to step 2174, at which it is determined whether the msg flag has a value of "1". If it is determined in step 2174 that the msg flag does not have a value of "1", then, in step 2176, the controller 1122 sets the value of the msg flag at a value of "1", and a message, such as "GREEN OK" is displayed, e.g., on display device 616, indicating to a user that a "green" cartridge, corresponding to a particular thickness of tissue to be stapled, may be used. After step 2176 has been completed, or if in step 2174 it is determined that the msg flag has a value of "1", then control proceeds to step 2178.

If, in step 2172, it is determined that the current position of the anvil 505 is not greater than a predetermined value referred to as ANVIL_GAP_BLUE_RANGE, which may be stored, for example, in a memory location of memory unit 1130, then, in step 2180, it is determined whether the msg flag has a value of "2". If it is determined in step 2180 that the msg flag does not have a value of "2", then, in step 2182, the value of the msg flag is set at a value of "2", and a message, such as "BLUE OK" is displayed, e.g., on display device 616, indicating to a user that a "blue" cartridge, corresponding to a particular thickness of tissue to be stapled, may be used. After step 2182 is completed, or if, in step 2180, it is determined that the msg flag has a value of "2", then control proceeds to step 2178. In step 2178, the graphic gap display, e.g., on the display device 616, is updated. In step 2184, an "IN RANGE" display, such as an light-emitting diode, is turned on, and a DLU FIRED flag in the RAM 1134 of the memory unit 1130 is set. Thereafter, control proceeds to step 2168.

After step 2158, step 2168, or step 2170 have been performed, control proceeds to step 2186, at which point the motor that drives the anvil 505, e.g., motor 680, is turned off. In step 2188, it is determined whether a value corresponding to the current position of the gap is less than or equal to a predetermined value referred to as ANVIL_GAP_MAX, which may be stored, for example, in a memory location of memory unit 1130. If it is determined in step 2188 that the value corresponding to the gap is less than or equal to the predetermined value stored in a memory location referred to as ANVIL_GAP_MAX, control proceeds to step 2192, in which the graphic gap display, e.g., on display device 616, is updated. If it is determined in step 2188 that the value corresponding to the gap is not less than or equal to the predetermined value referred to as ANVIL_GAP_MAX, then in step 2190, the release of all keys of the remote device is awaited, and in step 2194, control returns to the main operating program as shown in FIGS. 20(*a*) to 20(*c*).

FIGS. 22(*a*) to 22(*c*) illustrate an example of an auto-zeroing routine for performing an auto-zero function for the surgical device 11 when attached to the electro-mechanical drive component 610. According to one example embodiment of the present invention, this auto-zeroing routine is executed by the controller 1122, although, as described above, it should be understood that other controllers, electronic devices, etc. may be configured to execute some or all of the steps illustrated in FIGS. 22(*a*) to 22(*c*). Referring to FIG. 22(*a*), in step 2202, the auto-zeroing routine is initialized. In step 2204, the release of all of the keys of the remote device is awaited. In step 2206, a message, such as "CALIBRATING", is displayed, e.g., on display device 616. In step 2208, a READY TO FIRE flag is reset, as well as an AUTOZERO OK flag. In step 2210, the current position of the anvil 505 is set to a value referred to as AUTOZERO_POSITION, which may be stored, for example, in a memory location of memory unit 1130. In step 2212, the torque is set to a value referred to as AUTOZERO_TORQUE, which may be stored, for example, in a memory location of memory unit 1130. In step 2214, the velocity is set to a value referred to as AUTOZERO_SPEED, which may be stored, for example, in a memory location of memory unit 1130. In step 2216, a destination position is set to a value of "0". In step 2218, the motor corresponding to the anvil 505, e.g., motor 680, is signaled to begin moving the anvil 505 so as to close the jaws of the surgical device 11. In step 2220, the stall timer and the last position are reset. Control then proceeds to perform the steps illustrated in the flowchart of FIG. 22(*b*).

In step 2222, it is determined whether the stall timer has a value that is greater than a value referred to as AUTOZERO_STALL, which may be stored, for example, in a memory location of memory unit 1130. If it is determined in step 2222 that the stall timer has a value that is greater than the value referred to as AUTOZERO_STALL, control proceeds to step 2242, at which point the motor corresponding to the anvil 505, e.g., the motor 680, is shut off. If it is determined in step 2222 that the stall timer has a value that is not greater than a predetermined value referred to as AUTOZERO_STALL, then control proceeds to step 2224, in which it is determined whether the current position of the anvil 505 is equal to the last position. If it is determined in step 2224 that the current position of the anvil 505 is not equal to the last position, then in step 2226, the stall timer and the last position are reset. If, in step 2224, it is determined that the current position of the anvil 505 is equal to the last position, then control proceeds to step 2228, at which it is determined whether any of the keys of the remote device, e.g., the wireless RCU 1148 or the wired RCU 1150, are pressed. If it is determined in step 2228 that any of the keys of the remote device are pressed, then in step 2230, the stall timer and the last position are reset. In step 2232, the anvil 505 is opened a predetermined distance referred to as ANVIL_BACKUP, the value of which may be stored, for example, in a memory location of memory unit 1130, or else until the value of the stall timer exceeds the value referred to as AUTOZERO_STALL, or a multiple thereof, e.g., a multiple of the value of AUTOZERO_STALL. In step 2232, the motor, e.g., motor 680, corresponding to the anvil 505 is turned off. In step 2234, an audible chime is issued and a message, such as "PRESS CLOSE TO RECALIBRATE" is displayed, e.g., on display device 616. In step 2236, the release of all keys of the remote device is awaited, and in step 2238, control returns to the main operating program, such as the main operating program illustrated in FIGS. 20(*a*) to 20(*c*).

If, in step 2228, it is determined that none of the keys of the remote are pressed, then control proceeds to step 2240, at which it is determined whether the movement of the jaws is complete. If it is determined in step 2240 that the movement of the jaws is not complete, then control returns to step 2222. If it is determined in step 2240 that the movement of the jaws is complete, then control proceeds to step 2242, in which the motor that drives the anvil 505, e.g., motor 680, is shut off. In step 2244, the values of a distal position and a proximal position are each set to a value of 1.5 mm.

Control then proceeds to the steps illustrated in FIG. 22(*c*). In step 2246, the stall timer and the last position are reset in memory. In step 2248, the velocity is set to a predetermined value referred to as OPEN_SPEED, which may be stored, for example, in a memory location of memory unit 1130. In step 2250, the destination position is set to a predetermined value referred to as OPEN_POSITION, which may be stored, for example, in a memory location of memory unit 1130, and the jaws of the surgical device 11 are caused to begin moving. In step 2252, it is determined whether the stall timer has a value that is greater than the predetermined value referred to as AUTOZERO_STALL or a multiple thereof, e.g., a multiple of the value of AUTOZERO_STALL. If it is determined in step 2252 that the stall timer does not have a value that is greater than the predetermined value referred to as AUTOZERO_STALL, then, in step 2254, it is determined whether the current position of the anvil 505 is equal to its last position. If it is determined in step 2254 that the current position of the anvil 505 is not equal to its last position, then in step 2256, the stall timer and the last position values are reset. If it is determined in step 2254 that the current position of the anvil 505 is the same as the last position, then control proceeds to step 2258, at which it is determined whether any of the keys of the remote device, e.g., wireless RCU 1148 or the wired RCU 1150, are pressed. If it is determined that a key of the remote device is pressed, then, in step 2268, the motor that drives the anvil 505, e.g., motor 680, is shut off. In step 2270, a beep or other audible signal is issued to the user, and a message, such as "PRESS CLOSE TO RE-CALIBRATE" is displayed, e.g., on display device 616. In step 2272, the release of all of the keys of the remote device is awaited, and in step 2274, control returns to a main operating program, such as illustrates in FIGS. 20(*a*) to 20(*c*).

If it is determined in step 2258 that a key of the remote device, e.g., the wireless RCU 1148 or the wired RCU 1150, is not pressed, then, in step 2260, it is determined whether the movement of the jaws of the surgical device 11 is completed. If it is determined in step 2260 that the jaws have not completed their movement, then control returns to step 2252. If it is determined in step 2260 that the movement of the jaws of the surgical device 11 is completed, then, in step 2262, the anvil motor, e.g., motor 680, is turned off, and an audible signal is issued, or a message, such as "READY", is displayed, e.g., on the display device 616. In step 2264, an AUTOZERO_OK flag is set and the release of all of the keys of the remote device is awaited. In step 2266, control returns to a main operating program, such as is shown in FIGS. 20(*a*) to 20(*c*).

FIG. 23 illustrates an example of a jaw-opening routine for opening the surgical device 11 when attached to the electro-mechanical driver component 610. According to one example embodiment of the present invention, this operating program is executed by the controller 1122, although, as described above, it should be understood that other controllers, electronic devices, etc. may execute some or all of the steps of the jaw-opening routine. Referring to FIG. 23, in step 2300, the jaw-opening routine is initialized. In step 2302, an "IN RANGE" display, e.g., a light-emitting-diode, is turned off and the DLU READY flag is cleared in memory. In step 2304, it is determined whether the autozero flag is set in memory. If it is determined in step 2304 that the autozero flag is not set in memory, then in step 2306, a message, such as "PRESS CLOSE TO RE-CALIBRATE", is displayed, e.g., on display device 616. In step 2308, an audible signal or chime is issued to the user. In step 2310, the release of all of the keys of the remote device is awaited before returning, in step 2312. Thereafter, control returns to a main operating program, such as the main operating program illustrated in FIGS. 20(*a*) to 20(*c*).

If, in step 2304, it is determined that the autozero flag has been set, then, in step 2314, the anvil torque is set to a value referred to as OPEN_TORQUE, which may be stored, for example, in a memory location of memory unit 1130. In step 2316, the velocity is set to a predetermined value referred to as OPEN_VELOCITY, which may be stored, for example, in a memory location of memory unit 1130. In step 2318, the destination of the jaws is set to a fully unclamped position. In step 2320, the jaws of the surgical device 11 are caused to start to move. In step 2322, a message, such as "ANVIL OPENING" is displayed, e.g., on display device 616. In step 2324, a msg flag is cleared in the memory. In step 2326, it is determined whether the OPEN key of the remote device is released. If it is determined in step 2326 that the OPEN key is released, then control proceeds to step 2328, at which the anvil motor, e.g., motor 680, is turned off and the release of all of the keys of the remote device is awaited. In step 2330, control returns to a main operating program, such as the main operating program illustrated in FIGS. 20(*a*) to 20(*c*).

If, in step 2326, it is determined that the OPEN key is not released, then, in step 2332, the value of the anvil gap, e.g., the gap between the first jaw 80 and the second jaw 50 of the surgical device 11, is obtained. In step 2334, it is determined whether the gap is greater than a value referred to as ANVIL_FULL_OPEN_GAP, which may be stored, for example, in a memory location of memory unit 1130. If it is determined in step 2334 that the gap is greater than a value referred to as ANVIL_FULL_OPEN_GAP, then, in step 2336, it is determined whether the msg flag is set. If it is determined in step 2336 that the msg flag is not set, then, in step 2338, the msg flag is set and a message, such as "ANVIL FULLY OPEN", is displayed, e.g., on display device 616. Control then proceeds to step 2340. Similarly, if it is determined in step 2334 that the gap is not greater than a predetermined value referred to as ANVIL_FULL_OPEN_GAP, or if it is determined in step 2336 that the msg flag is not set, then control proceeds to step 2340. In step 2340, it is determined whether the movement of the jaws of the surgical device 11 is complete. If it is determined in step 2340 that the movement of the jaws is not complete, control returns to step 2326. If it is determined in step 2340 that the movement of the jaws of the surgical device 11 is complete, then control proceeds to step 2328. As previously mentioned above, in step 2328, the anvil motor, e.g., motor 680, is turned off and the release of all of the keys of the remote device is awaited. In step 2330, control returns to the main operating program illustrated in FIGS. 20(*a*) to 20(*c*).

FIG. 24(*a*) illustrates a staple-firing routine for cutting and stapling a section of tissue clamped between the upper and lower jaws of the surgical device 11, when attached to the electro-mechanical driver component 610. According to one example embodiment of the invention, this operating program is executed by the controller 1122, although, as described above, it should be understood that other controllers, electronic devices, etc. may be configured to execute some or all of the steps of the staple-firing routine. Referring to FIG. 24(*a*), in step 2400, the stapling-firing routine is initialized. In step 2402, it is determined whether the AUTOZERO OK flag is set. If it is determined in step 2402 that the AUTOZERO OK flag is not set, then, in step 2404, an error message, such as "PRESS CLOSE TO RE-CALIBRATE", is displayed, e.g., on display device 616. If it is determined that the AUTOZERO OK flag is set, then control proceeds to step 2406. In step 2406, it is determined whether the DLU READY flag is set. If it is determined in step 2406 that the DLU READY flag is not set, then, in step 2408, an error message, such as "NOT IN RANGE", is displayed, e.g., on display device 616. If it is determined in step 2406 that the DLU READY flag is set, then control proceeds to step 2410. In step 2410, it is determined whether the DLU FIRED flag is set. If it is determined in step 2410 that the DLU FIRED is set, then, in step 2412, an error condition is determined to have occurred, and an error message, such as "NO STAPLES", is displayed, e.g., on display device 616. If it is determined in step 2410 that the DLU FIRED flag is not set, then control proceeds to step 2422. Upon the completion of step 2404, step 2408 or step 2412, control proceeds to step 2414, at which the fire button count is reset. In step 2416, an audible chime is issued. In step 2418, the release of all of the keys is awaited and, in step 2420, control returns to a main operating program, such as the main operating program illustrated in FIGS. 20(*a*) to 20(*c*).

As described above, if it is determined in step 2410 that the DLU FIRED flag is not set, then control proceeds to step 2422. In step 2422, the fire button count is increased. In step 2424, it is determined whether it is the first time that the fire button is pressed. If it is determined in step 2424 that it is the first time that the fire button is pressed, then in step 2426, a message, such as "FIRE KEY READY" is displayed, e.g., on display device 616. In step 2428, the fire button timer is reset. After step 2428 is performed, control returns to step 2418, as described above. If, in step 2424, it is determined that it is not the first time that the fire button is pressed, a message, such as "FIRING", is displayed, e.g., on display device 616 in step 2430. In step 2432, the usage count is decreased and the DLU FIRED flag is set. According to one example embodiment of the present invention, control tries a predetermined number of times, e.g., three times, at a predetermined time intervals, e.g., 100 mS, to decrease the usage count.

Control then proceeds to step 2434, as illustrated in FIG. 24(*b*). In step 2434, the fire motor velocity, e.g., the velocity of the motor that fires the staples, such as motor 676, is set. In addition, in step 2434, a torque limit is set. In step 2436, the fire motor position is set to a predetermined value referred to as FIRE_POSITION, which may be stored, for example, in a memory location of memory unit 1130, and the jaws of the surgical device 11 are caused to start moving. In step 2438, the last known position is set to a value of "0". In addition, in step 2438, the fire and stall timers are reset and the error flag is cleared. In step 2440, it is determined whether the fire or the stall timers has expired. If it is determined in step 2440 that the fire or the stall timers has expired, then in step 2452, the fire motor, e.g., motor 676, is disabled. In step 2454, an error message, such as "FIRING SEQUENCE INCOMPLETE" is displayed, e.g., on the display device 616. In step 2456, a chime or other audible signal is issued and the error flag is set. Thereafter, control proceeds to step 2458.

If it is determined in step 2440 that the fire or the stall timers has expired, then control proceeds to step 2442. In step 2442, it is determined whether the fire motor, e.g., motor 676, has completed its movement. If it is determined in step 2442 that the fire motor, e.g., motor 676, has completed its movement, then control proceeds to step 2452, as discussed above. If it is determined in step 2442 that the fire motor, e.g., motor 676, has not completed its movement, then control proceeds to step 2444. In step 2444, it is determined whether the current position of the anvil 505 is the same as the last position of the anvil 505. If it is determined in step 2444 that the current position of the anvil 505 is not the same as the last position of the anvil 505, then, in step 2446, the last position of the anvil 505 is set equal to the current position of the anvil 505, and the stall timer is reset. After step 2446 has been performed, or if, in step 2444, it is determined that the current position of the anvil 505 is the same as the last position of the anvil 505, control proceeds to step 2448. In step 2448, it is determined whether the knife, such as knife 519, has reached its destination, e.g., the fully extended position. If it is determined in step 2448 that the knife has not reached its destination, then control returns to step 2440. If, in step 2448, it is determined that the knife has reached its destination, then in step 2450, the controller 1122 disables the fire motor, e.g., motor 676.

After the completion of either step 2450 or 2456, control proceeds to step 2458. In step 2458, the "IN RANGE" display, e.g., a light-emitting-diode, is turned off and the DLU READY flag is cleared. In step 2460, the motor current limit is set to full scale. In step 2462, the anvil 505 is caused to start to move back to its initial position. In step 2464, the last known position is set to zero, and the cycle and stall timers are reset. In step 2466, as illustrated in FIG. 24(*c*), it is determined whether the cycle timer is greater than a predetermined value referred to as TIME_FIRE, which may be stored, for example, in a memory location in memory unit 1130. If it is determined in step 2466 that the cycle timer is greater than a predetermined value referred to as TIME_FIRE, then, in step 2468, it is determined whether an error flag is set. If it is determined in step 2468 that the error flag is not set, then, in step 2470, an error message, such as "FIRING SEQUENCE INCOMPLETE" is displayed, e.g., on display device 616. In step 2472, an audible chime is issued and the error flag is set. After step 2472 is performed, or if, in step 2468, the error flag is determined to be set, then control proceeds to step 2482.

If, in step 2466, it is determined that the cycle timer is not greater than the value referred to as TIME_FIRE, then, in step 2474, it is determined whether the stall timer is greater than a predetermined value referred to as TIME_STALL, which may be stored, for example, in a memory location of the memory unit 1130, or a multiple thereof, e.g., a multiple of the value of TIME_FIRE. If it is determined in step 2474 that the stall timer is greater than a predetermined value referred to as TIME_STALL, then control proceeds to step 2468, as previously described. If, in step 2474, it is determined that the stall timer is not greater than the value referred to as TIME_STALL, then control proceeds to step 2476. In step 2476, it is determined whether the current position of the anvil 505 is the same as the last position of the anvil 505. If it is determined in step 2476 that the current position of the anvil 505 is the same as the last position of the anvil 505, then, in step 2478, the last position of the anvil 505 is set equal to the current position of the anvil 505, and the stall timer is reset. After step 2478 has been performed, or if, in step 2476, it is determined that the current position of the anvil 505 is the same as the last position of the anvil 505, then control proceeds to step 2480. In step 2480, it is determined whether the knife, such as knife 519, is fully retracted. If it is determined in step 2480 that the knife is not fully retracted, then control returns to step 2466. If, in step 2480, it is determined that the knife is fully retracted, or after the completion of step 2468 or 2472 as described above, then in step 2482, the fire motor, e.g., motor 676, is disabled. In step 2484, it is determined whether the error flag is set in memory. If it is determined in step 2484 that the error flag is set in memory, then control proceeds to step 2488 and returns to the main operating program. If it is determined in step 2488 that the error flag is not set, then a message, such as "FIRING COMPLETED", is displayed, e.g., on display device 616. Thereafter, in step 2488, control returns to the main operating program.

FIG. 25(*a*) illustrates a shaft-testing routine corresponding to a shaft test for the flexible shaft 620 of the electro-mechanical drive component 610. According to one example embodiment of the invention, this shaft-testing routine is executed by the controller 1122, although, as described above, it should be understood that other controllers, electronics devices, etc. may be configured to execute some or all of the steps of the shaft-testing routine. Referring to FIG. 25(*a*), in step 2500, the shaft-testing routine is initialized. In step 2502, the torque of the knife motor, e.g., motor 676, the velocity and the position are set to jog the corresponding rotatable drive shaft, e.g., rotatable drive shaft 632. In step 2504, a predetermined time period referred to as FIRE_TEST_TIME_OUT, which may be stored, for example, in a memory location of memory unit 1130, is awaited, or else the completion of the movement of the knife 519 is awaited. In step 2506, it is determined whether the time period referred to as FIRE_TEST_TIME_OUT has expired. If it is determined in step 2506 that the time period referred to as FIRE_TEST_TIME_OUT has expired, then, in step 2508, a message, such as "ERROR 006—SEE OPERATOR'S MANUAL" is displayed, e.g., on display device 616. In step 2510, a chime is issued periodically, e.g., once per second, until the power to the electro-mechanical drive component 610 is turned off.

If, in step 2506, it is determined that the time period referred to as FIRE_TEST_TIME_OUT has not expired, then, in step 2512, a predetermined time period referred to as FIRE_STOP_TIME, which may be stored, for example, in a memory location of memory unit 1130, is awaited, in order to ensure that the movement of the knife 519 is complete. In step 2514, it is determined whether a distal end position is less than a predetermined position referred to as FIRE_CHECK_POSITION, a value of which may be stored, for example, in a memory location of memory unit 1130. If it is determined in step 2514 that a distal end position is not less than a predetermined position referred to as FIRE_CHECK_POSITION, then, in step 2516, an error condition is determined to have occurred, and an error message, such as "REPLACE FLEXSHAFT", is displayed, e.g., on display device 616. In step 2518, an audible chime is issued and the error flag is set. After step 2518 has been performed, or if, in step 2514, it is determined that the distal end position is less than FIRE_CHECK_POSITION, then control proceeds to step 2520. In step 2520, the distal end position is set to an original, or home, position. In step 2522, a predetermined time period referred to as FIRE_TEST_TIME_OUT, which may be stored, for example, in a memory location of memory unit 1130, is awaited, or else the completion of the movement of the knife 519 is awaited. In step 2524, it is determined whether the time period referred to as FIRE_TEST_TIME_OUT is expired. If it is determined in step 2524 that the time period referred to as FIRE_TEST_TIME_OUT has expired, then, in step 2526, a message, such as "ERROR 006—SEE OPERATOR'S MANUAL" is displayed, e.g., on display device 616. In step 2528, a chime is issued until the power to the electro-mechanical drive component 610 is turned off. If, in step 2524, it is determined that the time has not expired, then, as illustrated in the flowchart of FIG. 25(*b*), it is determined in step 2530 whether the error flag is set. If it is determined in step 2530 that the error flag is set, then, in step 2536, the release of all of the keys of the remote is awaited. Thereafter, control returns to the main operating program in step 2538. If, in step 2530, it is determined that the error flag is not set, then, in step 2532, the shaft test flag is set to a value of "1". Thereafter, in step 2534, control returns to the main operating program as illustrated in FIGS. 20(*a*) to 20(*c*).

One problem of conventional surgical devices is that they may limit the approach angle at which the device is used. As previously described, conventional surgical devices typically employ an instrument shaft that is perpendicular to the section of tissue to be cut or stapled. When a conventional surgical device is employed corporally, e.g., inside the body of a patient, the device is limited to a single approach angle for cutting and stapling the section of tissue.

By contrast, the surgical device 11 of the present invention may not limit the approach angle at which the device is used. As previously described, the surgical device 11, according to various example embodiments thereof, includes drive shafts 630 and 632 that are coupled to the first jaw 80 at an angle, e.g., perpendicular, to the plane of movement of the first jaw 80 relative to the second jaw 50. Thus, when the surgical device 11 is employed intracorporeally, e.g., inside the body of a patient, the surgical device 11 may not be limited to a single approach angle. Instead, a variety of approach angles may be employed, which may enable an operator to more effectively use the surgical device on various sections of tissue.

Another problem of conventional surgical devices is that they may be difficult to maneuver within the body of a patient. For example, when a conventional surgical device is employed to clamp or staple a section of tissue that is not easily maneuverable, the surgical device must be maneuvered instead. For example, in the case of a section of gastro-intestinal tissue located adjacent to the anal stump, the section of tissue may not be maneuverable prior to or during performance of the operation. A conventional surgical device cannot be employed in such a location, because the approach angle required to be used by an operator may interfere with the pelvis of the patient.

In contrast, the surgical device 11 according to various example embodiments thereof, may be less difficult to maneuver within the body of a patient. For example, in the above-described case of a section of gastro-intestinal tissue located adjacent to the anal stump, the surgical device 11 may be positioned at the very end of the section of gastro-intestinal tissue nearest the anus. Thus, the angled, e.g., perpendicular, arrangement of the drive shafts 630 and 632 relative to the plane of movement of the first jaw 80 relative to the second jaw 50 may improve the maneuverability of the surgical device 11 within the body of the patient.

What is claimed is:

1. A surgical device, comprising:
   a first jaw having a first tissue contacting surface, the tissue contacting surface generally defining a first plane;
   a second jaw in opposed relation to the first jaw and having a second tissue contacting surface, the second tissue contacting surface generally defining a second plane, the first jaw and the second jaw being movable relative to each other;
   a cutting element mounted in the first jaw;
   at least one driver;
   at least one drive socket rotatably supported on the first jaw, the at least one drive socket coupled to a corresponding one of the at least one driver; and
   an electromechanical driver component cooperating with the at least one drive socket;
   wherein the at least one corresponding driver is configured to actuate the cutting element in a direction orthogonal to the tissue contacting surface of at least one of the first jaw and the second jaw.

2. The surgical device according to claim 1, wherein the first jaw further includes a stapling element.

3. The surgical device according to claim 1, further comprising a rotatable drive shaft that is rotated in a first direction to effect opening of the first and second jaws, and rotated in a second direction opposite to the first direction to effect closing of the first and second jaws.

4. The surgical device according to claim 1, wherein the first jaw rotatably supports:
   at least two spur gears;
   a worm and a worm gear in turning and gearing relationship with each other; and
   an externally-threaded screw fixedly connected at one end to the worm gear and in engagement with an internally threaded bore of the second jaw, wherein rotation of the gears results in relative movement of the first jaw and the second jaw.

5. The surgical device according to claim 1, wherein the first jaw rotatably supports two spur gears and a worm in turning and gearing relationship with each other and with a pair of additional worm gears, each of the pair of additional worm gears having a centrally-disposed, internally threaded bore in engagement with one of a pair of externally-threaded screws fixedly connected to the cutting element, wherein rotation of the gears results in relative movement of the cutting element.

6. The surgical device according to claim 1, wherein the at least one drive socket is coupled to a motor via a rotatable drive shaft.

7. The surgical device according to claim 6, wherein the rotatable drive shaft is rotated in a first direction to extend the cutting element and rotated in a second direction opposite to the first direction to retract the cutting element.

8. The surgical device according to claim 6, wherein a rotation axis of the rotatable drive shaft is perpendicular to a plane in which the first and second jaws move.

9. A surgical device, comprising:
   a first jaw including a cutting element;
   a second jaw in opposed relation to the first jaw, the second jaw movable relative to the first jaw;
   a first drive socket and a second drive socket each rotatably supported on the first jaw, the first drive socket coupled to a first driver and the second drive socket coupled to a second driver, the second driver configured to actuate the cutting element in a direction orthogonal to a tissue contacting surface of the first jaw; and
   an electromechanical driver component configured to cooperate with each of the first drive socket and the second drive socket, the first drive socket coupled to a first motor and the second drive socket coupled to a second motor.

10. The surgical device according to claim 9, wherein the first jaw further includes a stapling element.

11. The surgical device according to claim 9, wherein the first jaw rotatably supports:
   at least two spur gears;
   a worm and a worm gear in turning and gearing relationship with each other; and
   an externally-threaded screw fixedly connected at one end to the worm gear and in engagement with an internally-threaded bore of the second jaw, wherein rotation of the gears results in relative movement of the first jaw and the second jaw.

12. The surgical device according to claim 9, wherein the first jaw rotatably supports two spur gears and a worm in turning and gearing relationship with each other and with a pair of additional worm gears, each of the pair of additional worm gears having a centrally-disposed, internally-threaded bore in engagement with one of a pair of externally-threaded screws fixedly connected to the cutting element, wherein rotation of the gears in relative movement of the cutting element.

13. The surgical device according to claim 9, further comprising:
a first rotatable drive shaft interconnecting the first drive socket and the first motor; and
a second rotatable drive shaft interconnecting the second drive socket and the second motor.

14. The surgical device according to claim 13, wherein the first and second motors are controlled by a control system, and wherein the control system is configured to determine, based on the output signal of a sensor, at least one of a rotational position and a direction of rotation of the first rotatable drive shaft.

15. The surgical device according to claim 14, wherein the control system includes a first memory unit, and wherein the first memory unit is configured to store a plurality of operating programs, at least one of the operating programs corresponding to the cutting element.

16. The surgical device according to claim 15, wherein the first jaw, the second jaw and each drive socket are included in a surgical attachment and the rotatable drive shafts are included in an elongated shaft, and wherein the surgical attachment is selectively attachable via the first and second drive sockets to a distal end of the elongated shaft, and wherein the control system is configured to identify the surgical attachment, wherein the surgical attachment is one of a plurality of different types of surgical attachments attachable to the distal end of the elongated shaft, the control system being configured to at least one of read and select the operating program from the first memory unit corresponding to the correct type of surgical attachment.

17. The surgical device according to claim 13, further comprising a sensor corresponding to the first rotatable drive shaft, the sensor outputting a signal in response to and corresponding to a rotation of the first rotatable drive shaft.

18. The surgical device according to claim 9, wherein the second jaw is movable in parallel relative to the first jaw.

* * * * *